US006090558A

United States Patent [19]

Butler et al.

[11] Patent Number: 6,090,558

[45] Date of Patent: Jul. 18, 2000

[54] DNA TYPING BY MASS SPECTROMETRY WITH POLYMORPHIC DNA REPEAT MARKERS

[75] Inventors: John M. Butler, Menlo Park; Jia Li, Union City; Joseph A. Monforte, Berkeley; Christopher H. Becker, Palo Alto, all of Calif.

[73] Assignee: Genetrace Systems, Inc., Alameda, Calif.

[21] Appl. No.: 09/157,177

[22] Filed: Sep. 18, 1998

Related U.S. Application Data

[60] Provisional application No. 60/059,415, Sep. 19, 1997.

[51] Int. Cl.[7] .......................... C07H 21/04; C12P 19/34; C12Q 1/68

[52] U.S. Cl. .......................... 435/6; 435/91.2; 435/91.5; 436/173; 935/8; 935/17; 935/77; 935/78

[58] Field of Search .......................... 435/6, 91.2, 91.5; 436/173; 935/8, 17, 77, 78

[56] References Cited

U.S. PATENT DOCUMENTS

| | | | |
|---|---|---|---|
| 4,683,202 | 7/1987 | Mullis | 435/91 |
| 5,075,217 | 12/1991 | Weber | 435/6 |
| 5,364,759 | 11/1994 | Caskey et al. | 435/6 |
| 5,369,004 | 11/1994 | Polymeropoulos et al. | 435/6 |
| 5,378,602 | 1/1995 | Polymeropoulos et al. | 435/6 |
| 5,468,610 | 11/1995 | Polymeropoulos et al. | 435/6 |
| 5,496,562 | 3/1996 | Burgoyne | 424/488 |
| 5,503,980 | 4/1996 | Cantor | 435/6 |
| 5,547,835 | 8/1996 | Köster | 435/6 |
| 5,580,733 | 12/1996 | Levis et al. | 435/6 |
| 5,582,979 | 12/1996 | Weber | 435/6 |
| 5,599,666 | 2/1997 | Schumm et al. | 435/6 |
| 5,605,798 | 2/1997 | Köster | 435/6 |
| 5,625,184 | 4/1997 | Vestal et al. | 250/287 |
| 5,627,369 | 5/1997 | Vestal et al. | 250/287 |
| 5,661,028 | 8/1997 | Foote | 435/287.2 |
| 5,674,686 | 10/1997 | Schumm et al. | 435/6 |
| 5,691,141 | 11/1997 | Köster | 435/6 |
| 5,700,642 | 12/1997 | Monforte et al. | 435/6 |
| 5,762,876 | 6/1998 | Lincoln et al. | 422/67 |
| 5,766,847 | 6/1998 | Jackle et al. | 435/6 |
| 5,853,989 | 12/1998 | Jeffreys et al. | 435/6 |
| 5,885,775 | 3/1999 | Haff et al. | 435/6 |
| 5,888,819 | 3/1999 | Goelet et al. | 435/5 |

FOREIGN PATENT DOCUMENTS

| | | |
|---|---|---|
| WO 94/16101 | 7/1994 | WIPO . |
| WO 96/29431 | 9/1996 | WIPO . |
| WO 97/33000 | 9/1997 | WIPO . |

OTHER PUBLICATIONS

Alford et al., "Rapid and efficient resolution of parentage by amplification of short tandem repeats," *Am. J. Hum. Genet.*, 55: 190–195, 1994.

Anker et al., "Tetranucleotide repeat polymorphism at the human thyroid peroxidase (hTPO) locus," *Hum. Mol. Genet.*, 1:137, 1992.

Becker et al., "Genetic analysis of short tandem repeat loci by time of flight mass spectrometry," Seventh International Symposium on Human Identification (1996), pp. 158–162, 1997.

Braun et al., "Detecting CFTR gene mutations by using primer oligo base extension and mass spectrometry," *Clin. Chem.* 43:1151–1158, 1997.

Braun et al., "Improved Analysis of Microsatellites Using Mass Spectrometry," *Genomics* 46:18–23, 1997.

Butler et al., "High–throughput STR Analysis by Time–of–Flight Mass Spectrometry," Proceedings of the Second European Symposium on Human Identification 1998, Promega Corporation, in press (1998).

Butler et al., "Rapid and Automated Analysis of Short Tandem Repeat Loci Using Time–of–Flight Mass Spectrometry," Proceedings of the Eighth International Symposium on Human Identification 1997, Promega Corporation, pp. 94–101, 1998.

Butler et al., "Reliable Genotyping of Short Tandem Repeat Loci without an Allelic Ladder Using Time–of–Flight Mass Spectrometry," *Int. J. Legal Med.*, in press (1998).

Crain, "Nucleic acids: overview and analytical strategies," In: *Mass Spectrometry in Biomolecular Sciences,* Caprioli et al., Eds., Kluwer Academic Publishers, Netherlands, pp. 351–379, 1996.

Dubovsky et al., "Sets of short tandem repeat polymorphisms for efficient linkage screening of the human genome," *Hum. Mol. Genet.,* 4:449–452, 1995.

Edwards et al., "DNA typing and genetic mapping with trimeric and tetrameric tandem repeats," *Am. J. Hum. Genet.,* 49:746–756, 1991.

Fregeau and Fourney,"DNA typing with fluorescently tagged short tandem repeats: a sensitive and accurate approach to human identification," *BioTechniques,* 15:100–119, 1993.

Hammond et al., "Evaluation of 13 short tandem repeat loci for use in personal identification applications," *Am. J. Hum. Genet.,* 55:175–189, 1994.

Hauge and Litt, "A study of the origin of 'shadow bands' seen when typing dinucleotide repeat polymorphisms by the PCR™," *Hum. Mol. Genet.,* 2:411–415, 1993.

Hearne and Todd, "Tetranucleotide repeat polymorphism at the HPRT locus," *Nucleic Acids Res.,* 19:5450, 1991.

(List continued on next page.)

*Primary Examiner*—Bennett Celsa
*Attorney, Agent, or Firm*—Law Offices of Jonathan Alan Quine

[57] ABSTRACT

The present invention is related to the fields of genetic mapping and genetic identity detection, including forensic identification and paternity testing. This invention is more specifically directed to the use of mass spectrometry to detect length variation in DNA nucleotide sequence repeats (including variants of common alleles), such as microsatellites and short tandem repeats, and to DNA sequences provided as primers for the analysis of DNA tandem nucleotide repeat polymorphisms at specific loci on specific chromosomes.

30 Claims, 25 Drawing Sheets

OTHER PUBLICATIONS

Huang et al., "Chinese Population data on three tetrameric short tandem repeat loci–HUMTh01, TPOX, and CSF1PO—derived using mutiplex PCR and manual typing," *Forensic Sci. Int.* 71:131–136, 1995.

Jacobson et al., "Applications of mass spectrometry to DNA sequencing," *GATA,* 8(8):223–229, 1991.

Karas et al., "Matrix–assisted laser desorption ionization mass spectrometry," *Mass Spectrom. Rev.,* 10:335–357, 1991.

Kayser et al., "Evaluation of Y–chromosomal STRs: a multicenter study," *Int. J. Legal Med.* 110:125–133, 1997.

Kimpton et al., "Automated DNA profiling employing multiplex amplification of short tandem repeat loci," *PCR™ Meth. Appl.,* 3:13–22, 1993.

Kimpton et al., "Validation of highly discriminating multiplex short tandem repeat amplification systems for individual identification," *Electrophoresis,* 17:1283–1293, 1996.

Kimpton et al., "A further tetranucleotide repeat polymorphism in the vWF gene," *Hum. Mol. Genet.,* 1:287, 1992.

Kirpekar et al., "Matrix assisted laser desorption/ionization mass spectrometry of enzymatically systhesized RNA up to 150 kDa," *Nucleic Acids Research,* 22(19):3866–3870, 1994.

Lareu et al., "A highly variable STR at the D12S391 locus," *Int. J. Leg. Med.,* 109:134–138, 1996.

Lee, et al., Comparison on short tandem repeat (STR) detection using silver, fluorescence and matrix assisted laser desorption ionization time–of–flight mass spectrophotometry (MALDITOF–MS), Proceedings of the Sixth International Symposium on Human Identification, published by Promega Corp., 1995.

Limbach et al., "Characterization of oligonucleotides and nucleic acids by mass spectrometry," *Curr. Opin. Biotech.,* 6:96–102, 1995.

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet," *Anal. Chem.* 69:4540–4546, 1997.

Little et al., "Mass Spectrometry from Miniaturized Arrays for Full Comparative DNA Analysis," *Nature Med.* 3:1413–1416, 1997.

Liu et al., "Rapid screening of genetic polymorphisms using buccal cell DNA with detection by matrix–assisted laser desorption/ionization mass spectrometry," *Rapid Commun. in Mass Spectrometry,* 9:735–743, 1995.

Lygo et al., "The validation of short tandem repeat (STR) loci for use in forensic casework," *Int. J. Leg. Med.,* 107:77–89, 1994.

Nordhoff et al., "Matrix–assisted laser desorption/ionization mass spectrometry of nucleic acids with wavelengths in the ultraviolet and infrared," *Rapid Commun. in Mass Spectrom.,* 6:771–776, 1992.

Parr, Fitzgerald and Smith, "Matrix–assisted laser desorption/ionization mass spectrometry of synthetic oligdoeoxyribonucleotides," *Rapid Commun. in Mass Spectrom.,* 6:369–372, 1992.

Pease, et al., "Light–generated oligonucleotide arrays for rapid DNA sequence analysis," *Proc. Natl. Acad. Sci. USA,* 91:5022–5026, 1994.

Polymeropoulos et al., "Tetranucleotide repeat polymorphism at the human c–fes/fps proto–oncogene (FES)," *Nucleic Acids Res.,* 19:4018, 1991.

Polymeropoulos et al., "Tetranucleotide repeat polymorphism at the human coagulation factor XIII A subunit gene (F13A1)," *Nucleic Acids Res.,* 19:4306, 1991.

Polymeropoulos et al., "Tetranucleotide repeat polymorphism at the human tyrosine hydroxylase gene(TH)," *Nucleic Acids Res.,* 19:3753, 1991.

Polymeropoulos et al., "Dinucleotide repeat polymorphism at the human CTLA4 gene," *Nucleic Acids Res.,* 19:4018, 1991.

Polymeropoulos et al., "Trinucleotide repeat polymorphism at the human met–tRNA–i gene 1 (TRMI)," *Nucleic Acids Res.,* 19:4306, 1991.

Polymeropoulos et al., "Dinucleotide repeat polymorphism at the human non–histone chromosomal protein HMG14 gene," *Nucleic Acids Res.,* 19:3753, 1991.

Puers et al., "Allele ladder characterization of the short tandem repeat polymorphism located in the 5' flanking region to the human coagulation factor XIII A subunit gene," *Genomics,* 23:260–264, 1994.

Puers et al., "Identification of repeat sequence heterogeneity at the polymorphic short tandem repeat locus HUMTH01 [AATG]n and reassignment of alleles in population analysis by using a locus–specific allele ladder," *Am. J. Hum. Genet.,* 53:953–958, 1993.

Roewer et al., "Simple repeat sequences on the human Y chromosome are equally polymorphic as their autosomal counterparts," *Hum. Genet.,* 89:389–394, 1992.

Ross and Belgrader, "Analysis of Short Tandem Repeat Polymorphisms in Human DNA by Matrix–Assisted Laser Desorption/Ionization Mass Spectrometry," *Anal. Chem.* 69:3966–3972, 1997.

Ross et al., "Analysis of DNA Fragments from Conventional and Microfabricated PCR Devices Using Delayed Extraction MALDI–TOF Mass Spectrometry," *Anal. Chem.* 70:2067–2073, 1998.

Sedlak, "GeneTrace Systems bets its future in genomics on TOF mass spectroscopy," *Genetic Engineering News,* 16(21):, 1996. (website: http://www.genetrace.com).

Spengler, et al., "Molecular weight determination of underivatized oligodeoxyribonucleotides by positive–ion matrix–assisted ultraviolet laser–desorption mass spectrometry," *Rapid Commun. Mass Spectrom.,* 4:99–102, 1990.

Stults and Marsters, "Characterization of oligodeoxynucleotide conjugates by electrospray ionization mass spectrometry," Presented at: Proceedings of the 39th ASMS Conference on Mass Spectrometry and Allied Topics, Nashville, Tennessee, pp. 1161–1162, May 19–24, 1991.

Stults and Marsters, "Improved electrospray ionization of synthetic oligodeoxynucleotides," *Rapid Commun. Mass Spectrom.,* 5:359–363, 1991.

Tanaka, et al., "Protein and polymer analyses up to m/z 100 000 by laser ionization time–of–flight mass spectrometry," *Rapid Commun. in Mass Spectrometry,* 2:151–153, 1988.

Tang et al., "Detection of 500–nucleotide DNA by laser desorption mass spectrometry," *Rapid Commun. in Mass Spectrometry,* 8(9):727–730, 1994.

Tang, et al., "Laser mass spectrometry of polydeoxyribothymidylic acid mixtures," *Rapid Commun. Mass Spectrom,* 7:63–66, 1993.

Tang, et al., "Matrix–assisted laser desorption/ionization of restriction enzyme–digested DNA," *Rapid Commun. in Mass Spectrometry,* 8:183–186, 1994.

Taranenko et al., "Matrix–assisted laser desorption/ionization for short tandem repeat loci," *Rapid Commun. Mass Spectrom.* 12:413–418, 1998.

The Utah Marker Development Group "A collection of ordered tetranucleotide–repeat markers from the human genome," *Am. J. Hum. Genet.,* 57:619–628, 1995.

Weber and May, "Abundant class of human DNA polymorphisms which can be typed using the polymerase chain reaction," *Am. J. Hum. Genet.,* 44:388–396, 1989.

Wenz et al., "High–Precision Genotyping by Denaturing Capillary Electrophoresis," *Genome Res.* 8:69–80, 1998.

Wu, et al., "Matrix–assisted laser desorption time–of–flight mass spectrometry of oligonucleotides using 3–hydroxypicolinic acid as an ultraviolet–sensitive matrix," *Rapid Commun. in Mass Spectrometry,* 7:142–146, 1993.

Wu et al., "Time–of–flight mass spectrometry of underivatized single–stranded DNA oligomers by matrix–assisted laser desorption," *Anal. Chem.,* 66:1637–1645, 1994.

Ziegle et al., "Application of automated DNA sizing technology for genotyping microsatellite loci," *Genomics,* 14:1026–1031,1992.

SEQUENCE LISTING

<160> NUMBER OF SEQ ID NOS: 135

<210> SEQ ID NO 1
<211> LENGTH: 23
<212> TYPE: DNA
<213> ORGANISM: Homo sapiens

<400> SEQUENCE: 1
acagtaactg ccttcataga tag 23

<210> SEQ ID NO 2
<211> LENGTH: 22
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 2
gtgtcagacc ctgttctaag ta 22

<210> SEQ ID NO 3
<211> LENGTH: 19
<212> TYPE: DNA
<213> ORGANISM: Homo sapiens

<400> SEQUENCE: 3
actgcagtcc aatctgggt 19

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (19)
<223> OTHER INFORMATION: 2'-deoxythymidine-5'-(S)-phosphorothioate

<400> SEQUENCE: 4
atgaaatcaa cagaggcttg 20

<210> SEQ ID NO 5
<211> LENGTH: 25
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (24)
<223> OTHER INFORMATION: 2'-deoxythymidine-5'-(S)-phosphorothioate

<400> SEQUENCE: 5
ctctttggta tccttatgta atatt 25

-continued

<210> SEQ ID NO 6
<211> LENGTH: 29
<212> TYPE: DNA
<213> ORGANISM: Homo sapiens

<400> SEQUENCE: 6
atctgtatcc ttatttatac ctctatcta 29

<210> SEQ ID NO 7
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-phosphorothioate

<400> SEQUENCE: 7
tgtcatagtt tagaacgaac taac 24

<210> SEQ ID NO 8
<211> LENGTH: 26
<212> TYPE: DNA
<213> ORGANISM: Homo sapiens

<400> SEQUENCE: 8
aaaaactatc aatctgtcta tctatc 26

<210> SEQ ID NO 9
<211> LENGTH: 27
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (26)
<223> OTHER INFORMATION: 2'-deoxythymidine-5'-(S)-phosphorothioate

<400> SEQUENCE: 9
tttgtatttc atgtgtacat tcgtatc 27

<210> SEQ ID NO 10
<211> LENGTH: 28
<212> TYPE: DNA
<213> ORGANISM: Homo sapiens

<400> SEQUENCE: 10
acctatcctg tagattattt tcactgtg 28

<210> SEQ ID NO 11
<211> LENGTH: 23
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (22)
<223> OTHER INFORMATION: 2'-deoxythymidine-5'-(S)-phosphorothioate -continued

<400> SEQUENCE: 11
cccatctaac gcctatctgt att 23

<210> SEQ ID NO 12
<211> LENGTH: 22
<212> TYPE: DNA
<213> ORGANISM: Homo sapiens

<400> SEQUENCE: 12
gcccaaaaag acagacagaa ag 22

<210> SEQ ID NO 13
<211> LENGTH: 23
<212> TYPE: DNA
<213> ORGANISM: Homo sapiens

<400> SEQUENCE: 13
agacagacag acaggtggat aga 23

<210> SEQ ID NO 14
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (23)
<223> OTHER INFORMATION: 2'-deoxythymidine-5'-(S)-phosphorothioate

<400> SEQUENCE: 14
tctctgtttt gtctttcaat gata 24

<210> SEQ ID NO 15
<211> LENGTH: 21
<212> TYPE: DNA
<213> ORGANISM: Homo sapiens

<400> SEQUENCE: 15
tgagtgacaa attgagacct t 21

<210> SEQ ID NO 16
<211> LENGTH: 26
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (25)
<223> OTHER INFORMATION: 2'-deoxythymidine-5'-(S)-phosphorothioate

<400> SEQUENCE: 16
gtcttacaat aacagttgct actatt 26

<210> SEQ ID NO 17
<211> LENGTH: 20
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated -continued
<220> FEATURE:
<221> NAME/KEY: misc_feature
<222> LOCATION: (19)
<223> OTHER INFORMATION: 2'-deoxythymidine-5'-(S)-phosphorothioate

<400> SEQUENCE: 17
cccaagtgaa ttgccttcta 20

<210> SEQ ID NO 18
<211> LENGTH: 29
<212> TYPE: DNA
<213> ORGANISM: Homo sapiens

<400> SEQUENCE: 18
gtagatagac tggatagata gacgataga 29

<210> SEQ ID NO 19
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (23)
<223> OTHER INFORMATION: 2'-deoxythymidine-5'-(S)-phosphorothioate

<400> SEQUENCE: 19
gtgttttaga tagatagata ggta 24

<210> SEQ ID NO 20
<211> LENGTH: 20
<212> TYPE: DNA
<213> ORGANISM: Homo sapiens

<400> SEQUENCE: 20
ggttaaggag agtgtcacta 20

<210> SEQ ID NO 21
<211> LENGTH: 19
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (16)
<223> OTHER INFORMATION: 2'-deoxythymidine-5'-(S)-phosphorothioate

<400> SEQUENCE: 21
cagagcaaga cttcatctg 19

<210> SEQ ID NO 22
<211> LENGTH: 18
<212> TYPE: DNA
<213> ORGANISM: Homo sapiens

<400> SEQUENCE: 22
tcattttagt gcatgttc 18

<210> SEQ ID NO 23
<211> LENGTH: 23
<212> TYPE: DNA

-continued

<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (22)
<223> OTHER INFORMATION: 2'-deoxythymidine-5'-(S)-phosphorothioate

<400> SEQUENCE: 23
ttaggagaca aggatagcag ttc 23

<210> SEQ ID NO 24
<211> LENGTH: 22
<212> TYPE: DNA
<213> ORGANISM: Homo sapiens

<400> SEQUENCE: 24
gcgaaagaat gagactacat ct 22

<210> SEQ ID NO 25
<211> LENGTH: 27
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (26)
<223> OTHER INFORMATION: 2'-deoxythymidine-5'-(S)-phosphorothioate

<400> SEQUENCE: 25
aaaattaggc atatttacaa gctagtt 27

<210> SEQ ID NO 26
<211> LENGTH: 25
<212> TYPE: DNA
<213> ORGANISM: Homo sapiens

<400> SEQUENCE: 26
tctgtaattg ccagcaaaaa agaaa 25

<210> SEQ ID NO 27
<211> LENGTH: 29
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (28)
<223> OTHER INFORMATION: 2'-deoxythymidine-5'-(S)-phosphorothioate

<400> SEQUENCE: 27
gtctccatct ttgtctctat ctctatctg 29

<210> SEQ ID NO 28
<211> LENGTH: 22
<212> TYPE: DNA
<213> ORGANISM: Homo sapiens

<400> SEQUENCE: 28
gagaagggca tgaatttgct tt 22

-continued

<210> SEQ ID NO 29
<211> LENGTH: 20
<212> TYPE: DNA
<213> ORGANISM: Homo sapiens

<400> SEQUENCE: 29
cctgttcctc ccttattccc 20

<210> SEQ ID NO 30
<211> LENGTH: 21
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (20)
<223> OTHER INFORMATION: 2'-deoxythymidine-5'-(S)-phosphorothioate

<400> SEQUENCE: 30
gggaacacag actccatggt g 21

<210> SEQ ID NO 31
<211> LENGTH: 22
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 31
cttagggaac cctcactgaa tg 22

<210> SEQ ID NO 32
<211> LENGTH: 22
<212> TYPE: DNA
<213> ORGANISM: Homo sapiens

<400> SEQUENCE: 32
gtccttgtca gcgtttattt gc 22

<210> SEQ ID NO 33
<211> LENGTH: 22
<212> TYPE: DNA
<213> ORGANISM: Homo sapiens

<400> SEQUENCE: 33
gtgtcagacc ctgttctaag ta 22

<210> SEQ ID NO 34
<211> LENGTH: 20
<212> TYPE: DNA
<213> ORGANISM: Homo sapiens

<400> SEQUENCE: 34
atgaaatcaa cagaggcttg 20

<210> SEQ ID NO 35

-continued

<211> LENGTH: 25
<212> TYPE: DNA
<213> ORGANISM: Homo sapiens

<400> SEQUENCE: 35
ctctttggta tccttatgta atatt 25

<210> SEQ ID NO 36
<211> LENGTH: 24
<212> TYPE: DNA
<213> ORGANISM: Homo sapiens

<400> SEQUENCE: 36
tgtcatagtt tagaacgaac taac 24

<210> SEQ ID NO 37
<211> LENGTH: 27
<212> TYPE: DNA
<213> ORGANISM: Homo sapiens

<400> SEQUENCE: 37
tttgtatttc atgtgtacat tcgtatc 27

<210> SEQ ID NO 38
<211> LENGTH: 23
<212> TYPE: DNA
<213> ORGANISM: Homo sapiens

<400> SEQUENCE: 38
cccatctaac gcctatctgt att 23

<210> SEQ ID NO 39
<211> LENGTH: 24
<212> TYPE: DNA
<213> ORGANISM: Homo sapiens

<400> SEQUENCE: 39
tctctgtttt gtctttcaat gata 24

<210> SEQ ID NO 40
<211> LENGTH: 26
<212> TYPE: DNA
<213> ORGANISM: Homo sapiens

<400> SEQUENCE: 40
gtcttacaat aacagttgct actatt 26

<210> SEQ ID NO 41
<211> LENGTH: 20
<212> TYPE: DNA
<213> ORGANISM: Homo sapiens

<400> SEQUENCE: 41
cccaagtgaa ttgccttcta 20

<210> SEQ ID NO 42
<211> LENGTH: 24
<212> TYPE: DNA
<213> ORGANISM: Homo sapiens

<400> SEQUENCE: 42
gtgttttaga tagatagata ggta 24

-continued

<210> SEQ ID NO 43
<211> LENGTH: 19
<212> TYPE: DNA
<213> ORGANISM: Homo sapiens

<400> SEQUENCE: 43
cagagcaaga cttcatctg 19

<210> SEQ ID NO 44
<211> LENGTH: 23
<212> TYPE: DNA
<213> ORGANISM: Homo sapiens

<400> SEQUENCE: 44
ttaggagaca aggatagcag ttc 23

<210> SEQ ID NO 45
<211> LENGTH: 27
<212> TYPE: DNA
<213> ORGANISM: Homo sapiens

<400> SEQUENCE: 45
aaaattaggc atatttacaa gctagtt 27

<210> SEQ ID NO 46
<211> LENGTH: 29
<212> TYPE: DNA
<213> ORGANISM: Homo sapiens

<400> SEQUENCE: 46
gtctccatct ttgtctctat ctctatctg 29

<210> SEQ ID NO 47
<211> LENGTH: 21
<212> TYPE: DNA
<213> ORGANISM: Homo sapiens

<400> SEQUENCE: 47
gggaacacag actccatggt g 21

<210> SEQ ID NO 48
<211> LENGTH: 22
<212> TYPE: DNA
<213> ORGANISM: Homo sapiens

<400> SEQUENCE: 48
cttagggaac cctcactgaa tg 22

<210> SEQ ID NO 49
<211> LENGTH: 21
<212> TYPE: DNA
<213> ORGANISM: Homo sapiens

<400> SEQUENCE: 49
gtgagttagc cgtttagcga t 21

<210> SEQ ID NO 50
<211> LENGTH: 18
<212> TYPE: DNA
<213> ORGANISM: Homo sapiens

<400> SEQUENCE: 50
gagcgagagt ccgtctca 18

-continued

<210> SEQ ID NO 51
<211> LENGTH: 24
<212> TYPE: DNA
<213> ORGANISM: Homo sapiens

<400> SEQUENCE: 51
ttcaatcata cacccatatc tgtc 24

<210> SEQ ID NO 52
<211> LENGTH: 22
<212> TYPE: DNA
<213> ORGANISM: Homo sapiens

<400> SEQUENCE: 52
atagagggat aggtaggcag gc 22

<210> SEQ ID NO 53
<211> LENGTH: 19
<212> TYPE: DNA
<213> ORGANISM: Homo sapiens

<400> SEQUENCE: 53
tttttcttgt atcaccatt 19

<210> SEQ ID NO 54
<211> LENGTH: 22
<212> TYPE: DNA
<213> ORGANISM: Homo sapiens

<400> SEQUENCE: 54
aaacctacca atcccattcc tt 22

<210> SEQ ID NO 55
<211> LENGTH: 23
<212> TYPE: DNA
<213> ORGANISM: Homo sapiens

<400> SEQUENCE: 55
tggtcttcta cttgtgtcaa tac 23

<210> SEQ ID NO 56
<211> LENGTH: 23
<212> TYPE: DNA
<213> ORGANISM: Homo sapiens

<400> SEQUENCE: 56
tgtctcatag aaaagacata cat 23

<210> SEQ ID NO 57
<211> LENGTH: 23
<212> TYPE: DNA
<213> ORGANISM: Homo sapiens

<400> SEQUENCE: 57
ctggatttct tggttatagt aaa 23

<210> SEQ ID NO 58
<211> LENGTH: 23
<212> TYPE: DNA
<213> ORGANISM: Homo sapiens

<400> SEQUENCE: 58
aagctggtag agagatacac aga 23

-continued

<210> SEQ ID NO 59
<211> LENGTH: 18
<212> TYPE: DNA
<213> ORGANISM: Homo sapiens

<400> SEQUENCE: 59
agccacaccc ataacttt 18

<210> SEQ ID NO 60
<211> LENGTH: 22
<212> TYPE: DNA
<213> ORGANISM: Homo sapiens

<400> SEQUENCE: 60
gaatgcagag aaagagaatc ta 22

<210> SEQ ID NO 61
<211> LENGTH: 18
<212> TYPE: DNA
<213> ORGANISM: Homo sapiens

<400> SEQUENCE: 61
agaaatggct tggccttg 18

<210> SEQ ID NO 62
<211> LENGTH: 18
<212> TYPE: DNA
<213> ORGANISM: Homo sapiens

<400> SEQUENCE: 62
taaaggattg caggaggg 18

<210> SEQ ID NO 63
<211> LENGTH: 23
<212> TYPE: DNA
<213> ORGANISM: Homo sapiens

<400> SEQUENCE: 63
gaataagatt ctgttgaagg aaa 23

<210> SEQ ID NO 64
<211> LENGTH: 24
<212> TYPE: DNA
<213> ORGANISM: Homo sapiens

<400> SEQUENCE: 64
aatcttctct ctttctacct ctct 24

<210> SEQ ID NO 65
<211> LENGTH: 20
<212> TYPE: DNA
<213> ORGANISM: Homo sapiens

<400> SEQUENCE: 65
agggctgatg aggtgaaata 20

<210> SEQ ID NO 66
<211> LENGTH: 24
<212> TYPE: DNA
<213> ORGANISM: Homo sapiens

<400> SEQUENCE: 66

-continued tcaacaacaa cacatataag atga 24

<210> SEQ ID NO 67
<211> LENGTH: 25
<212> TYPE: DNA
<213> ORGANISM: Homo sapiens

<400> SEQUENCE: 67
catatatttg tagatggata gaaga 25

<210> SEQ ID NO 68
<211> LENGTH: 23
<212> TYPE: DNA
<213> ORGANISM: Homo sapiens

<400> SEQUENCE: 68
gagttctcca gagaaacaga atc 23

<210> SEQ ID NO 69
<211> LENGTH: 29
<212> TYPE: DNA
<213> ORGANISM: Homo sapiens

<400> SEQUENCE: 69
cagactagat agatagatac gtacataca 29

<210> SEQ ID NO 70
<211> LENGTH: 24
<212> TYPE: DNA
<213> ORGANISM: Homo sapiens

<400> SEQUENCE: 70
tcaaagagtg acaaagaaac taaa 24

<210> SEQ ID NO 71
<211> LENGTH: 24
<212> TYPE: DNA
<213> ORGANISM: Homo sapiens

<400> SEQUENCE: 71
ccatccatct atcatctatt tatt 24

<210> SEQ ID NO 72
<211> LENGTH: 23
<212> TYPE: DNA
<213> ORGANISM: Homo sapiens

<400> SEQUENCE: 72
acctacatta gtctgtgttc tct 23

<210> SEQ ID NO 73
<211> LENGTH: 24
<212> TYPE: DNA
<213> ORGANISM: Homo sapiens

<400> SEQUENCE: 73
aagaaagaat gacccttgga attt 24

<210> SEQ ID NO 74
<211> LENGTH: 19
<212> TYPE: DNA
<213> ORGANISM: Homo sapiens

<400> SEQUENCE: 74

-continued gggcgacaga gcaagactc 19

<210> SEQ ID NO 75
<211> LENGTH: 20
<212> TYPE: DNA
<213> ORGANISM: Homo sapiens

<400> SEQUENCE: 75
tggagtcgca agctgaacta 20

<210> SEQ ID NO 76
<211> LENGTH: 23
<212> TYPE: DNA
<213> ORGANISM: Homo sapiens

<400> SEQUENCE: 76
ctgagtgaca gagtgagaac ctg 23

<210> SEQ ID NO 77
<211> LENGTH: 19
<212> TYPE: DNA
<213> ORGANISM: Homo sapiens

<400> SEQUENCE: 77
atcaatggat gcataggta 19

<210> SEQ ID NO 78
<211> LENGTH: 23
<212> TYPE: DNA
<213> ORGANISM: Homo sapiens

<400> SEQUENCE: 78
gcctccatat cacttgagct aat 23

<210> SEQ ID NO 79
<211> LENGTH: 25
<212> TYPE: DNA
<213> ORGANISM: Homo sapiens

<400> SEQUENCE: 79
gccttactga cttactacat aacga 25

<210> SEQ ID NO 80
<211> LENGTH: 21
<212> TYPE: DNA
<213> ORGANISM: Homo sapiens

<400> SEQUENCE: 80
gagcaagact gcatctcaaa a 21

<210> SEQ ID NO 81
<211> LENGTH: 23
<212> TYPE: DNA
<213> ORGANISM: Homo sapiens

<400> SEQUENCE: 81
tggaaaaata ttctgggaag ata 23

<210> SEQ ID NO 82
<211> LENGTH: 22
<212> TYPE: DNA
<213> ORGANISM: Homo sapiens -continued

<400> SEQUENCE: 82
cctgttgaca tttttaaaac ca 22

<210> SEQ ID NO 83
<211> LENGTH: 18
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (16)
<223> OTHER INFORMATION: 2'-deoxythymidine-5'-(S)-phosphorothioate

<400> SEQUENCE: 83
gagcgagagt ccgtctca 18

<210> SEQ ID NO 84
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (23)
<223> OTHER INFORMATION: 2'-deoxythymidine-5'-(S)-phosphorothioate

<400> SEQUENCE: 84
ttcaatcata cacccatatc tgtc 24

<210> SEQ ID NO 85
<211> LENGTH: 19
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (18)
<223> OTHER INFORMATION: 2'-deoxythymidine-5'-(S)-phosphorothioate

<400> SEQUENCE: 85
tttttcttgt atcaccatt 19

<210> SEQ ID NO 86
<211> LENGTH: 23
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 86
tggtcttcta cttgtgtcaa tac 23

<210> SEQ ID NO 87
<211> LENGTH: 23

-continued

```
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (20)
<223> OTHER INFORMATION: 2'-deoxythymidine-5'-(S)-phosphorothioate

<400> SEQUENCE: 87

ctggatttct tggttatagt aaa                                              23


<210> SEQ ID NO 88
<211> LENGTH: 22
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 88

gaatgcagag aaagagaatc ta                                               22


<210> SEQ ID NO 89
<211> LENGTH: 18
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (17)
<223> OTHER INFORMATION: 2'-deoxythymidine-5'-(S)-phosphorothioate

<400> SEQUENCE: 89

agaaatggct tggccttg                                                    18


<210> SEQ ID NO 90
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (22)
<223> OTHER INFORMATION: 2'-deoxythymidine-5'-(S)-phosphorothioate

<400> SEQUENCE: 90

aatcttctct ctttctacct ctct                                             24


<210> SEQ ID NO 91
<211> LENGTH: 20
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
```

-continued

<221> NAME/KEY: misc_feature
<222> LOCATION: (19)
<223> OTHER INFORMATION: 2'-deoxythymidine-5'-(S)-phosphorothioate

<400> SEQUENCE: 91
agggctgatg aggtgaaata 20

<210> SEQ ID NO 92
<211> LENGTH: 23
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (22)
<223> OTHER INFORMATION: 2'-deoxythymidine-5'-(S)-phosphorothioate

<400> SEQUENCE: 92
gagttctcca gagaaacaga atc 23

<210> SEQ ID NO 93
<211> LENGTH: 29
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (26)
<223> OTHER INFORMATION: 2'-deoxythymidine-5'-(S)-phosphorothioate

<400> SEQUENCE: 93
cagactagat agatagatac gtacataca 29

<210> SEQ ID NO 94
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (23)
<223> OTHER INFORMATION: 2'-deoxythymidine-5'-(S)-phosphorothioate

<400> SEQUENCE: 94
ccatccatct atcatctatt tatt 24

<210> SEQ ID NO 95
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (23)
<223> OTHER INFORMATION: 2'-deoxythymidine-5'-(S)-phosphorothioate

<400> SEQUENCE: 95
aagaaagaat gacccttgga attt 24

-continued

<210> SEQ ID NO 96
<211> LENGTH: 20
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (19)
<223> OTHER INFORMATION: 2'-deoxythymidine-5'-(S)-phosphorothioate

<400> SEQUENCE: 96
tggagtcgca agctgaacta 20

<210> SEQ ID NO 97
<211> LENGTH: 19
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (18)
<223> OTHER INFORMATION: 2'-deoxythymidine-5'-(S)-phosphorothioate

<400> SEQUENCE: 97
atcaatggat gcataggta 19

<210> SEQ ID NO 98
<211> LENGTH: 25
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (20)
<223> OTHER INFORMATION: 2'-deoxythymidine-5'-(S)-phosphorothioate

<400> SEQUENCE: 98
gccttactga cttactacat aacga 25

<210> SEQ ID NO 99
<211> LENGTH: 23
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (22)
<223> OTHER INFORMATION: 2'-deoxythymidine-5'-(S)-phosphorothioate

<400> SEQUENCE: 99
tggaaaaata ttctgggaag ata 23

<210> SEQ ID NO 100
<211> LENGTH: 23
<212> TYPE: DNA
<213> ORGANISM: Homo sapiens
<220> FEATURE:

-continued

<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 100
acagtaactg ccttcataga tag 23

<210> SEQ ID NO 101
<211> LENGTH: 22
<212> TYPE: DNA
<213> ORGANISM: Homo sapiens

<400> SEQUENCE: 101
gcctgttcct cccttatttc cc 22

<210> SEQ ID NO 102
<211> LENGTH: 23
<212> TYPE: DNA
<213> ORGANISM: Homo sapiens

<400> SEQUENCE: 102
aggtcacagg gaacacagac tcc 23

<210> SEQ ID NO 103
<211> LENGTH: 23
<212> TYPE: DNA
<213> ORGANISM: Homo sapiens
<220> FEATURE:
<221> NAME/KEY: misc_feature
<222> LOCATION: (1)
<223> OTHER INFORMATION: Biotinylated
<220> FEATURE:
<221> NAME/KEY: misc_feature
<222> LOCATION: (21)
<223> OTHER INFORMATION: 2'-deoxythymidine-5'-(S)-phosphorothioate

<400> SEQUENCE: 103
aggtcacagg gaacacagac tcc 23

<210> SEQ ID NO 104
<211> LENGTH: 315
<212> TYPE: DNA
<213> ORGANISM: Homo sapiens

<400> SEQUENCE: 104
aacctgagtc tgccaaggac tagcaggttg ctaaccaccc tgtgtctcag ttttcctacc 60
tgtaaaatga agatattaac agtaactgcc ttcatagata gaagatagat agattagata 120
gatagataga tagatagata gatagataga tagatagata gataggaagt acttagaaca 180
gggtctgaca caggaaatgc tgtccaagtg tgcaccagga gatagtatct gagaaggctc 240
agtctggcac catgtgggtt gggtgggaac ctggaggctg gagaatgggc tgaagatggc 300
cagtggtgtg tggaa 315

<210> SEQ ID NO 105
<211> LENGTH: 307
<212> TYPE: DNA
<213> ORGANISM: Homo sapiens

<400> SEQUENCE: 105
tctaattaaa gtggtgtccc agataatctg tactaataaa agtatatttt aatagcaagt 60

-continued atgtgacaag ggtgattttc ctctttggta tccttatgta atattttgaa gatagataga 120
tagatagata gatagataga tagatagata gataggtaga tagaggtata aataaggata 180
cagatatagn tacaaatgtt gtaaactgtg gctatgattg gaatcacttg gctaaaaagc 240
gctnaagcnt tcctctgnga gaggcaatta cttttttnct taggnactnc ctcancagtc 300 tnttngc 307

<210> SEQ ID NO 106
<211> LENGTH: 334
<212> TYPE: DNA
<213> ORGANISM: Homo sapiens

<400> SEQUENCE: 106
aatttttgta ttttttttag agacggggtt tcaccatgtt ggtcaggctg actatggagt 60
tattttaagg ttaatatata taaagggtat gatagaacac ttgtcatagt ttagaacgaa 120
ctaacgatag atagatagat agatagatag atagatagat agatagatag atagacagat 180
tgatagtttt tttttatctc actaaatagt ctatagtaaa catttaatta ccaatatttg 240
gtgcaattct gtcaatgagg ataaatgtgg aatcgttata attcttaaga atatatattc 300
cctctgagtt tttgatacct cagattttaa ggcc 334

<210> SEQ ID NO 107
<211> LENGTH: 340
<212> TYPE: DNA
<213> ORGANISM: Homo sapiens

<400> SEQUENCE: 107
tggcaactta tatgtatttt tgtatttcat gtgtacattc gtatctatct atctatctat 60
ctatctatct atctatctat ctatctatct attccccaca gtgaaaataa tctacaggat 120
aggtaaataa attaaggcat attcacgcaa tgggatacgn tacagtgatg aaaatgaact 180
aattatagct acgtgaaact atactcatgn acacaatttg gtaaaagaaa ctgggaacaa 240
gaatacatac ggtttttgnc agctgtgcta ttttacattc ccaacaacaa tgcacagggt 300
ttcagnttct ccacatnctt gtcaacattn tgttattttg 340

<210> SEQ ID NO 108
<211> LENGTH: 286
<212> TYPE: DNA
<213> ORGANISM: Homo sapiens

<400> SEQUENCE: 108
tgggatgggt tgctggacat ggtatcacag aagtctggga tgtggaggag agttcatttc 60
tttagtgggc atccgtgact ctctggactc tgacccatct aacgcctatc tgtatttaca 120
aatacattat ctatctatct atctatctat ctatctatct atctatctat ctatctatca 180
atcatctatc tatctttctg tctgtctttt tgggctgcct atggctcaac ccaagttgaa 240
ggaggagatt tgaccaacaa ttcaagctct ctgaatatgt tttgaa 286

<210> SEQ ID NO 109
<211> LENGTH: 426
<212> TYPE: DNA
<213> ORGANISM: Homo sapiens

<400> SEQUENCE: 109
atggctgccc tcacggctgc accgggagga tgactgtntt cccactctca gtcctgccga 60

-continued ggtgcctgac agccctgcac ccaggagctg gggggtctaa gagcttgtaa aaagtgtaca 120
agtgccagat gctcgttgtg cacaaatcta aatgcagaaa agcactgaaa gaagaatcca 180
gaaaaccaca gttcccattt ttatatggga gcaaacaaag gcagatccca agctcttcct 240
cttccctaga tcaatacaga cagacagaca ggtggataga tagatagata gatagataga 300
tagatagata gatagatatc attgaaagac aaaacagaga tggatgatag atacatgctt 360
acagatgcac acacaaacgt aaatggtatn aaaaatngga tncactcttg tanggttgtt 420 nttacc 426

<210> SEQ ID NO 110
<211> LENGTH: 350
<212> TYPE: DNA
<213> ORGANISM: Homo sapiens

<400> SEQUENCE: 110
aggttaaggc tgcagtgagc catgttcatg ccactgcact tcactctgag tgacaaattg 60
agaccttgtc tcagaaagaa agaaagaaag aaagaaagaa agaaagaaag aangaaagaa 120
agaaagtaag aaaaagagag ggaaagaaag agaaanagna aanaaatagt agcaactgtt 180
attgtaagac atctccacac accagagaag ttaattttaa ttttaacatg ttaagaacag 240
agagaagcca acatgtccac cttaggctga cggtttgttt atttgtgttg ttgctggtag 300
tcgggtttgt tatttttaaa gtagcttatc caatacttca ttaacaattt 350

<210> SEQ ID NO 111
<211> LENGTH: 528
<212> TYPE: DNA
<213> ORGANISM: Homo sapiens

<400> SEQUENCE: 111
ctaccaatca tagtggaaag caaagacaga gcaaggcatc tcacatggct agagcaggag 60
caagagaaag ataggggagc ttgtagatgg tctgttatgg gacttttctc agtctccata 120
aatatgtgag tcaattcccc aagtgaattg ccttctatct atctatctat ctgtctgtct 180
gtctgtctgt ctgtctatct atctatatct atctatctat catctatcta tctatctatc 240
tatctatcta tctatctatc tatcgtctat ctatccagtc tatctacctc ctattagtct 300
gtctctggag aacattgact aatacaacat ctttaatata tcacagttta atttcaagtt 360
atatcatacc acttcataca ttatataaaa ccttacagtg tttctccctt ctcagtgttt 420
atggctagta attttttact gggtgccaga cactaatttt tattttgcta agtggtgaat 480
attttttata tccttaaaaa tatttttgag tgttgatctg ggtaaagt 528

<210> SEQ ID NO 112
<211> LENGTH: 194
<212> TYPE: DNA
<213> ORGANISM: Homo sapiens

<400> SEQUENCE: 112
ctactgagtt tctgttatag tgttttttaa tatatatata gtattatata tatagtgtta 60
tatatatata gtgttttaga tagatagata ggtagataga tagatagata gatagataga 120
tagatagata gatagataga tatagtgaca ctctccttaa cccagatgga ctccttgtcc 180
tcactacatg ccat 194

<210> SEQ ID NO 113
<211> LENGTH: 320

-continued

<212> TYPE: DNA
<213> ORGANISM: Homo sapiens

<400> SEQUENCE: 113
cacttgaacc cgggaggtgg aggttgcact ccagcctttg caacagagca agacttcatc 60
tgaaagatag aaagatgaaa gaaagaaaga aagaaagaaa gaaagagtaa aagaaaaaaa 120
ttaaaatttt agggggaaaa ttttctaatt tttgaacatg cactaaaatg attttcagag 180
aaaaccaagt gttattttct aatctgcatg gcattattaa agatgtttac tcatcttcct 240
tggggctagg catcccattc ctgcaggaag tcttgtggtt aggcggtggc tgtggctctg 300
ggatgattca ggaatgcaga 320

<210> SEQ ID NO 114
<211> LENGTH: 330
<212> TYPE: DNA
<213> ORGANISM: Homo sapiens

<400> SEQUENCE: 114
gggatttccc tatggattgg aagtggggcg tgaaatagag gagtcagggg tcactctggg 60
gatttggcct ggagcagctg gaagatggag tggctgttaa ttcatgtagg gaaggctgtg 120
ggaagaagag gtttaggaga caaggatagc agttcattta tttatttatt tatttattta 180
tttatttatt tatttattta gagatgtagt ctcattcttt cgccaggctg gagtgcagtg 240
gcgcgatctt ggctcactgc aacctccacc tcccaggctc aagcgattct cttgcctcag 300
cctcccgagt agccaagtag ctgggactac 330

<210> SEQ ID NO 115
<211> LENGTH: 192
<212> TYPE: DNA
<213> ORGANISM: Homo sapiens

<400> SEQUENCE: 115
gccccatagg ttttgaactc acagattaaa ctgtaaccaa aataaaatta ggcatattta 60
caagctagtt tctttctttc ttttttctct ttctttcttt ctttctttct ttctttcttt 120
ctttctttct ttctttcttt ctccttcctt cctttcttcc tttctttttt gctggcaatt 180
acagacaaat ca 192

<210> SEQ ID NO 116
<211> LENGTH: 320
<212> TYPE: DNA
<213> ORGANISM: Homo sapiens

<400> SEQUENCE: 116
aggtatactt ttctctccag aatagttaga tgtaggtata ccactttgat gttgacacta 60
gtttacctag aacttatctt ctgtaaatct gtctctattt ccatctctgt ctccatcttt 120
gtctctatct ctatctgtct atctctatct atctatctat ctatctatct atctatctat 180
ctatctatct atctaaagca aattcatgcc cttctcctat ttattgaatc gagaccatag 240
acaggggtga gagaaagaat ttggcaggaa tggggatgtg tattatctgt ggcataagga 300
aactttacag aactaggttc 320

<210> SEQ ID NO 117
<211> LENGTH: 300
<212> TYPE: DNA
<213> ORGANISM: Homo sapiens -continued

<400> SEQUENCE: 117
gcccttccca ggctctagca gcagctcatg gtggggggtc ctgggcaaat agggggcaaa 60
attcaaaggg tatctgggct ctggggtgat tcccattggc ctgttcctcc cttatttccc 120
tcattcattc attcattcat tcattcattc attcattcac catggagtct gtgttccctg 180
tgacctgcac tcggaagccc tgtgtacagg ggactgtgtg ggccaggctg gataatcggg 240
agcttttcag cccacaggag gggtcttcgg tgcctccttg ggcactcaga accttgggct 300

<210> SEQ ID NO 118
<211> LENGTH: 300
<212> TYPE: DNA
<213> ORGANISM: Homo sapiens

<400> SEQUENCE: 118
agcacccaga accgtcgact ggcacagaac aggcacttag ggaaccctca ctgaatgaat 60
gaatgaatga atgaatgaat gaatgaatga atgaatgttt gggcaaataa acgctgacaa 120
ggacagaagg gcctagcggg aagggaacag gagtaagacc agcgcacagc ccgacttgtg 180
ttcagaagac ctgggattgg acctgaggag ttcaattttg gatgaatctc ttaattaacc 240
tgtgtggttc ccagttcctc ccctgagcgc ccaggacagt agagtcaacc tcacgtttga 300

<210> SEQ ID NO 119
<211> LENGTH: 143
<212> TYPE: DNA
<213> ORGANISM: Homo sapiens

<400> SEQUENCE: 119
gtgagttagc cgtttagcga tatatacata ttatgaaaca ttattattat tattattatt 60
attattatta ttattattat tattattatt tgagacggac tctcgctctg tcgcccaggc 120
tggagcgcag tggttgcgat ctg 143

<210> SEQ ID NO 120
<211> LENGTH: 279
<212> TYPE: DNA
<213> ORGANISM: Homo sapiens

<400> SEQUENCE: 120
ctattcattc aatcatacac ccatatctgt ctgtctgtct atctatctat ctatctatct 60
atctatctat ctatctgcct atctgcctgc ctacctatcc ctctatggca attgcttgca 120
accagggaga ttttattccc aggagatatt tggctatgtg tgacaacaat ttttttggtt 180
gtcacaaatg ggatgaatgt tactggcatc tggtgggtgg agcccagaga tgctgctcaa 240
caccctacag tgcacaagac agacccacca caaagaatc 279

<210> SEQ ID NO 121
<211> LENGTH: 263
<212> TYPE: DNA
<213> ORGANISM: Homo sapiens

<400> SEQUENCE: 121
tcattaatct agcttttaaa aacaactaat ttgatttcaa gtgtttgtta tttaaaagcc 60
aagaaggaaa acaaattttt ttcttgtatc accatttatt tattattatt attattatta 120
ttattattat tattattatt attattattt actaaggaat gggattggta ggtttaatga 180
tccctctgtt ttgacttctt tgagatattt ccagactact ttccactttg actgtaggaa 240

-continued tttacattgc atcaactggg tct 263

<210> SEQ ID NO 122
<211> LENGTH: 131
<212> TYPE: DNA
<213> ORGANISM: Homo sapiens

<400> SEQUENCE: 122
gtggtcttct acttgtgtca atacagatag atagatagat agatagatag atagatagat 60
agatagatag atagatagat agatatgtat gtcttttcta tgagacatac ctcatttttt 120
ggacttgagt t 131

<210> SEQ ID NO 123
<211> LENGTH: 372
<212> TYPE: DNA
<213> ORGANISM: Homo sapiens

<400> SEQUENCE: 123
catgngcccc caaagcgnag tnaacttnac ccagtgtcac aaaatggcct ttnacgaatt 60
actcctccat tgtccaccca tctnatactc actgtctgga tttcttggtt atagtaaatc 120
tagatctatc tatctatcta tctatctatc tatctatcta tctatctatc tatctgtgta 180
tctctctacc agctttttta acttgtcctt aattgttcaa tttatatata atgagaaaat 240
ggttatantt tcctgagngc ngnnttacca tagtagngca aangagttgc agcancaggg 300
ncaacattgn cacttctngg ttattccncc aatgtttncc ntttnccnta aatttnaatt 360
ttaggnggta ca 372

<210> SEQ ID NO 124
<211> LENGTH: 240
<212> TYPE: DNA
<213> ORGANISM: Homo sapiens

<400> SEQUENCE: 124
agctacagca aacttcatgt gacaaaagcc acacccataa ctttttncct ctagatagac 60
agatagatga tagatagata gatagataga tagatagata gatagataga tagatagata 120
gatatagatt ctctttctct gcattctcat ctatatttct gtctttctct taattatggg 180
taactcttag cctgccaggc taccatggaa agacaacctt tattcctctt ttctcctggc 240

<210> SEQ ID NO 125
<211> LENGTH: 325
<212> TYPE: DNA
<213> ORGANISM: Homo sapiens

<400> SEQUENCE: 125
gtgggaggaa gccagtggat ttggaaacag aaatggcttg gccttgcctg cctgcctgcc 60
tgcctgcctt ccttccttcc ttccttcctt ccttccttcc ttccttcctt ccctcctgca 120
atcctttaac ttactgaata actcattatt atgggccncc tgcaggtacc atgctaggta 180
ctagggatgt aggcatgaac actgacaagg gcctctggga ctggcattct ggtaggaaaa 240
ggggtgagac agggaagaag ccagcaaatg tatcaacaag aaacagttct aagtgctagg 300
aagaaatgaa cgtattgatg tcaca 325

<210> SEQ ID NO 126
<211> LENGTH: 269
<212> TYPE: DNA
<213> ORGANISM: Homo sapiens -continued

<400> SEQUENCE: 126
aaagctataa ttgtaccact gcactccagc ctgggcaaca gaataagatt ctgttgaagg 60
aaagaaggta ggaaggaagg aaggaaggaa ggaaggaagg aaggaaggaa ggaaggagag 120
aggtagaaag agagaagatt tttattcggg taatgggtgc accaaaatat cagaaatcac 180
tgctaaagaa cttattcatg taaccaacac cacctgttcc ttaaaaacct attgaaataa 240
anacagcnag anagagagaa agaggnnga 269

<210> SEQ ID NO 127
<211> LENGTH: 377
<212> TYPE: DNA
<213> ORGANISM: Homo sapiens

<400> SEQUENCE: 127
aaagtcttca aagcatcctg aagttggtct taagccagca ttcttaaaac tctaaggagg 60
caacaaaaga tttaaacagt gtacagcaaa tggtgactct gaaaccagag ttgtttcact 120
gctcactgcc accccgagat tgatttgcca tgatagatgg cttcctaggc tcaattaggt 180
tcttaattat ggagatagtt atatttactt ctgtcacagg gctgatgagg tgaaatattt 240
gcaaaacaat ctatctatat ctatctatat ctatctatct atctatctat ctatctatct 300
atctatctat ctatcatctt atatgtgttg ttgttgaggt tgtttgagat atcccccagg 360
ngaaacagaa atatttt 377

<210> SEQ ID NO 128
<211> LENGTH: 344
<212> TYPE: DNA
<213> ORGANISM: Homo sapiens

<400> SEQUENCE: 128
tttggactgg aacttacact gttggttctc cttgttctca gacctttgaa ctcagactga 60
aaccacatac tcagcactcc tgggtctcta gcttgccaag tgcccaagtg cagatcttgg 120
gacttctcgg tgccgttatt gtgtgagtca attccttgtt ataaaattat atatacatat 180
atttgtagat ggatagaaga tgatagatag atagataggt agatagatag atagatagat 240
agatagatag atagatagat tctgtttctc tggagaactc taatgcagtt gcccacactc 300
tttttctttt ttgtttattt cattgataac ttaccttctg aaat 344

<210> SEQ ID NO 129
<211> LENGTH: 372
<212> TYPE: DNA
<213> ORGANISM: Homo sapiens

<400> SEQUENCE: 129
aaagctacat ccaaattagg taggtagaca aataggtagg taggtagaca gacagacaga 60
ctagatagat ggacagacta gatagataga tacgtacata cataagatag atagatagat 120
agatagatag atagatagat agatagatag atagatagat agagacagat ttaaaatatt 180
tgggacattt tagtttcttt gtcactcttt gaactggaac tataaaaaat actcttttac 240
tatcacaaga ggatagagga cctaatataa tgctactgct gtgtctcaac agtgacagcc 300
aggtacaaag gttaccatta cttccctttg ggctctgagt gtgtcttgcc tgcagccacc 360
actcaccgtc ct 372

<210> SEQ ID NO 130

-continued

<211> LENGTH: 355
<212> TYPE: DNA
<213> ORGANISM: Homo sapiens

<400> SEQUENCE: 130
ttacctaaat ctgtctcaga ccatacctaa atctctctct ctctttctct ctgtctctcc 60
ctctccctct cttacagggc agttgtttat agaatatatc tcaatttgag tttgatgttt 120
ttgagagaca gaatatctat ctgtctgtct atctatccat ccatccatct atcatctatt 180
tattatctat ctatctatct atctatctat ctatctatct atctatcctg cttttctaga 240
gaacacagac taatgtaggt gataactagg atcccttccc cactaagaat ngttcagggc 300
cctgcacccc agaggaggaa cctatttcct ttctttcccc tgggatccac tgctt 355

<210> SEQ ID NO 131
<211> LENGTH: 320
<212> TYPE: DNA
<213> ORGANISM: Homo sapiens

<400> SEQUENCE: 131
taactgtaat atttgctaca acgttaataa ccaaattgtt tatgaggtgg tgtactacca 60
tatttgaaca tgtgctcaaa tattgttaaa gagacacaat taaagaaaga atgacccttg 120
gaattttatt taattttatt tatttattta tttatttatt tatttattta tttagagaca 180
gagtcttgct ctgtcgccca gcctagagtg caatggcatg atcttggctc actgcaattt 240
ttgcctcccg ggttcaagca attctccttc ctcagccttc caagtagctg ggattacagg 300
cgtgtaccac cacgcccgct 320

<210> SEQ ID NO 132
<211> LENGTH: 159
<212> TYPE: DNA
<213> ORGANISM: Homo sapiens

<400> SEQUENCE: 132
ttggagtcgc aagctgaact agcgttttct tttcttttcc tttcttttct tttcttttct 60
tttcttttct tttcttcttt tcaagacagg ttctcactct gtcactcagg ctagagtgca 120
gtggtgcaat cacggttcac tgcagcctca acttcctgg 159

<210> SEQ ID NO 133
<211> LENGTH: 229
<212> TYPE: DNA
<213> ORGANISM: Homo sapiens

<400> SEQUENCE: 133
aacaggatca atggatgcat aggtagatag atagatagat agatagatag atagatagat 60
agatagatag atagatagac agacagacag acagacagac agatgagagg ggatttatta 120
gaggaattag ctcaagtgat atggaggctg aaaaatctca tgacagtcca tctgcaagct 180
ggagacccag ggacactagg agcatggctc agtccaggtc taaaagcca 229

<210> SEQ ID NO 134
<211> LENGTH: 379
<212> TYPE: DNA
<213> ORGANISM: Homo sapiens

<400> SEQUENCE: 134
agctcaatat aacttcacag attgaacaca tccatgtaac cagcacccag attaagaaac 60
agagcatgac tagcacaatc tcatgcttcc ttttagacac tacagttgac tcttaaataa 120

-continued

```
tttggggatt aggggtgcag ttgaaaatcc aagtataatt ttgtctccct gaaaatgtaa    180

ctagtaatag cctactgttg actggaagcc ttactgactt actacataac gacacacaca    240

cacacacaca cacacacaca cacacacaca cacacacata tatatatttt gagatgcagt    300

cttgctctgt tgcccaggct ggagtncagt ggcacgatct cggctcactg caacctccgc    360

cttctgggtt caagcggtt                                                 379


<210> SEQ ID NO 135
<211> LENGTH: 387
<212> TYPE: DNA
<213> ORGANISM: Homo sapiens

<400> SEQUENCE: 135

gaattataac cgtaactgat tcatagcagc acttgccaaa ttctattttg tggaaaaata     60

ttctgggaag atattaacaa tgtnacacac acacacacac acacacacac acacacacac    120

gatgtacatg gttttaaaaa tgtcaacagg ttcctttgct ggaggaattc ccagtgtctt    180

tgttatagga atcttcactg ggaataaagt gataatagca gtggtaatgg aaatgtttta    240

ttgactgctt aaactgaagt canacaagca ttatctcact ttttttataa acattattta    300

attctcaaaa cagacctgtg cagtaggtac aattatgtgg tacacagatg agaaactgag    360

gcttacagag atgacgataa cccagct                                        387
```

DNA TYPING BY MASS SPECTROMETRY WITH POLYMORPHIC DNA REPEAT MARKERS

This application claims benefit of Provisional Application No. 60/059,415 filed Sep. 19, 1997.

The U.S. government may own rights in the present invention pursuant to Grant No. # 97-LB-VX-0003 from the U.S. National Institute of Justice and cooperative agreement # 70NANB5H1029 from the U.S. Department of Commerce.

BACKGROUND OF THE INVENTION

A. Field of the Invention

The present invention is generally directed to the field of genetic identity detection including forensic identification and paternity testing as well as genetic mapping. The present invention is more specifically directed to the use of mass spectrometry to detect length variations in DNA nucleotide sequence repeats, often referred to as short tandem repeats ("STR"), microsatellite repeats or simple sequence repeats ("SSR"). The invention is also directed to DNA sequences provided for the analysis of STR polymorphisms at specific loci on specific chromosomes.

B. Description of Related Art

Polymorphic DNA tandem repeat loci are useful DNA markers for paternity testing, human identification, and genetic mapping. Higher organisms, including plants, animals and humans, contain segments of DNA sequence with variable sequence repeats. Commonly sized repeats include dinucleotides, trinucleotides, tetranucleotides and larger. The number of repeats occurring at a particular genetic locus vary depending on the locus and the individual from a few to hundreds. The sequence and base composition of repeats can vary significantly, not even remaining constant within a particular nucleotide repeat locus. DNA nucleotide repeats are known by several different names including microsatellite repeats, simple sequence repeats, short tandem repeats and variable nucleotide tandem repeats. As used herein, the term "DNA tandem nucleotide repeat" ("DTNR") refers to all types of tandem repeat sequences.

Thousands of DTNR loci have been identified in the human genome and have been predicted to occur as frequently as once every 15 kb. Population studies have been undertaken on dozens of these STR markers as well as extensive validation studies in forensic laboratories. Specific primer sequences located in the regions flanking the DNA tandem repeat region have been used to amplify alleles from DTNR loci via the polymerase chain reaction ("PCR™"). Thus, the PCR™ products include the polymorphic repeat regions, which vary in length depending on the number of repeats or partial repeats, and the flanking regions, which are typically of constant length and sequence between samples.

The number of repeats present for a particular individual at a particular locus is described as the allele value for the locus. Because most chromosomes are present in pairs, PCR™ amplifications of a single locus commonly yields two different sized PCR™ products representing two different repeat numbers or allele values. The range of possible repeat numbers for a given locus, determined through experimental sampling of the population, is defined as the allele range, and may vary for each locus, e.g., 7 to 15 alleles. The allele PCR™ product size range (allele size range) for a given locus is defined by the placement of the two PCR™ primers relative to the repeat region and the allele range. The sequences in regions flanking each locus must be fairly conserved in order for the primers to anneal effectively and initiate PCR™ amplificattion. For purposes of genetic analysis di-, tri-, and tetranucleotide repeats in the range of 5 to 50 are typically utilized in screens.

Many different primers have been designed for various DTNR loci and reported in the literature. These primers anneal to DNA sequences outside the DNA tandem repeat region to produce PCR™ products usually in the size range of 100–800 bp. These primers were designed with polyacrylamide gel electrophoretic separation in mind, because DNA separations have traditionally been performed by slab gel or capillary electrophoresis. However, with a mass spectrometry approach to DTNR typing and analysis, examining smaller DNA oligomers is advantageous because the sensitivity of detection and mass resolution are superior with smaller DNA oligomers.

The advantages of using mass spectrometry for characterizing DTNRs include a dramatic increase in both the speed of analysis (a few seconds per sample) and the accuracy of direct mass measurements. In contrast, electrophoretic methods require significantly longer lengths of time (minutes to hours) and can only measure the size of DTNRs as a function of relative mobility to comigrating standards. Gel-based separation systems also suffer from a number of artifacts that reduce the accuracy of size measurements. These mobility artifacts are related to the specific sequences of DNA fragments and the persistence of secondary and tertiary structural elements even under highly denaturing conditions.

The inventors have performed significant work in developing time-of-flight mass spectrometry ("TOF-MS") as a means for separating and sizing DNA molecules, although other forms of mass spectrometry can be used and are within the scope of this invention. Balancing the throughput and high mass accuracy advantages of TOF-MS is the limited size range for which the accuracy and resolution necessary for characterizing DTNRs by mass spectrometry is available. Current state of the art for TOF-MS offers single nucleotide resolution up to ~100 nucleotides in size and four nucleotide resolution up to ~160 nucleotides in size. These numbers are expected to grow as new improvements are developed in the mass spectrometric field.

Existing gel-based protocols for the analysis of DTNRs do not work with TOF-MS because the allele PCR™ product size range, typically between 100 and 800 nucleotides, is outside the current resolution capabilities of TOF-MS. Application of DTNR analysis to TOF-MS requires the development of new primer sets that produce small PCR™ products 50 to 160 nucleotides in length, preferably 50 to 100 nucleotides in length. Amplified DNA may also be used to generate single stranded DNA products that are in the preferred size range for TOF-MS analysis by extending a primer in the presence of a chain termination reagent. A typical class of chain termination reagent commonly used by those of skill in the art is the dideoxynucleotide triphosphates. Again, application of DTNR analysis to TOF-MS requires that the primer be extended to generate products of 50 to 160 nucleotides in size, and preferably 50 to 100 nucleotides in length.

Gel-based systems are capable of multiplexing the analysis of 2 or more DTNR loci using two approaches. The first approach is to size partition the different PCR™ product loci. Size partitioning involves designing the PCR™ primers used to amplify different loci so that that the allele PCR™ product size range for each locus covers a different and separable part of the gel size spectrum. As an example, the PCR™ primers for Locus A might be designed so that the allele size range is from 250 to 300 nucleotides, while the primers for Locus B are designed to produce an allele size range from 340 to 410 nucleotides.

The second approach to multiplexing 2 or more DTNR loci on gel-based systems is the use of spectroscopic partitioning. Current state of the art for gel-based systems involves the use of fluorescent dyes as specific spectroscopic markers for different PCR™ amplified loci. Different chromophores that emit light at different color wavelengths provide the means for differential detection of two different PCR™ products even if they are exactly the same size, thus 2 or more loci can produce PCR™ products with allele size ranges that overlap. For example, Locus A with a green fluorescent tag produces an allele size range from 250 to 300 nucleotides, while Locus B with a red fluorescent tag produces an allele size range of 270 to 330 nucleotides. A scanning, laser-excited fluorescence detection device monitors the wavelength of emissions and assigns different PCR™ product sizes, and their corresponding allele values, to their specific loci based on their fluorescent color.

In contrast, mass spectrometry directly detects the molecule preventing the use of optical spectroscopic partitioning as a means for multiplexing. While it is possible to have a limited use of size partitioning with TOF-MS, the limited size range of high-resolution detection by TOF-MS makes it likely that only 2 different loci can be multiplexed and size partitioned. In many cases, it may not be possible to even multiplex 2 loci and maintain a partitioning of the 2 different allele size ranges. Therefore, new methods are needed in order to employ mass spectrometry for the analysis of multiplexed DTNRs.

SUMMARY OF THE INVENTION

It is, therefore, a goal of the present invention to provide newly designed PCR™ primers which are closer to the repeat regions then have previously been employed providing for the efficient analysis by TOF-MS. Specifically, the invention provides oligonucleotide primers designed to characterize various DTNR markers useful for human identity testing. The primers are for use in PCR™ amplification schemes, however, one of skill in the art could, in light of the present disclosure, employ them to generate appropriate size nucleic acid products for TOF-MS analysis using other methods of extending one or more of the disclosed primers. Additionally, these primers and their extension products are suitable for detection by mass spectrometry. Thus, applications of this invention include forensic and paternity testing and genetic mapping studies.

An embodiment of the present invention encompasses an oligonucleotide primer for use in analyzing alleles of a DNA tandem nucleotide repeat at a DNA tandem nucleotide repeat locus by mass spectrometry, which includes a nucleotide sequence that contains a flanking region of the locus where the primer upon extension generates a product that is capable of being analyzed by mass spectrometry. Preferably, the oligonucleotide primer's 3' end will be complementary to a region flanking a DNA tandem repeat region immediately adjacent to the DNA tandem repeat region or may further extend up to one, two, three, four or five tandem repeats into the DNA tandem repeat region. Used in this context "immediately adjacent" or "immediately flanking" means one, two, three, or four nucleotides away from the DNA tandem repeat region of the DNA tandem repeat locus.

The oligonucleotide primers of this invention are designed to generate extension products amenable to mass spectral analysis and containing a DTNR sequence, or region of interest, for which one is interested in determining the mass. The "flanking" regions of a DTNR locus are the portions of DNA sequence on either side of the DTNR region of interest. For embodiments employing PCR™ primers and polymerases to amplify a DTNR sequence, the primers are sufficiently complementary to a portion of one or more flanking regions of the DTNR locus to allow the primer to effectively anneal to the target nucleic acid and provide a site to extend a complement to the target nucleic acid via PCR™. For embodiments employing primer extension, a preferred method is to use a single primer that is sufficiently complementary to allow effective anealling to a portion of a target DTNR locus flanking region in conjunction with a chain termination reagent. The chain termination reagent allows the production of discreet limited size nucleic acid products for mass spectral analysis. Preferred chain termination reagent for use in the present invention are dideoxynucleotide triphosphates. Therefore, for the methods comprising any type of primer extension, it is preferred that at least one of the primers is sufficiently complementary to a portion of a flanking region that is preferably adjacent to or close to the DTNR region of interest, generally within about 40 nucleotides of the DNA tandem nucleotide repeat region. As used in this context, "about" means anywhere from ±1 to 40 nucleotides, and all the integers in between, for example, ±1, ±2, ±3, ±4, ±5, ±6, ±7, ±8, ±9, ±10, etc. nucleotides.

The primer extension products are preferably single-stranded and may be any size that can be adequately resolved by mass spectrometric analysis. Preferably, detected, the final product single-stranded target nucleic acids are less than about 160 or 150 bases in length. More preferably, the extended nucleic acid products are from about 10 to 100 or 120 bases in length. As used in this context, "about" means anywhere from ±1 to 20 bases, and all the integers in between, for example, ±1, ±2, ±3, ±4, ±5, ±6, ±7, ±8, ±9, ±10, etc. bases.

As used herein "a" will be understood to mean one or more. Thus, "a DNA tandem repeat marker" may refer, for example, to one, two, three, four, five or more DNA tandem repeat markers.

The present invention is also directed to new oligonucleotide primers which have been designed to match a portion of the flanking regions for various DTNR loci. Specific embodiments of this invention include oligonucleotide primers designed to amplify the following DTNR loci: CSF1PO, D3S1358, D5S818, D7S820, D8S1179, D13S317, D16S539, D18S51, D21S11, DYS19, F13A1, FES/FPS, FGA, HPRTB, TH01, TPOX, DYS388, DYS391, DYS392, DYS393, D2S1391, D18S535, D2S1338, D19S433, D6S477, D1S518, D14S306, D22S684, F13B, CD4, D12S391, D10S220 and D7S523. With the exception of D3 S1358, sequences for the STR loci of this invention are accessible to the general public through GenBank using the accession numbers listed in Table 1. These oligonucleotide primers may preferably contain a cleavable site, such as a recognition site for Type II and IIS restriction endonucleases, an exonuclease blocking site, or a chemically cleavable site, for reducing the length of the amplified product and increasing the mass spectral resolution.

Examples of some oligonucleotide primers that may be employed for amplifying these loci are listed in SEQ ID NO:1 through SEQ ID NO:103. Preferred oligonucleotide primers that also contain a cleavable phosphorothioate linkage and biotin moiety for immobilization on an avidin, streptavidin solid support are sequences according to SEQ ID NO:2, SEQ ID NO:4, SEQ ID NO:5, SEQ ID NO:7, SEQ ID NO:9, SEQ ID NO:11, SEQ ID NO:14, SEQ ID NO:16, SEQ ID NO:17, SEQ ID NO:19, SEQ ID NO:21, SEQ ID NO:23, SEQ ID NO:25, SEQ ID NO:27, SEQ ID NO:30, SEQ ID NO:31, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100 and SEQ ID NO:103. These newly designed primers generate nucleic acid extension products which are smaller than those used previously with electrophoresis separation methods. Additionally, these primers may be used in other methods of primer extension known to those of skill in the art.

It will be apparent to one skilled in the art that some variations of these primers will also serve effectively, for example, adding or deleting one or a few bases from the primer and/or shifting the position of the primer relative to the DTNR sequence by one or a few bases. Thus, primers encompassed by the present invention include the primers specifically listed as well as modifications of these primers. Although these sequences are all biotinylated at the 5' end and contain a phosphorothioate linkage at a particular location, one of skill in the art would recognize that similar primers having biotin moieties and the cleavable groups at other sites would also be encompassed by the present invention. Primers containing types of immobilization attachments sites other than biotin, for example, would also be encompassed. Typically, the placement of the cleavable group is not critical as long as it is close enough to the 3' end to cleave the cleave the nucleic acid extension product to a reduced-length amplified product that is amenable to mass spectral analysis. These primers in pairs may also be combined to generate overlapping PCR™ product sizes which are all distinguishable by mass. However, for embodiments multiplexing multiple DTNR loci with overlapping allelic mass ranges, strategic placement of the cleavable group may effect a separation or an interleaving of mass spectral peaks.

Another embodiment of this invention encompasses a kit for analyzing alleles of a DTNR locus in a target nucleic acid, having a first strand and a second complementary strand, by mass spectrometry which includes a first primer complementary to the flanking region of a DNA tandem nucleotide repeat region and a second primer complementary to the opposite flanking region of a DNA tandem nucleotide repeat region. Preferred kits of this invention are kits for analyzing the following DTNR loci: CSF1PO, D3S1358, D5S818, D7S820, D8S1179, D13S317, D16S539, D18S51, D21S11, DYS19, F13A1, FES/FPS, FGA, HPRTB, TH01, TPOX, DYS388, DYS391, DYS392, DYS393, D2S1391, D18S535, D2S1338, D19S433, D6S477, D1S518, D14S306, D22S684, F13B, CD4, D12S391, D10S220 and D7S523.

Another embodiment of this invention encompasses a kit for analyzing alleles of a multiple DTNR loci in a target nucleic acid by mass spectrometry, which includes a plurality of primers complementary to the flanking regions of DNA tandem nucleotide repeat regions. Preferred kits of this invention are kits for analyzing the following DTNR loci: CSF1PO, D3S1358, D5S818, D7S820, D8S1179, D13S317, D16S539, D18S51, D21S11, DYS19, F13A1, FES/FPS, FGA, HPRTB, TH01, TPOX, DYS388, DYS391, DYS392, DYS393, D2S1391, D18S535, D2S1338, D19S433, D6S477, D1S518, D14S306, D22S684, F13B, CD4, D12S391, D10S220 and D7S523.

The primers employed with these kits may preferably have cleavable sites, such as a recognition site for a restriction endonuclease, an exonuclease blocking site, or a chemically cleavable site. Preferred chemically cleavable sites encompass modified bases, modified sugars (e.g., ribose), and chemically cleavable groups incorporated into the phosphate backbone, such as dialkoxysilane, 3'-(S)-phosphorothioate, 5'-(S)-phosphorothioate, 3'-(N)-phosphoroamidate, or 5'-(N)-phosphoroamidate linkages. Another preferred embodiment is a kit employing a first primer that is capable of attaching to a solid support.

For primer extension by PCR amplification, it is preferable to employ these primers in pairs. Preferred pairs of primers include the following: a sequence according to SEQ ID NO:1 and a sequence according to SEQ ID NO:2; a sequence according to SEQ ID NO:3 and a sequence according to SEQ ID NO:4; a sequence according to SEQ ID NO:5 and a sequence according to SEQ ID NO:6; a sequence according to SEQ ID NO:7 and a sequence according to SEQ ID NO:8; a sequence according to SEQ ID NO:9 and a sequence according to SEQ ID NO:10; a sequence according to SEQ ID NO:11 and a sequence according to SEQ ID NO:12; a sequence according to SEQ ID NO:13 and a sequence according to SEQ ID NO:14; a sequence according to SEQ ID NO:15 and a sequence according to SEQ ID NO:16; a sequence according to SEQ ID NO:17 and a sequence according to SEQ ID NO:18; a sequence according to SEQ ID NO:19 and a sequence according to SEQ ID NO:20; a sequence according to SEQ ID NO:21 and a sequence according to SEQ ID NO:22; a sequence according to SEQ ID NO:23 and a sequence according to SEQ ID NO:24; a sequence according to SEQ ID NO:25 and a sequence according to SEQ ID NO:26; a sequence according to SEQ ID NO:27 and a sequence according to SEQ ID NO:28; a sequence according to SEQ ID NO:29 and a sequence according to SEQ ID NO:30; a sequence according to SEQ ID NO:31 and a sequence according to SEQ ID NO:32; a sequence according to SEQ ID NO:49 and a sequence according to SEQ ID NO:83; a sequence according to SEQ ID NO:52 and a sequence according to SEQ ID NO:84; a sequence according to SEQ ID NO:54 and a sequence according to SEQ ID NO:85; a sequence according to SEQ ID NO:56 and a sequence according to SEQ ID NO:86; a sequence according to SEQ ID NO:58 and a sequence according to SEQ ID NO:87; a sequence according to SEQ ID NO:59 and a sequence according to SEQ ID NO:88; a sequence according to SEQ ID NO:62 and a sequence according to SEQ ID NO:89; a sequence according to SEQ ID NO:63 and a sequence according to SEQ ID NO:90; a sequence according to SEQ ID NO:66 and a sequence according to SEQ ID NO:91; a sequence according to SEQ ID NO:67 and a sequence according to SEQ ID NO:92; a sequence according to SEQ ID NO:70 and a sequence according to SEQ ID NO:93; a sequence according to SEQ ID NO:72 and a sequence according to SEQ ID NO:94; a sequence according to SEQ ID NO:74 and a sequence according to SEQ ID NO:95; a sequence according to SEQ ID NO:76 and a sequence according to SEQ ID NO:96; a sequence according to SEQ ID NO:78 and a sequence according to SEQ ID NO:97; a sequence according to SEQ ID NO:80 and a sequence according to SEQ ID NO:98; a sequence according to SEQ ID NO:66 and a sequence according to SEQ ID NO:99; a sequence according to SEQ ID NO:33 and a sequence according to SEQ ID NO:100; and a sequence according to SEQ ID NO:101 and a sequence according to SEQ ID NO:103.

In one embodiment, at least one of the primers used to prepare the nucleic acid extension product contains a surface binding moiety, such as a biotin moiety, at the 5'-end and a cleavable moiety, such as a phosphorothioate linkage (see FIGS. 7A and 7B), near the 3'-end for a capture and release assay, such as one using streptavidin-coated magnetic beads for binding biotinylated primers, described in PCT Patent Application No. WO 96/37630, and incorporated herein by reference. These linkages are often referred as thiophosphate linkages as well. Incorporation of a method for obtaining single-stranded PCR™ products, such as is possible with the primer modifications described above, is preferred. Removal of one of the two strands halves the number of DNA oligomers that will be visualized by TOF-MS and improves the likelihood of resolving all PCR™ product strands.

Another embodiment of this invention encompasses a method for analyzing DNA tandem nucleotide repeat alleles at a DNA tandem nucleotide repeat locus in a target nucleic acid by mass spectrometry which includes the steps of a) obtaining a target nucleic acid containing a DNA tandem nucleotide repeat region; b) extending the target nucleic acid using one or more primers to obtain a limited size range of nucleic acid extension products, wherein the primers are complementary to a sequence flanking the DNA tandem nucleotide repeat of said locus; and c) determining the mass of the nucleic acid extension products by mass spectrometry, where the target nucleic acid is normally double-stranded (i.e. it has a first strand and a second complementary strand). Nucleic acid extension products may be generated in this method by any means known to those of skill in the art, and particularly either by amplification, such as PCR amplification, or by primer extension in conjunction with a chain termination reagent. Preferred primers may immediately flank the DNA tandem repeat locus, or may further extend up to one, two, three, four or five tandem repeats into the DNA tandem repeat region. Used in this context "immediately adjacent" or "immediately flanking" means one, two, three, or four nucleotides away from the DNA tandem repeat region of the DNA tandem repeat locus. Preferred primers may contain a cleavable site, such as a recognition site for a restriction endonuclease, an exonuclease blocking site, or a chemically cleavable site, and be capable of attaching to a solid support.

These primers may be capable of directly or indirectly attaching to a solid support via covalent or noncovalent binding. The primers may contain an immobilization attachment site (IAS) for attachment to a solid support. This site is usually upstream of the chemically cleavable site. A suitable immobilization attachment site is any site capable of being attached to a group on a solid support. These sites may be a substituent on a base or sugar of the primer. An IAS may be, for example, an antigen, biotin, or digoxigenin. This attachment allows for isolation of only one strand of an amplified product. Such isolation of either single-stranded or double-stranded amplified target nucleic acids generally occurs prior to the application of the nucleic acids to the matrix solution, resulting in well-defined mass spectral peaks and enhanced mass accuracy. The matrix solution can be any of the known matrix solutions used for mass spectrometric analysis, including 3-hydroxypicolinic acid ("3-HPA"), nicotinic acid, picolinic acid, 2,5-dihydroxybenzoic acid, and nitrophenol.

For example, in one embodiment, a strand of a target nucleic acid extension product may be bound or attached to a solid support to permit rigorous washing and concomitant removal of salt adducts, unwanted oligonucleotides and enzymes. Either a double-stranded or a single-stranded nucleic acid extension product may be isolated for mass spectrometric analysis. The single-stranded target nucleic acid extension product analyzed by MS may be either the strand bound or not bound to the solid support.

When an unbound strand is used for MS analysis, it is typically purified by first washing the bound strand and its attached complement under conditions not sufficiently rigorous to disrupt the strand's attachment to its bound complement. After unwanted biomolecules and salts are removed, the complement may then be released under more rigorous conditions. In contrast, when the bound strand is to be analyzed, it is typically washed under more vigorous conditions such that the interactions between the bound strand, if present, and its unbound complement is disrupted. This allows the unbound strand to be washed away with the other salts and unwanted biomolecules. Cleavable linkers or cleavable primers may be used to release the bound strand from the solid support prior to MS analysis.

Preferred primers for practicing this method include primers designed to amplify DTNR loci selected from the group consisting of CSF1PO, D3S1358, D5S818, D7S820, D8S1179, D13S317, D16S539, D18S51, D21S11, DYS19, F13A1, FES/FPS, FGA, HPRTB, TH01, TPOX, DYS388, DYS391, DYS392, DYS393, D2S1391, D18S535, D2S1338, D19S433, D6S477, D1S518, D14S306, D22S684, F13B, CD4, D12S391, D10S220 and D7S523. Preferred pairs of primers designed to amplify these loci include: a sequence according to SEQ ID NO:1 and a sequence according to SEQ ID NO:2; a sequence according to SEQ ID NO:3 and a sequence according to SEQ ID NO:4; a sequence according to SEQ ID NO:5 and a sequence according to SEQ ID NO:6; a sequence according to SEQ ID NO:7 and a sequence according to SEQ ID NO:8; a sequence according to SEQ ID NO:9 and a sequence according to SEQ ID NO:10; a sequence according to SEQ ID NO:11 and a sequence according to SEQ ID NO:12; a sequence according to SEQ ID NO:13 and a sequence according to SEQ ID NO:14; a sequence according to SEQ ID NO:15 and a sequence according to SEQ ID NO:16; a sequence according to SEQ ID NO:17 and a sequence according to SEQ ID NO:18; a sequence according to SEQ ID NO:19 and a sequence according to SEQ ID NO:20; a sequence according to SEQ ID NO:21 and a sequence according to SEQ ID NO:22; a sequence according to SEQ ID NO:23 and a sequence according to SEQ ID NO:24; a sequence according to SEQ ID NO:25 and a sequence according to SEQ ID NO:26; a sequence according to SEQ ID NO:27 and a sequence according to SEQ ID NO:28; a sequence according to SEQ ID NO:29 and a sequence according to SEQ ID NO:30; a sequence according to SEQ ID NO:31 and a sequence according to SEQ ID NO:32; a sequence according to SEQ ID NO:49 and a sequence according to SEQ ID NO:83; a sequence according to SEQ ID NO:52 and a sequence according to SEQ ID NO:84; a sequence according to SEQ ID NO:54 and a sequence according to SEQ ID NO:85; a sequence according to SEQ ID NO:56 and a sequence according to SEQ ID NO:86; a sequence according to SEQ ID NO:58 and a sequence according to SEQ ID NO:87; a sequence according to SEQ ID NO:59 and a sequence according to SEQ ID NO:88; a sequence according to SEQ ID NO:62 and a sequence according to SEQ ID NO:89; a sequence according to SEQ ID NO:63 and a sequence according to SEQ ID NO:90; a sequence according to SEQ ID NO:66 and a sequence according to SEQ ID NO:91; a sequence according to SEQ ID NO:67 and a sequence according to SEQ ID NO:92; a sequence according to SEQ ID NO:70 and a sequence according to SEQ ID NO:93; a sequence according to SEQ ID NO:72 and a sequence according to SEQ ID NO:94; a sequence according to SEQ ID NO:74 and a sequence according to SEQ ID NO:95; a sequence according to SEQ ID NO:76 and a sequence according to SEQ ID NO:96; a sequence according to SEQ ID NO:78 and a sequence according to SEQ ID NO:97; a sequence according to SEQ ID NO:80 and a sequence according to SEQ ID NO:98; a sequence according to SEQ ID NO:66 and a sequence according to SEQ ID NO:99; a sequence according to SEQ ID NO:33 and a sequence according to SEQ ID NO:100; and a sequence according to SEQ ID NO:101 and a sequence according to SEQ ID NO:103.

The present invention also focuses on an improved method of multiplexing the analysis of nucleic acid extension products derived from DNA nucleotide repeat loci. This method differs from known methods of multiplexing DTNR analysis in that mass spectrometry is employed and the range of possible nucleic acid extension products for the multiplexed loci, the allele nucleic acid extension product size ranges, may be specifically chosen to overlap in the mass scale yet be uniquely resolved and detected.

Thus, this invention encompasses methods for analyzing more than one target nucleic acid in which the target nucleic acids are used to produce more than one nucleic acid product extension product and where each nucleic acid extension product may comprise a different DTNR sequence. A preferred embodiment encompasses simultaneously determining the mass of more than one DNA tandem nucleotide repeat allele at more than one DNA tandem nucleotide repeat loci. According to this embodiment several amplification products containing various DTNR sequences from different DTNR loci may be analyzed in the same solution and spectrum.

Additionally, the DNA tandem nucleotide repeat loci may have overlapping allelic mass ranges (see FIGS. 4 and 5). The term "overlapping allelic mass ranges" is defined to mean that the alleles that may be present for a particular DTNR locus have masses that overlap, or coincide, as observed by mass spectrometry with the masses for alleles from another DTNR locus. The methods of the present invention allow one to resolve these alleles by mass spectrometry either by increasing the mass separation of these peaks or by modifying the mass of the amplified products containing the various DTNR sequences such that the amplification products have interleaving mass spectral peaks (see FIG. 6).

This novel interleaved multiplexing approach overcomes the TOF-MS limitations for size partitioning and takes advantage of the high mass accuracy of the method within the high resolution mass range below about 160 nucleotides in size. One specific embodiment encompasses a method that involves the design of specific primer or primers that produce nucleic acid extension products for a first locus with defined allele mass values. The primer or primers for second locus are then selected so that while the mass range for the predicted nucleic acid extension products of the primers overlap with the mass range for the products of the first locus, the specific predicted nucleic acid extension product mass values differ from those of the first locus and therefore can be uniquely resolved by TOF-MS. Further loci may be added to the multiplex using the same method such that three, four, five, six, seven, eight, nine, ten or more loci may be analyzed simultaneously.

The basic limits for this multiplexing are defined by the ability to resolve all possible nucleic acid extension products within a mixture. It is not inconceivable that as many as 10 different loci might be interleaved and uniquely resolved. In addition to multiplexing two or more DTNRs it is also possible to use this invention to interleave mixtures of DTNRs with specific nucleic acid extension products arising from nonrepeat loci, e.g., a DTNR locus with allelic nucleic acid extension products 72, 76, 80, 84 and 88 nucleotides in size could be simultaneously analyzed with a nucleic acid extension product 82 nucleotides in size.

The ability to interleave loci requires that thenucleic acid extension product mass values for all possible allele values should preferably be known. These allele mass values may be determined empirically or more likely by calculation using the known loci sequences. In many cases it may be necessary to "fine tune" the allele mass values for one or more loci in a multiplexed mixture in order to prevent unresolvable overlap between two Nucleic acid extension products. For example, allele 5 for Locus A may be only 5 Da different in mass than allele 9 for Locus B preventing resolution of those two Nucleic acid extension products by mass spectrometry. Mass modifications to one or both loci may be used to increase this mass difference to 100 Da.

Adjusting the allele mass values for any given locus may be done by any number of methods including: increasing or decreasing the size the of the nucleic acid extension products via altered sequences and placement of the primers; addition of nonhybridizing nucleotides to the 5' ends of one or more primers, addition of nonnucleotide chemical modifications internally or to the ends of one or both primers; alterations in base composition within one or both primers, including the use of nonstandard nucleotides, that may or may not result in mismatches within the primers; incorporation of and specific placement of a chemically cleavable moiety within the primer backbone to reduce the length of the nucleic acid extension product by a selected amount; enzymatic cleavage of the nucleic acid extension products using a restriction endonuclease that recognizes a restriction site within one or both primers or within the nucleic acid extension product itself; use of a 5' to 3' exonuclease in concert with exonuclease blocking modified nucleotides contained within one or more primers; incorporation of nonstandard deoxyribonucleotides or chemically or isotopically modified nucleotides during polymerization; any number of methods of mass modifying by addition of chemical moieties post amplification; by using different chain termination reagents in conjunction with primer extension; or any number of other means that anyone skilled in the art would be able to identify.

Another embodiment encompasses a method of multiplexing amplification products containing DTNRs having overlapping allelic ranges where at least one amplification product contains a mass modified nucleotide. Mass modified nucleotides include nucleotides to which nonnucleotide moieties have been chemically attached; bases having altered compositions; nonstandard nucleotides, that may or may not result in mismatches within the primers; and any bases whose masses have been modified through the addition of chemical moieties after the amplification step.

Alternatively, the length of at least one extension product may be reduced by cleaving the extension product at a cleavable site such as a restriction endonuclease cleavage site, an exonuclease blocking site, or a chemically cleavable site. Preferred chemically cleavable sites for multiplexing include modified bases, modified sugars (e.g., ribose), or a chemically cleavable group incorporated into the phosphate backbone, such as a dialkoxysilane, 3'-(S)-phosphorothioate, 5'-(S)-phosphorothioate, 3'-(N)-phosphoroamidate, or 5'-(N)-phosphoroamidate. Preferred primers may also be capable of attaching to a solid support.

Another embodiment of this invention encompasses a method for multiplexing the detection of more than one amplified DNA tandem nucleotide repeat marker from more than one DNA tandem nucleotide repeat loci including: determining the mass of more than one nucleic acid extension product by mass spectrometry, where the DNA tandem nucleotide repeat loci each comprise a DNA tandem repeat sequence and a flanking sequence and have overlapping allelic mass ranges. Typically, at least one of the target nucleic acid extension products may contain a mass modifying group.

"Mass modifying groups" may comprise any group that alters the mass of the amplified products to produce interleaving or otherwise resolvable mass spectral peaks. These groups, which may be incorporated during or after primer extension, may be mass modified nucleotides, nonstandard deoxyribonucleotides, or even cleavable sites as cleaving such a site modifies the mass by reducing the length of the extension product. As used in this context, modified or nonstandard bases are generally understood to include bases not found in DTNR locus flanking the DTNR sequence of the sample or target nucleic acid.

BRIEF DESCRIPTION OF THE DRAWINGS

FIG. 31 displays the mass spectrum for the D21S11 locus.

DESCRIPTION OF ILLUSTRATIVE EMBODIMENTS

Figure 1:
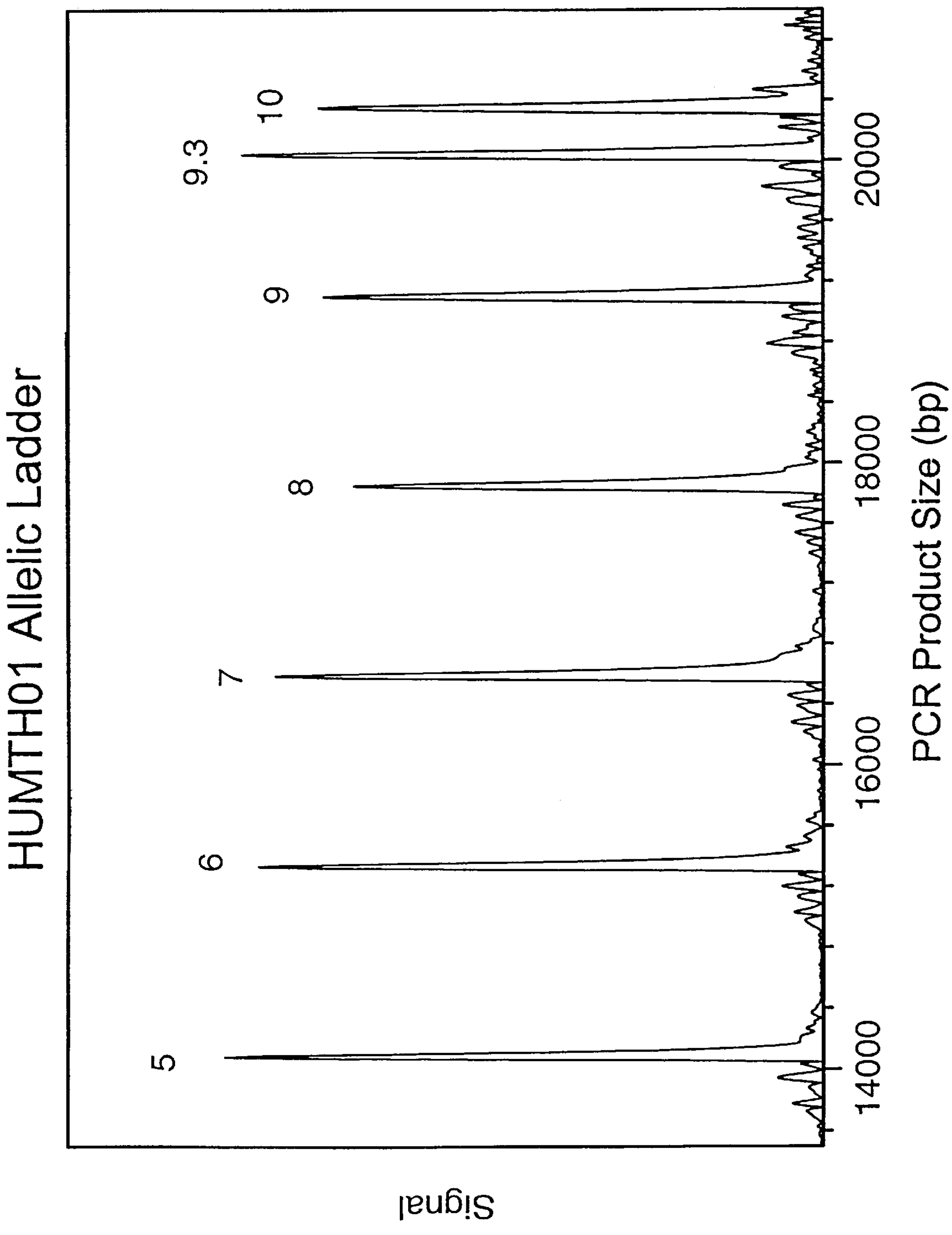
FIG. 1 is a mass spectrum of an allelic ladder from the tyrosine hydroxylase gene ("TH01"). Most of the common alleles for this STR marker (alleles 5, 6, 7, 8, 9, 9.3, and 10) can be seen. Alleles 9.3 and 10 differ by a single nucleotide while the other alleles are separated by four bases.
Figure 2:
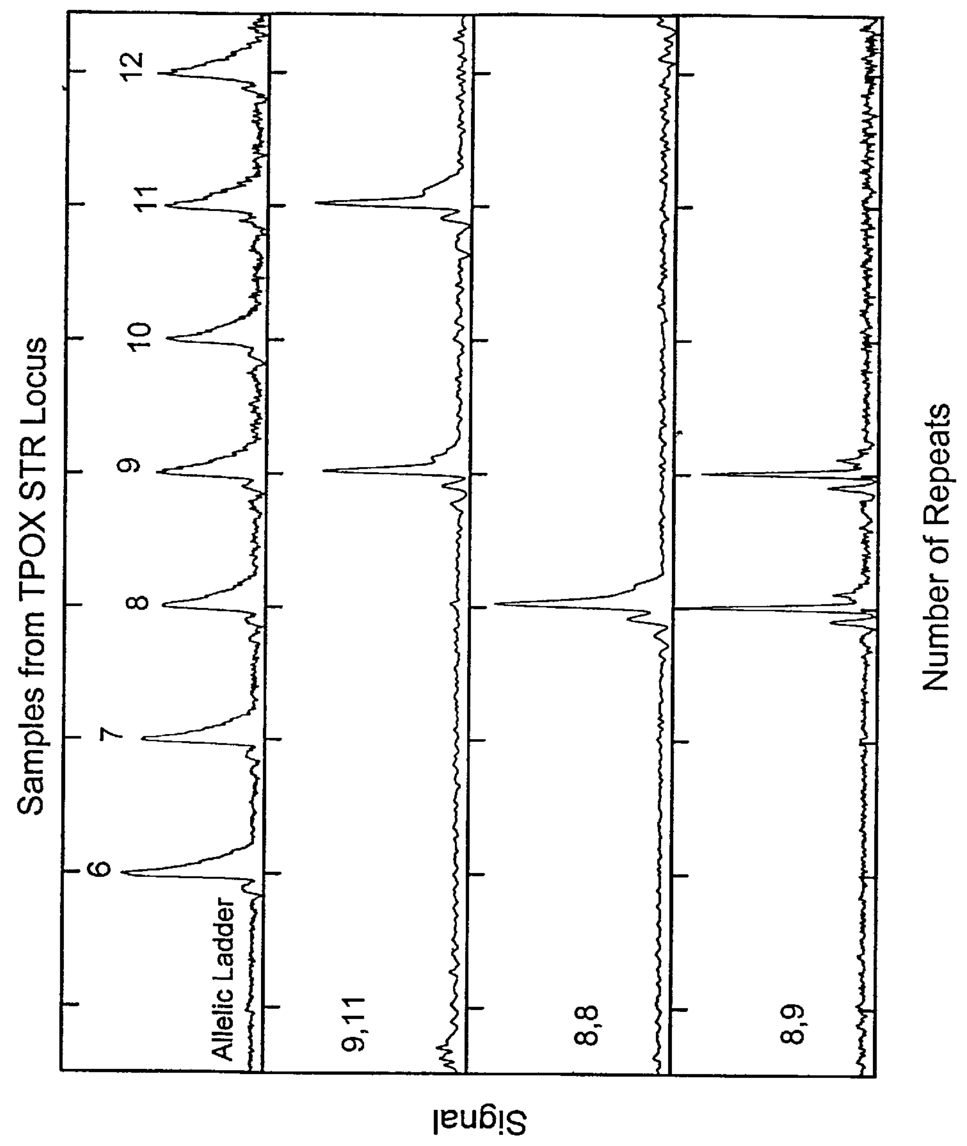
FIG. 2 displays mass spectra for several samples from the TPOX locus. The top spectrum is an allelic ladder containing alleles ranging from 6 to 13 repeats while the other spectra show the isolation of various alleles for this locus.

The present invention focuses on a mass spectrometric method of multiplexing the analysis of Nucleic acid extension products which overlap in mass derived from DNA nucleotide repeat loci. For example, to resolve all possible alleles of the DTNRs being analyzed the masses of the Nucleic acid extension products from two or more DTNR markers may be offset from one another so that any two possible alleles (or any two possible common alleles) do not overlap in mass within the mass resolution of the mass spectrometer, yet the ranges of the possible alleles do overlap. Within the overlapping mass range, defined as the mass range held is common by two loci with defined allele size ranges, the DTNR marker may be offset from one another by some fraction of the mass of the sequence repeat unit, e.g. for tetranucleotide DTNR markers mass offsets less than four nucleotide, for dinucleotide DTNRs mass offsets less than 2 nucleotides. Other types of offset, such as may be found when multiplexing dinucleotide repeat loci with tetranucleotide or complex nucleotide repeat loci, will be apparent to one skilled in the art.

This approach overcomes the TOF-MS limitations for size partitioning, where the PCR™ product for the allele range of two or more sets of possible loci do not overlap, by taking advantage of the high mass accuracy associated with mass spectroscopy within the high resolution mass range (below ~160 nucleotides in size). Although this method is currently most useful for oligonucleotides below ~160 nucleotides, this size is a function of the number of nucleotides in the repeat as well as the resolution of the mass spectroscopic method. Therefore, larger oligonucleotides are also useful with the present invention, particularly where larger repeat sequences (tetra- vs. dinucleotides) or as advances in mass spectroscopy allow for greater mass resolution in higher mass ranges.

This multiplexing method involves the design of specific primers that produce Nucleic acid extension products for a first locus with defined allele mass values. The primers for the second locus are then chosen so that while the mass range for the different alleles overlaps with the mass range for the first locus, the specific allele mass values differ from those of the first locus and therefore can be uniquely resolved by TOF-MS. The identity of each allele, defined by the specific Nucleic acid extension products being characterized, is uniquely determined using the high accuracy molecular mass values provided by TOF-MS. In contrast, gel-based methods are not capable of providing accurate mass values for uniquely identifying each product within a multiplexed, allelically interleaved mixture of Nucleic acid extension products. The basic limits for this multiplexing method are defined by the ability to resolve all possible, or all common, Nucleic acid extension products within a mixture. Potentially as many as 10 different loci might be interleaved and fully resolved.

The invention further relates to primers designed to characterize 33 DNA repeat markers useful for human identity testing. Applications include forensic and paternity testing as well as genetic mapping studies. These DTNR markers are useful in PCR™ amplification, preferably as pairs of oligonucleotide primers, and in other methods of primer extension may be used as single primers, the extension products of which may be accurately detected by mass spectrometry as they are smaller than those used previously with electrophoresis separation methods.

Figure 3A:
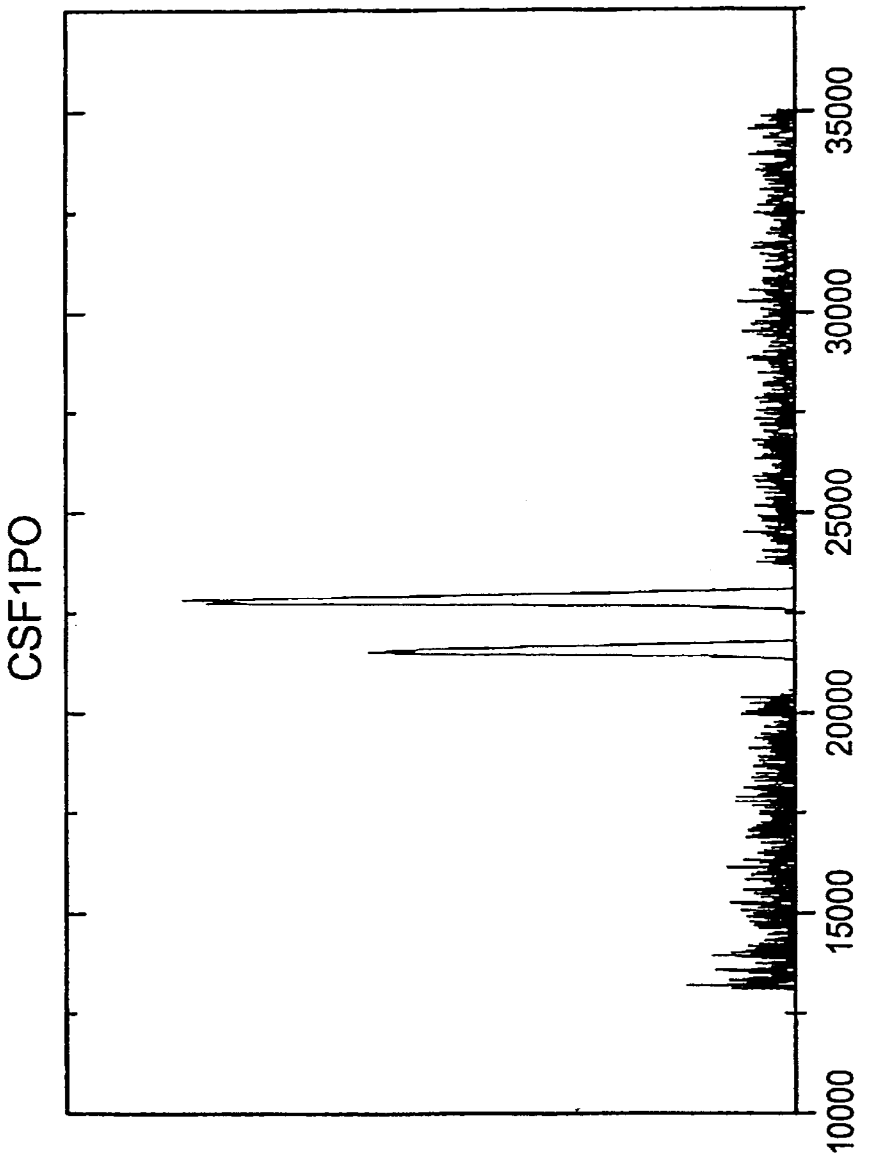
FIG. 3A displays the mass spectrum for the CSF1PO locus.
Figure 3B:
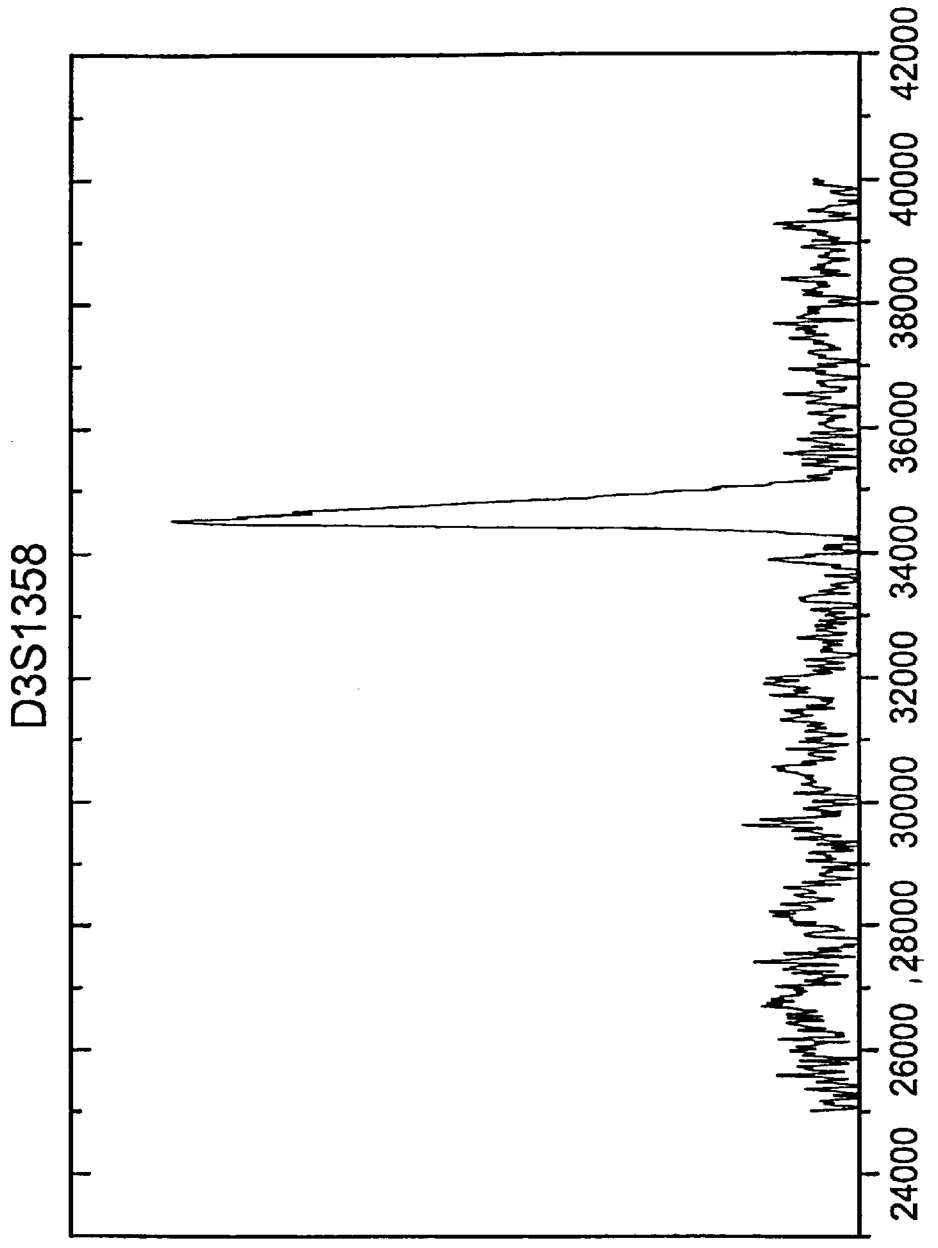
FIG. 3B displays the mass spectrum for the D3S1358 locus.
Figure 3C:
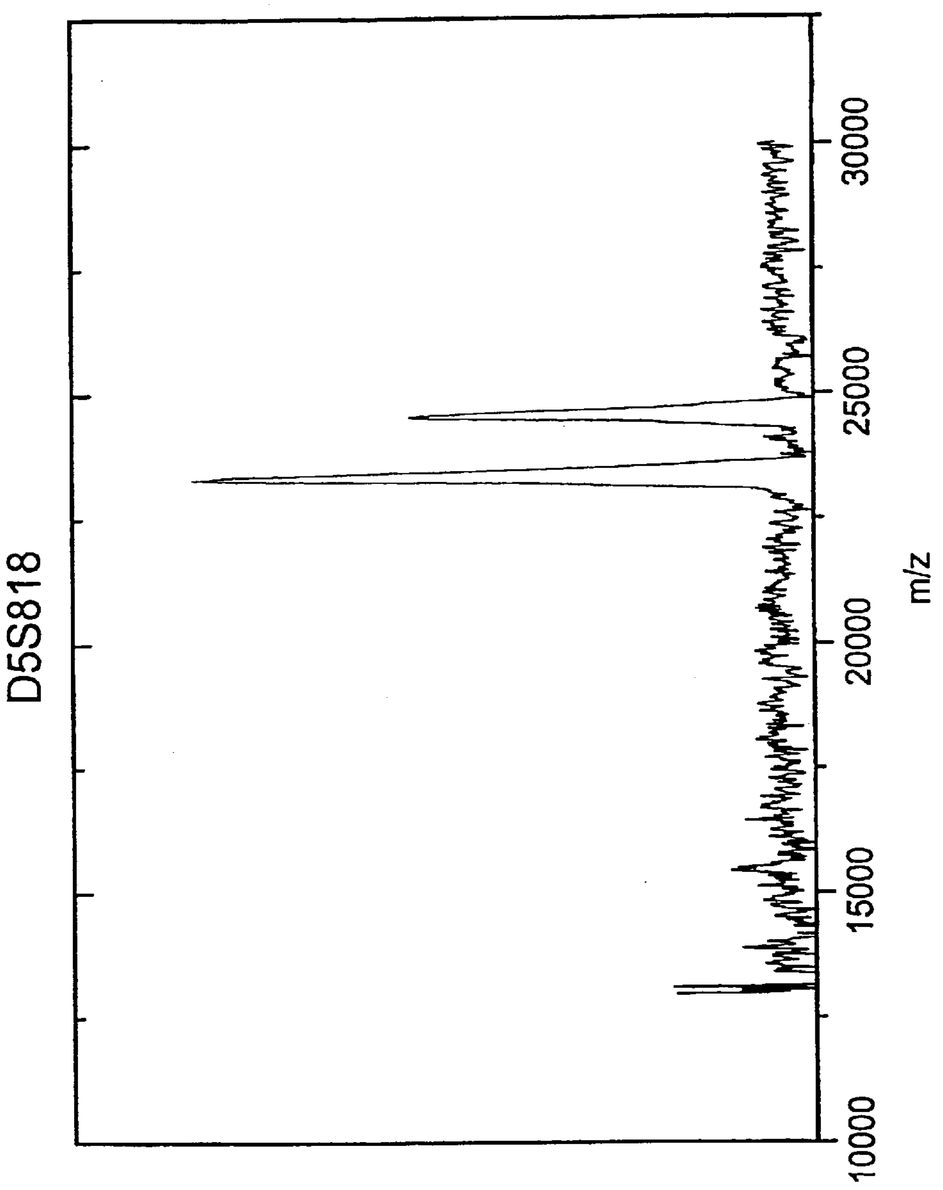
FIG. 3C displays the mass spectrum for the D5S818 locus.
Figure 3D:
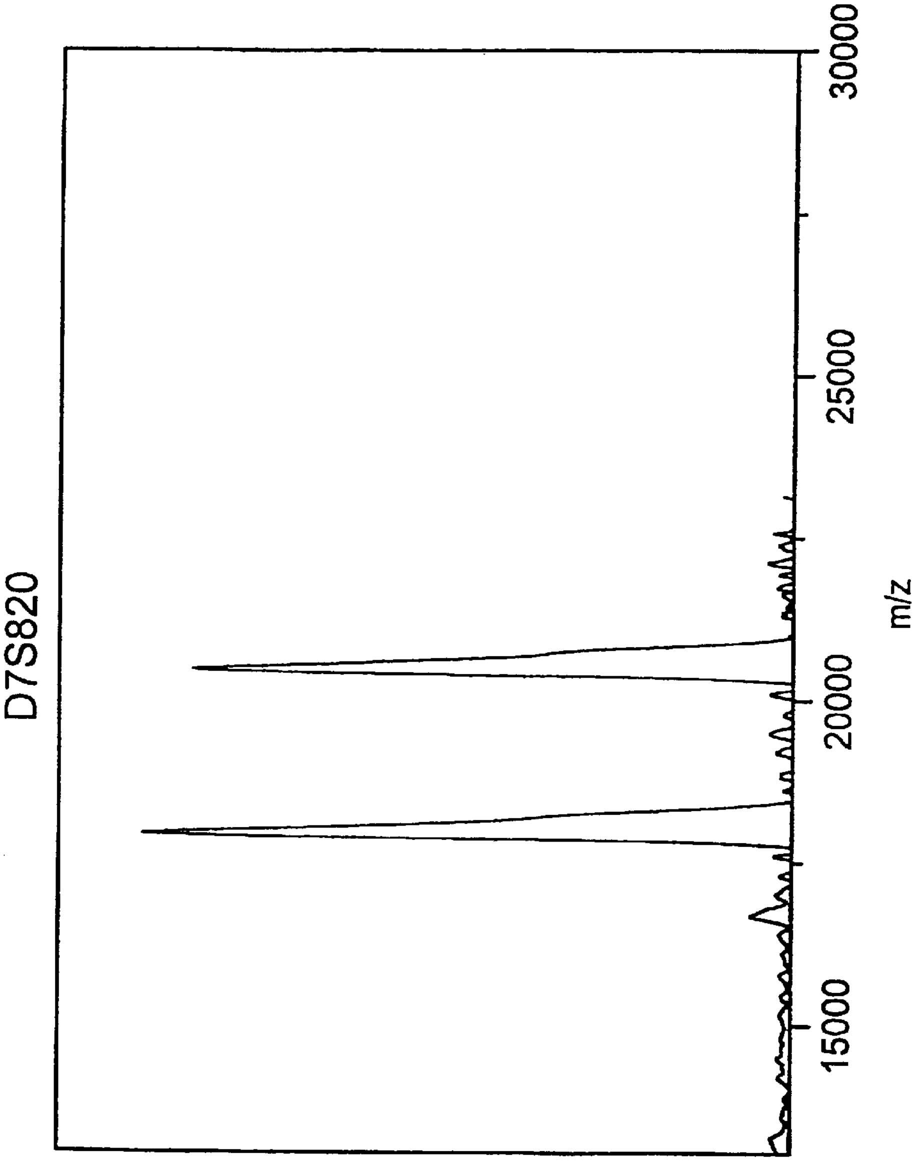
FIG. 3D displays the mass spectrum for the D7S820 locus.
Figure 3E:
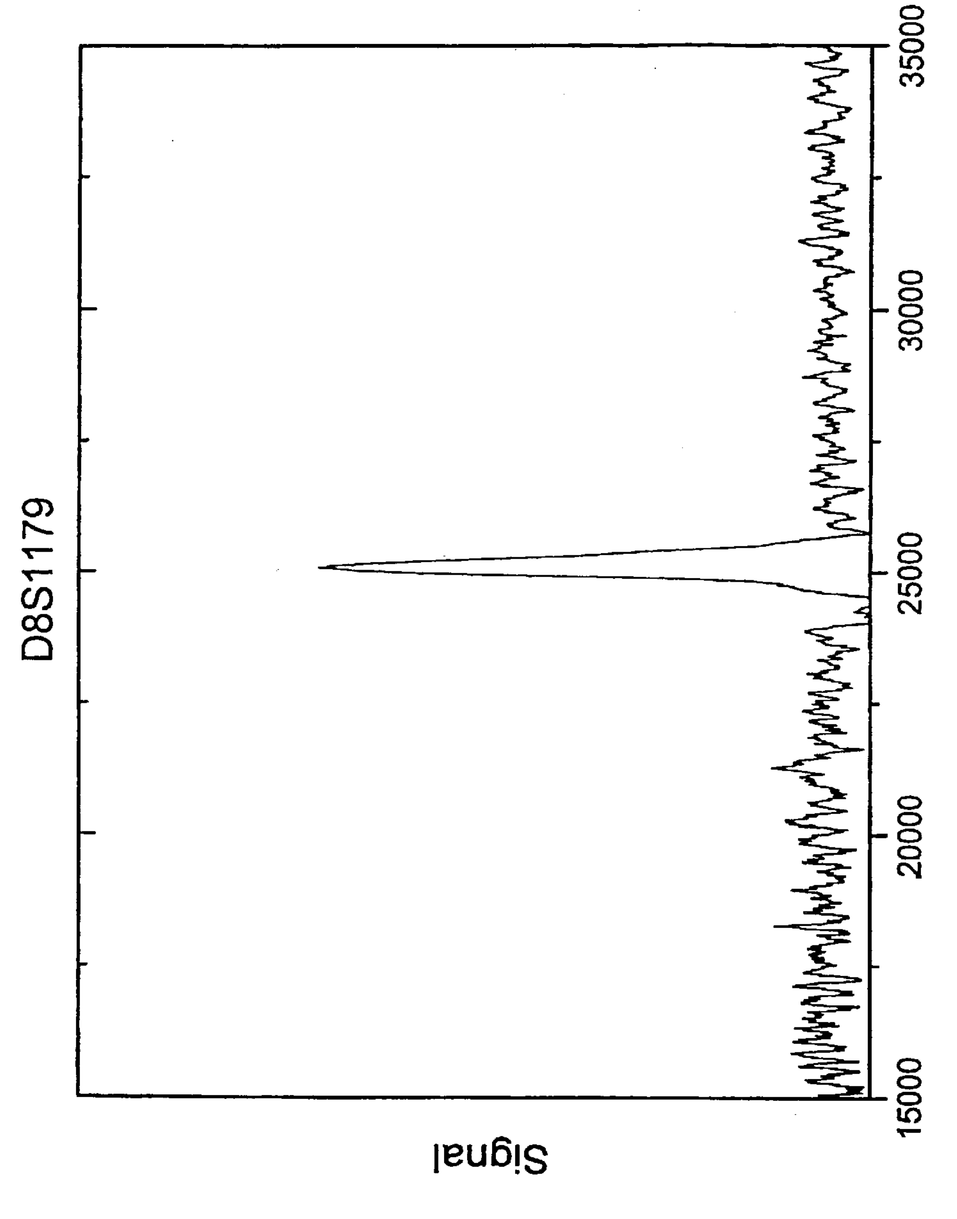
FIG. 3E displays the mass spectrum for the D8S1179 locus.
Figure 3F:
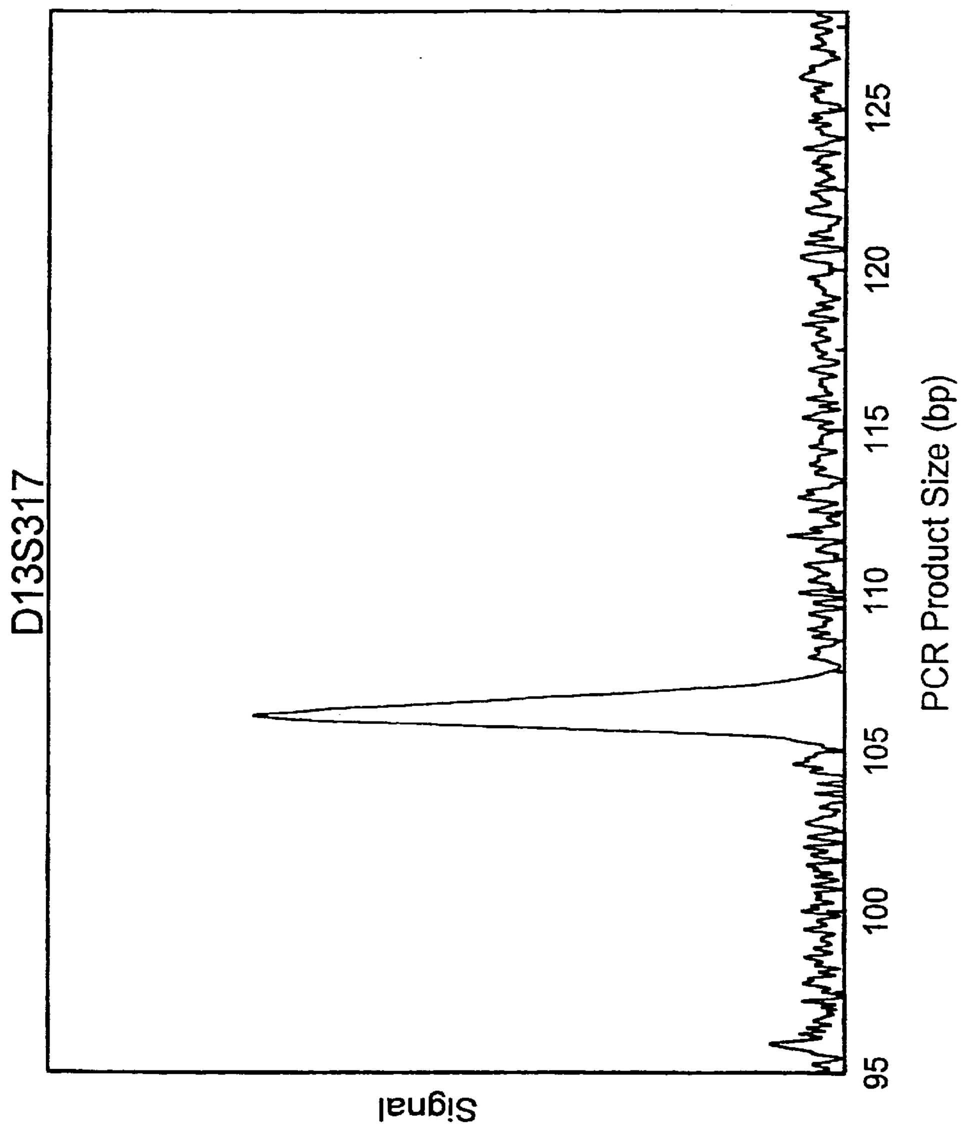
FIG. 3F displays the mass spectrum for the D13S317 locus.
Figure 3G:
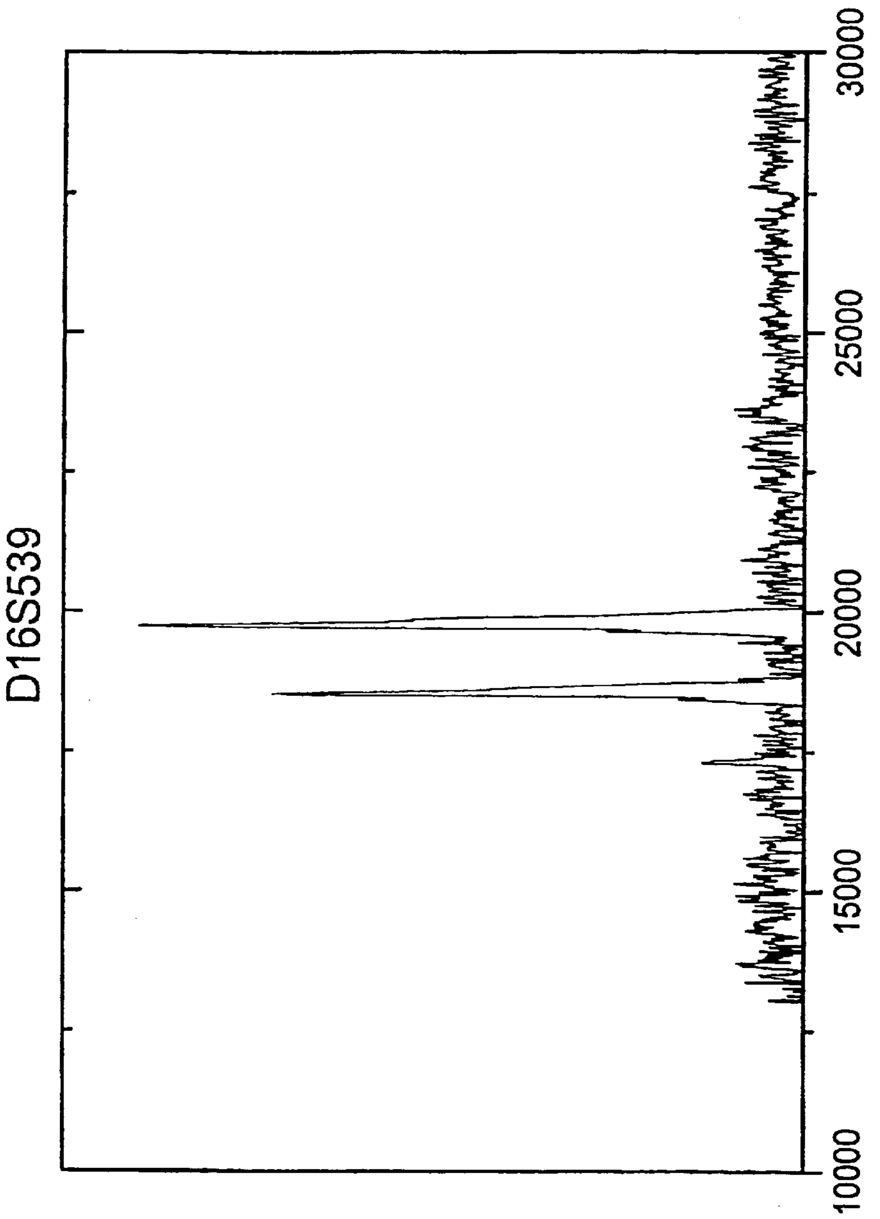
FIG. 3G displays the mass spectrum for the D16S539 locus.
Figure 3H:
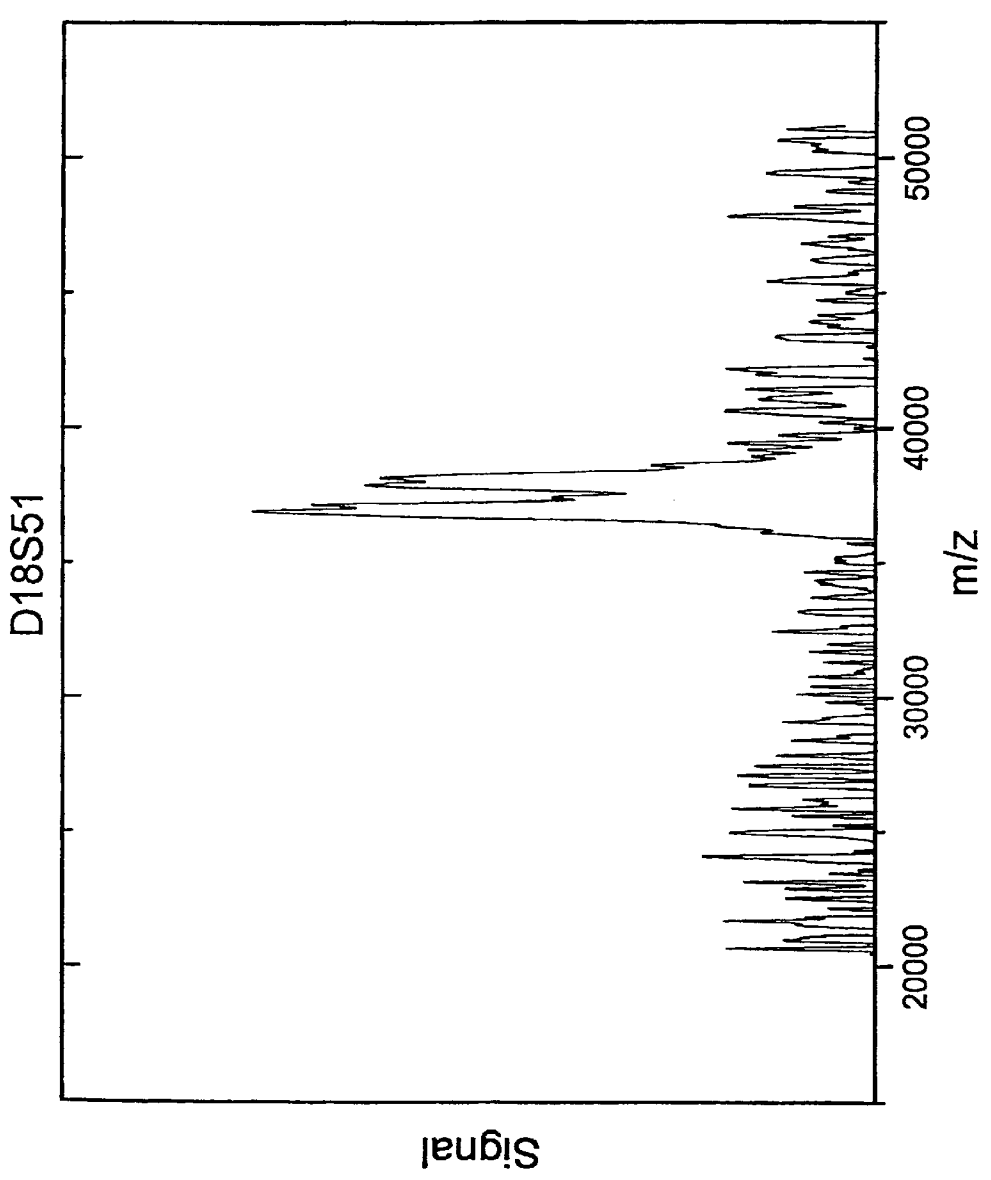
FIG. 3H displays the mass spectrum for the D18S51 locus.
Figure 3I:
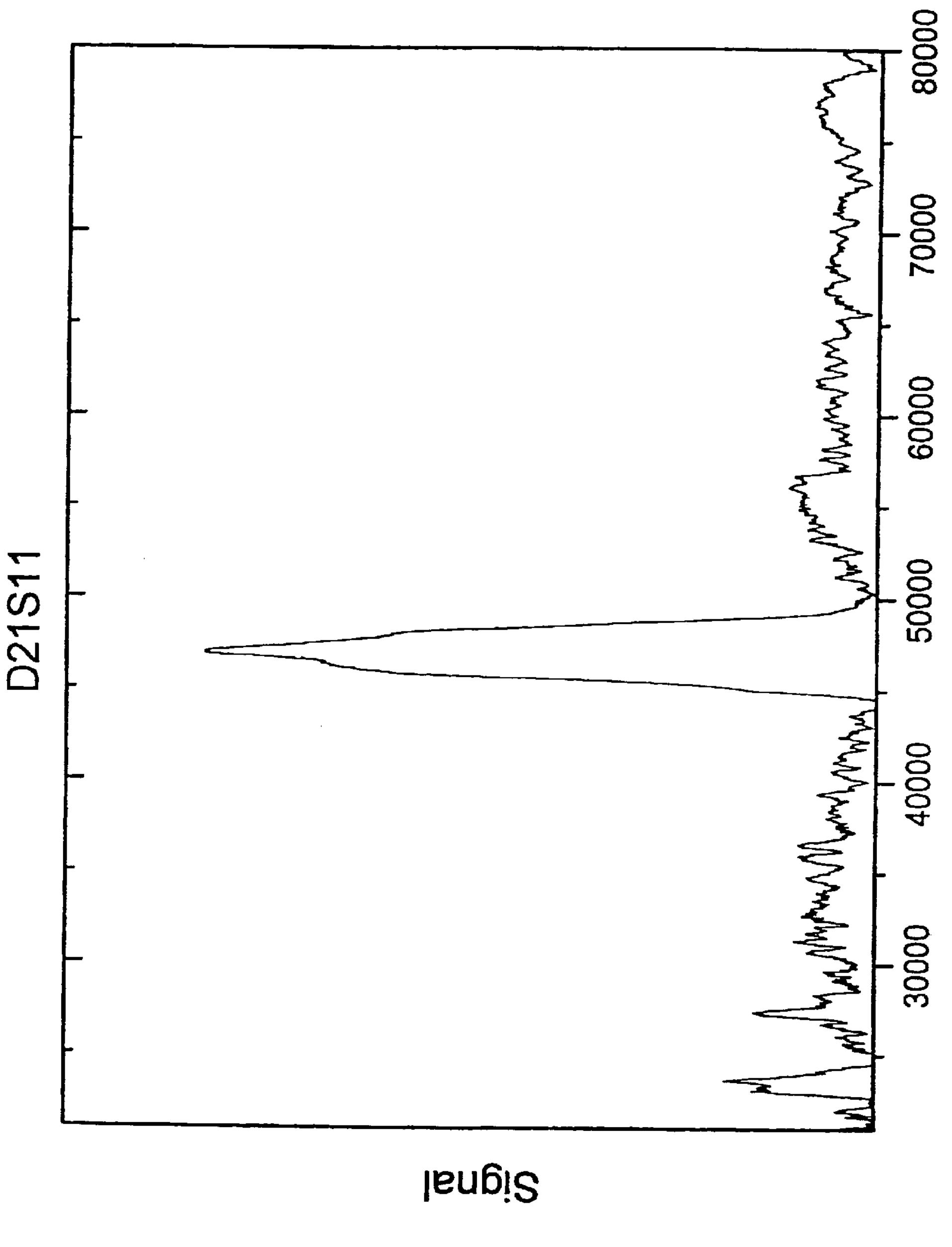
FIG. 3J displays the mass spectrum for the DYS19 locus.
FIG. 3K displays the mass spectrum for the F13A1 locus.
FIG. 3L displays the mass spectrum for the FES/FPS locus.
FIG. 3M displays the mass spectrum for the FGA locus.
FIG. 3N displays the mass spectrum for the HPRTB locus.
FIG. 3O displays the mass spectrum for the TH01 locus.
FIG. 3P displays the mass spectrum for the TPOX locus.
Figure 3J:
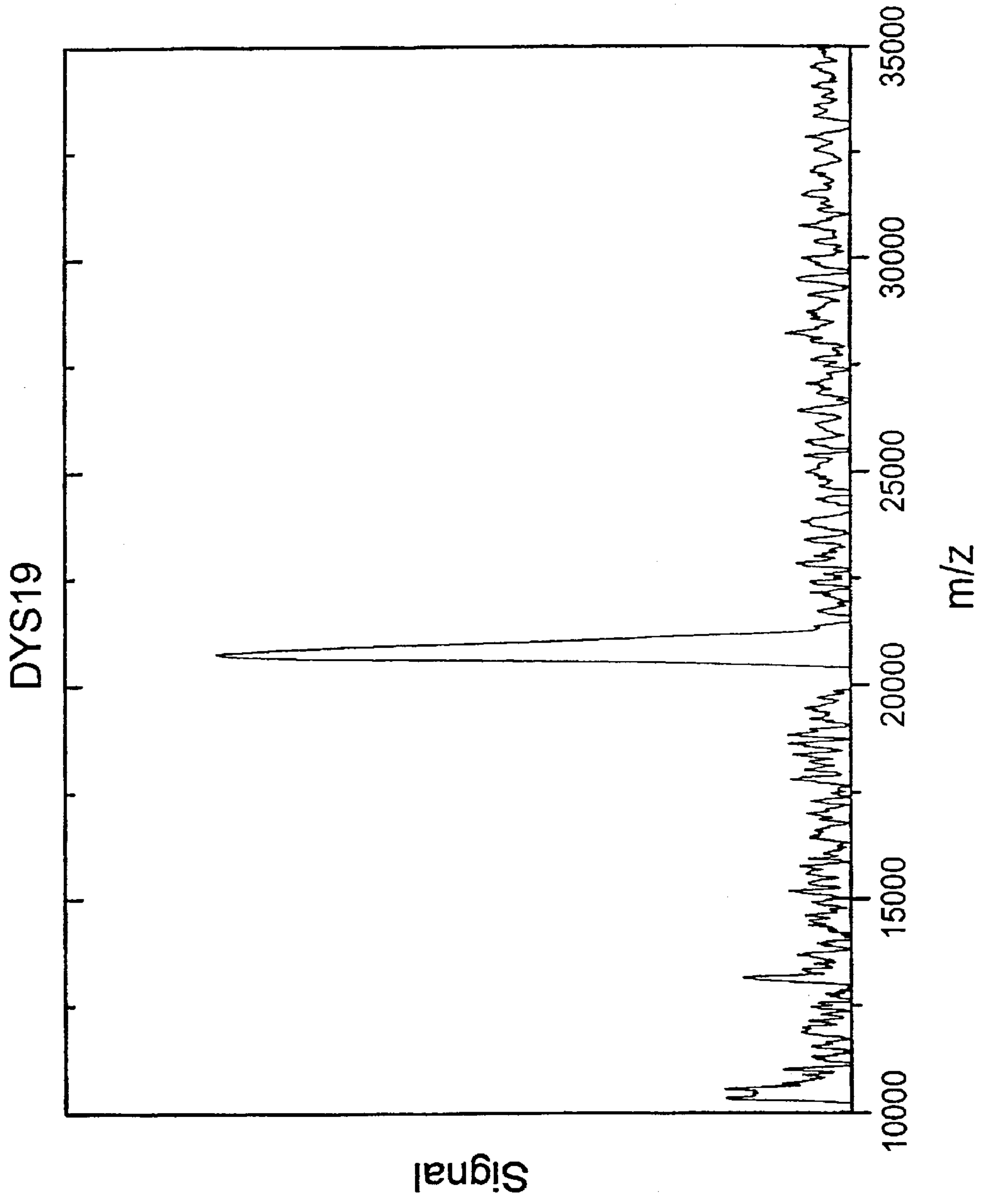
Figure 3K:
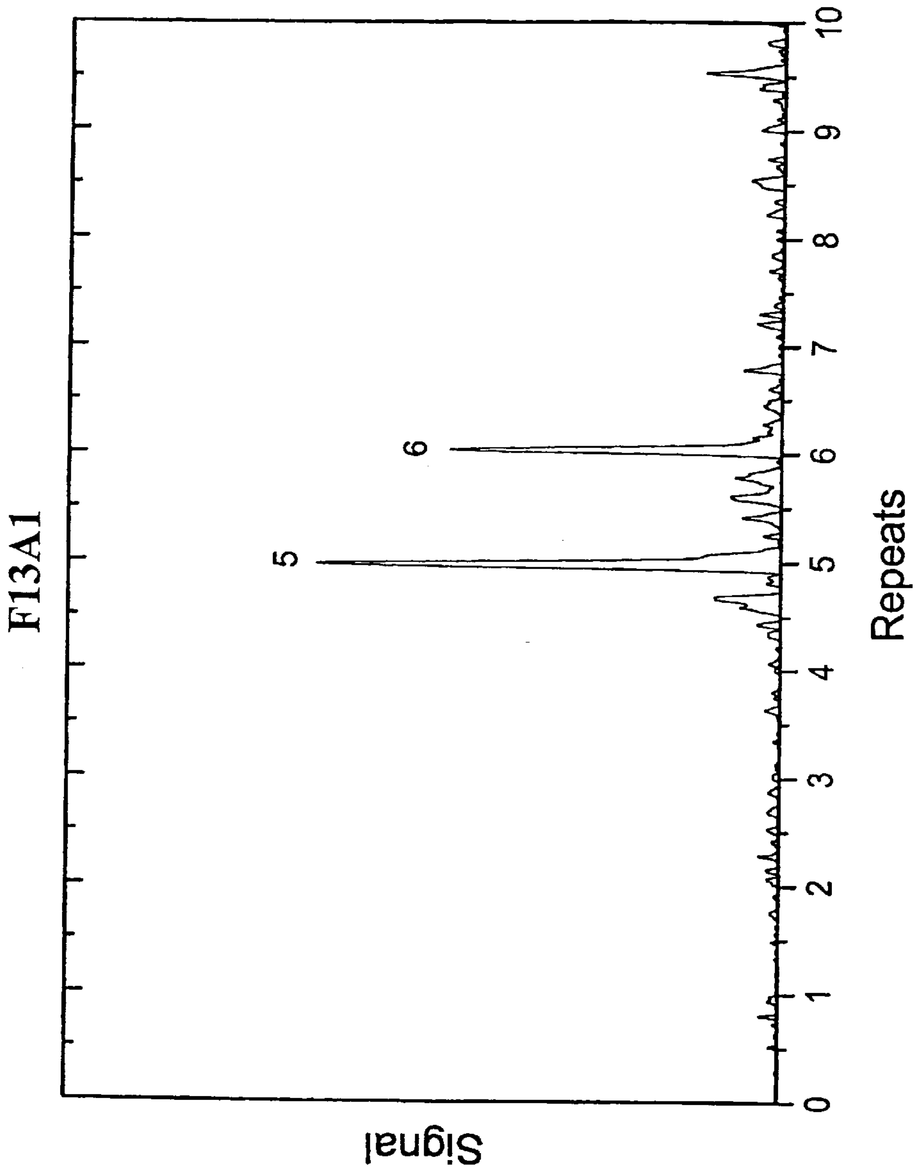
Figure 3L:
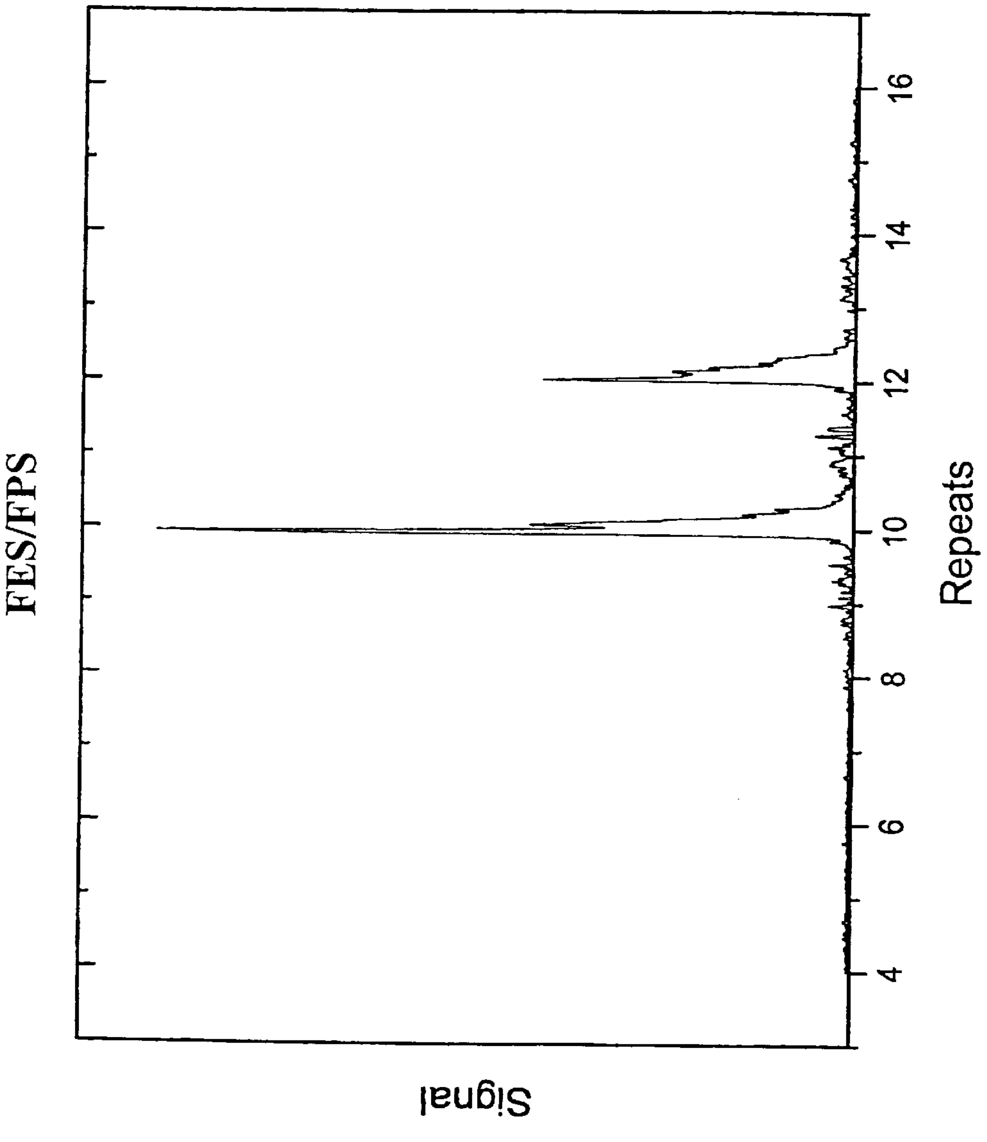
Figure 3M:
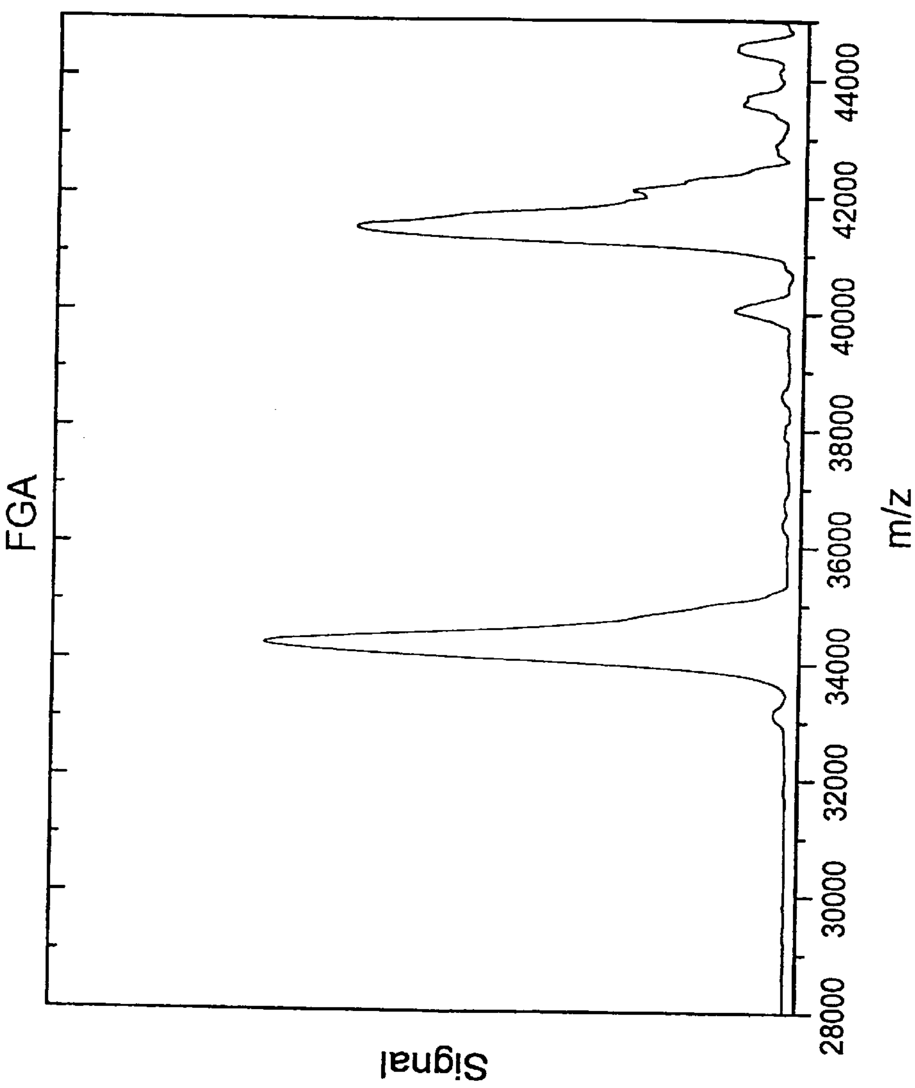
Figure 3N:
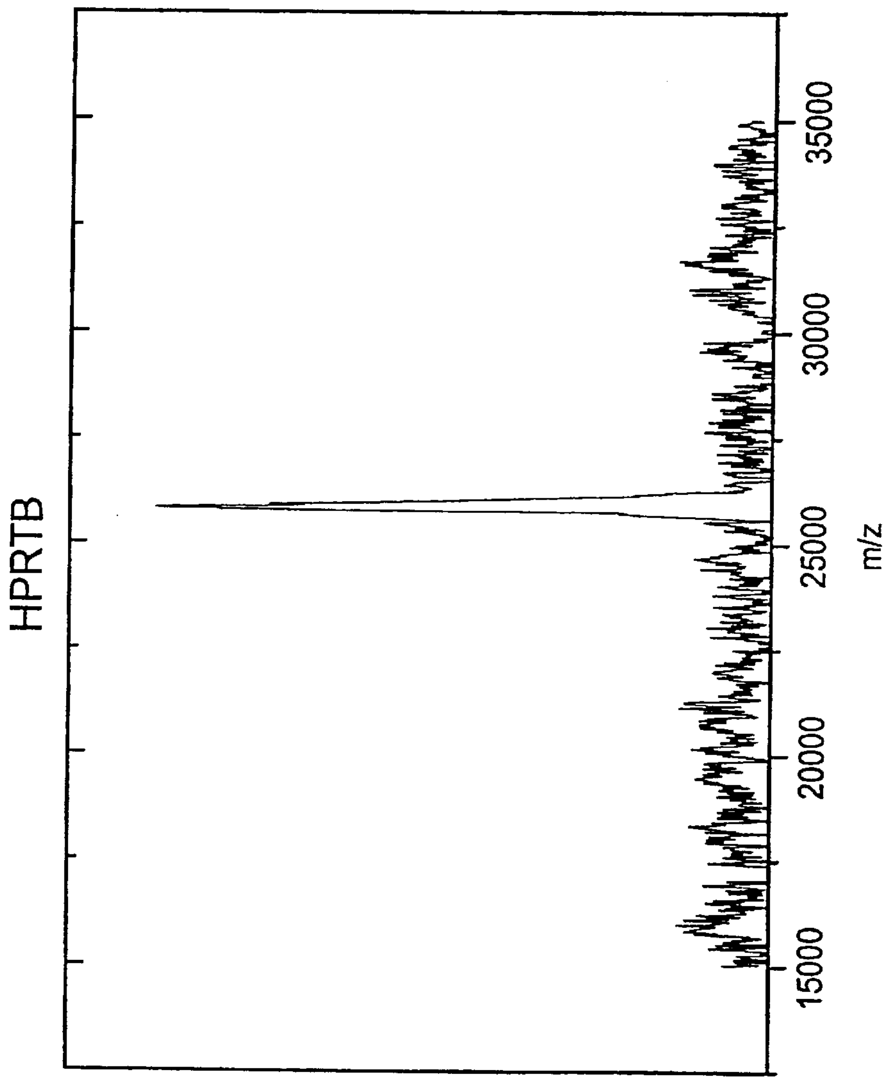
Figure 3O:
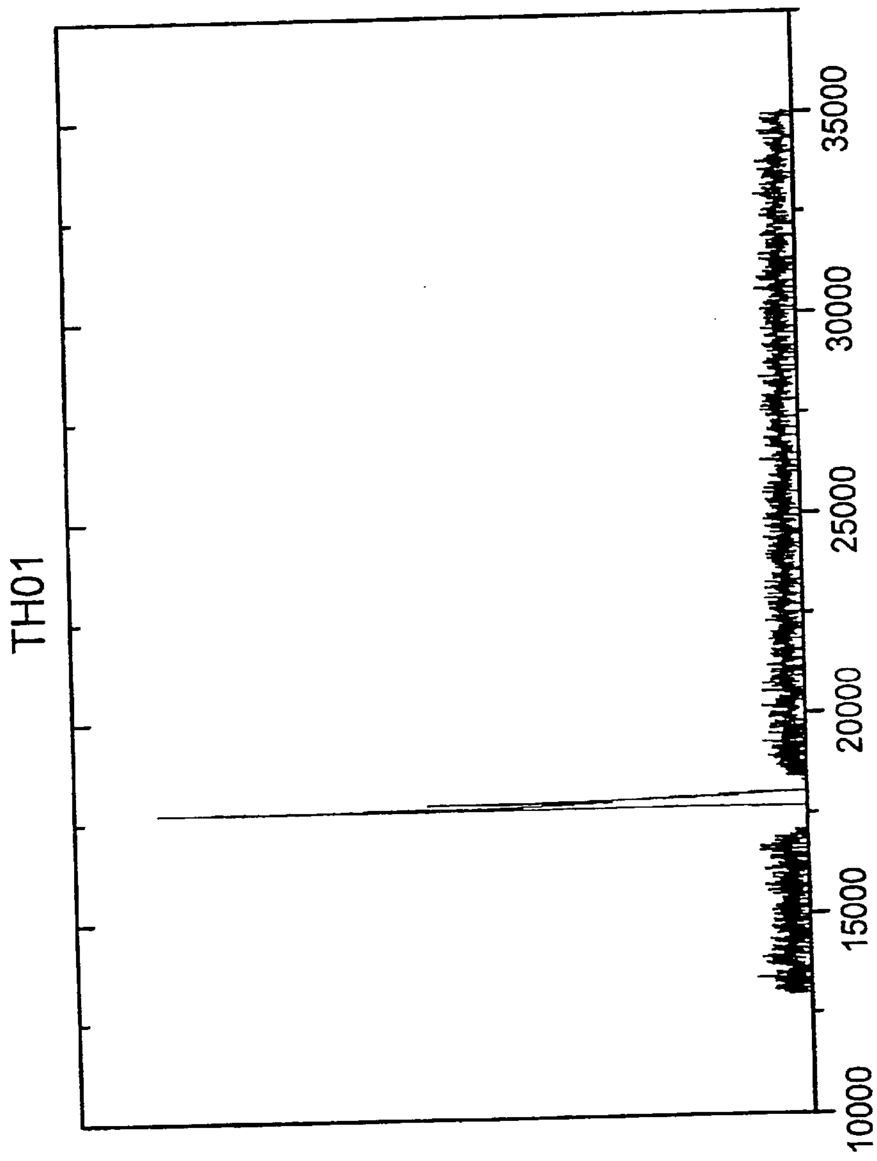
Figure 3P:
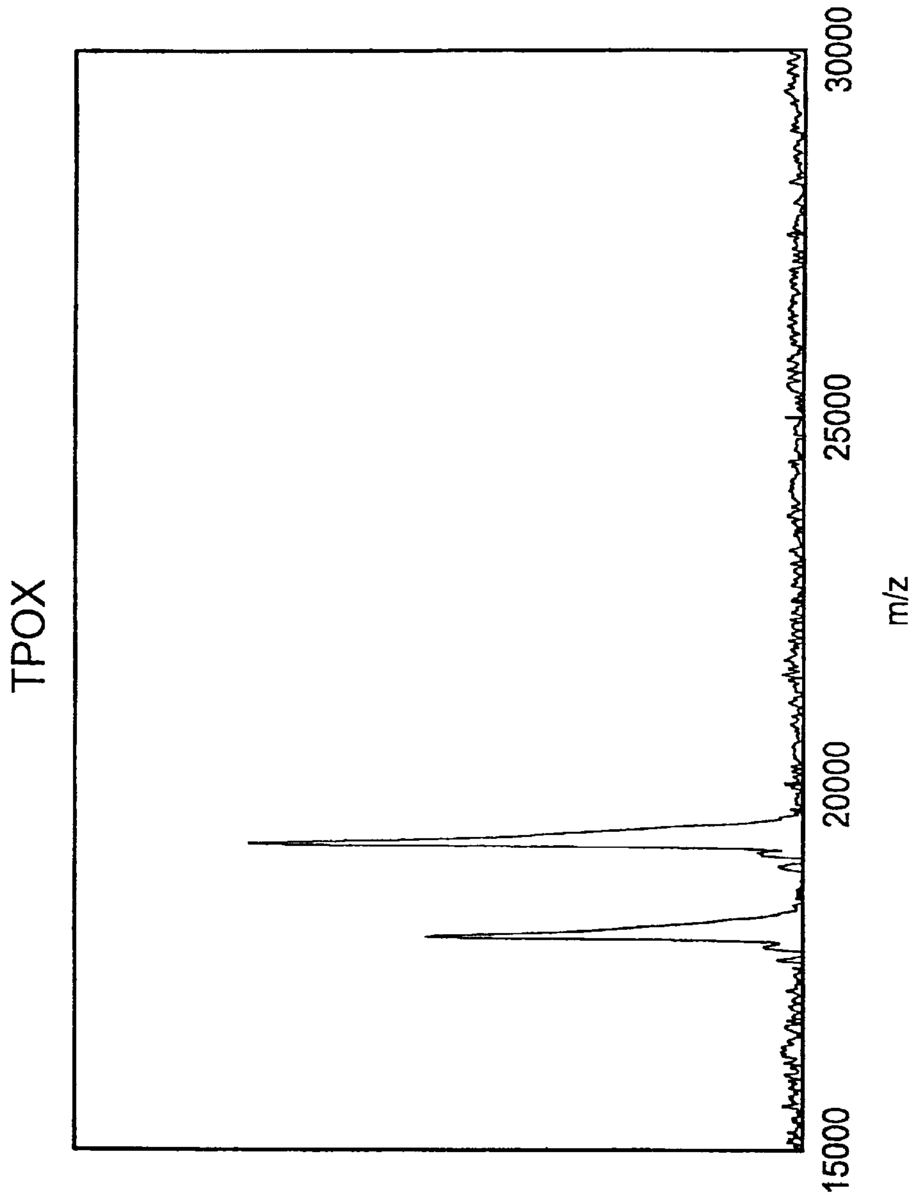
Figure 4:
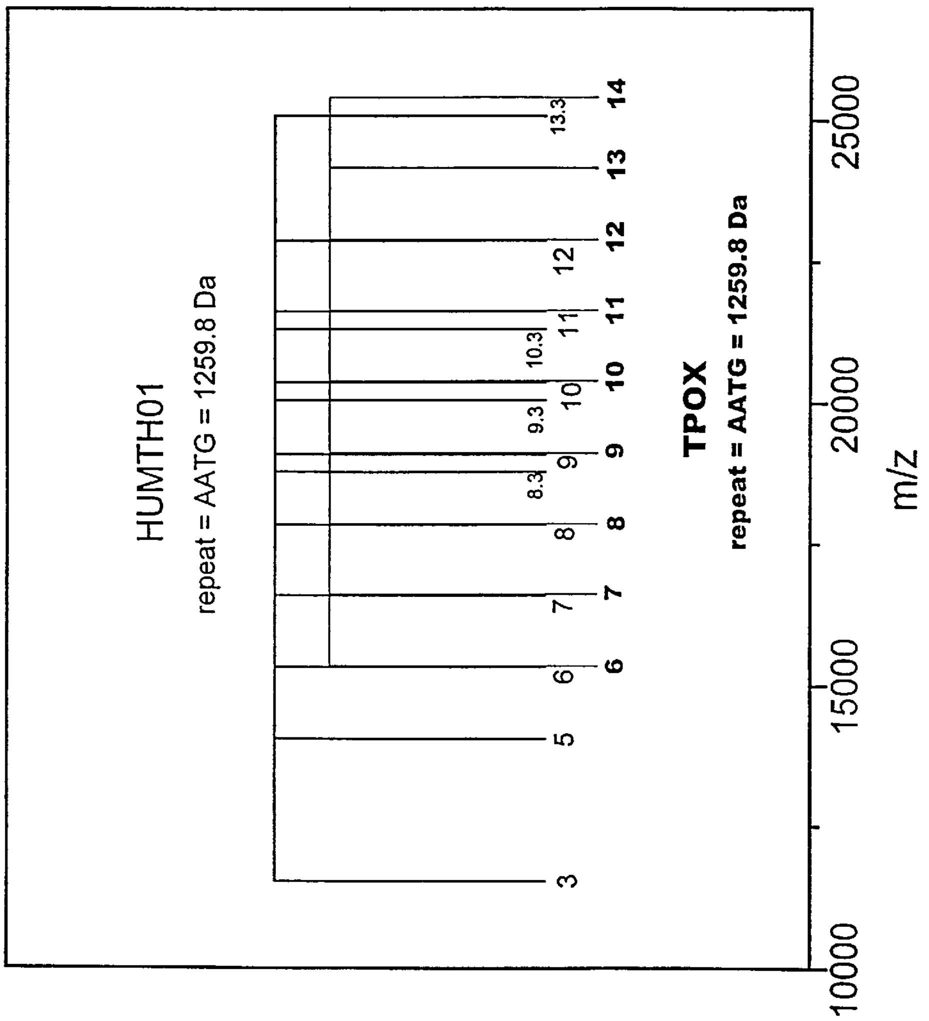
FIG. 4 is a simulated multiplex STR analysis of alleles with overlapping size ranges. This diagram depicts the expected masses for known alleles of TPOX and TH01.
Figure 5:
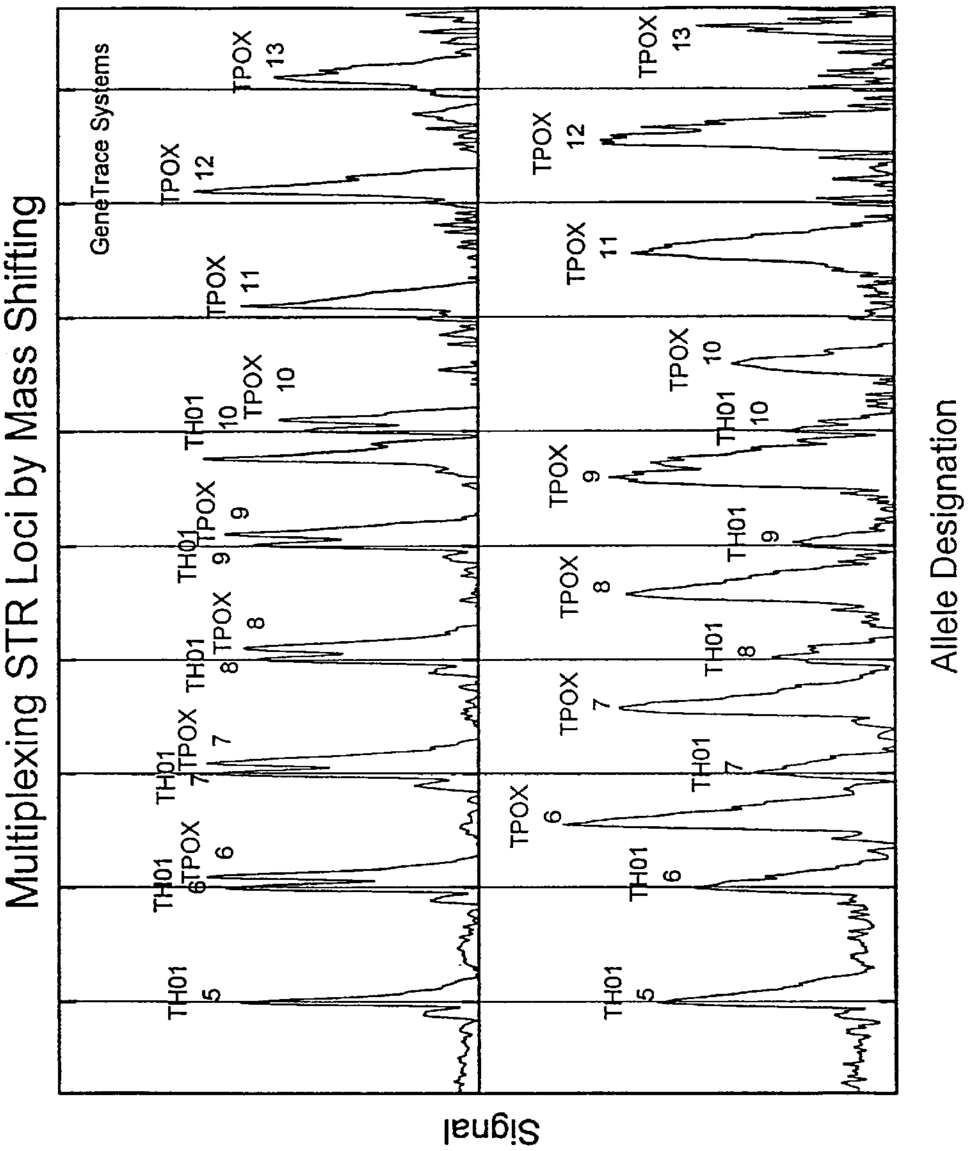
FIG. 5 are mass spectra of mixtures of TH01 and TPOX allelic ladders. Using the primer sequences for TH01 (SEQ ID NO.:29 and SEQ ID NO.:30) and TPOX (SEQ ID NO.:31 and SEQ ID NO.:32), alleles between the different STR systems differ by only 120 Daltons (top spectrum). By adding two nucleotides to the 5'-end of the reverse primer for TPOX (SEQ ID NO.:32), the TPOX allele masses are increased by ~600 Daltons, making them easier to resolve.
Figure 6:
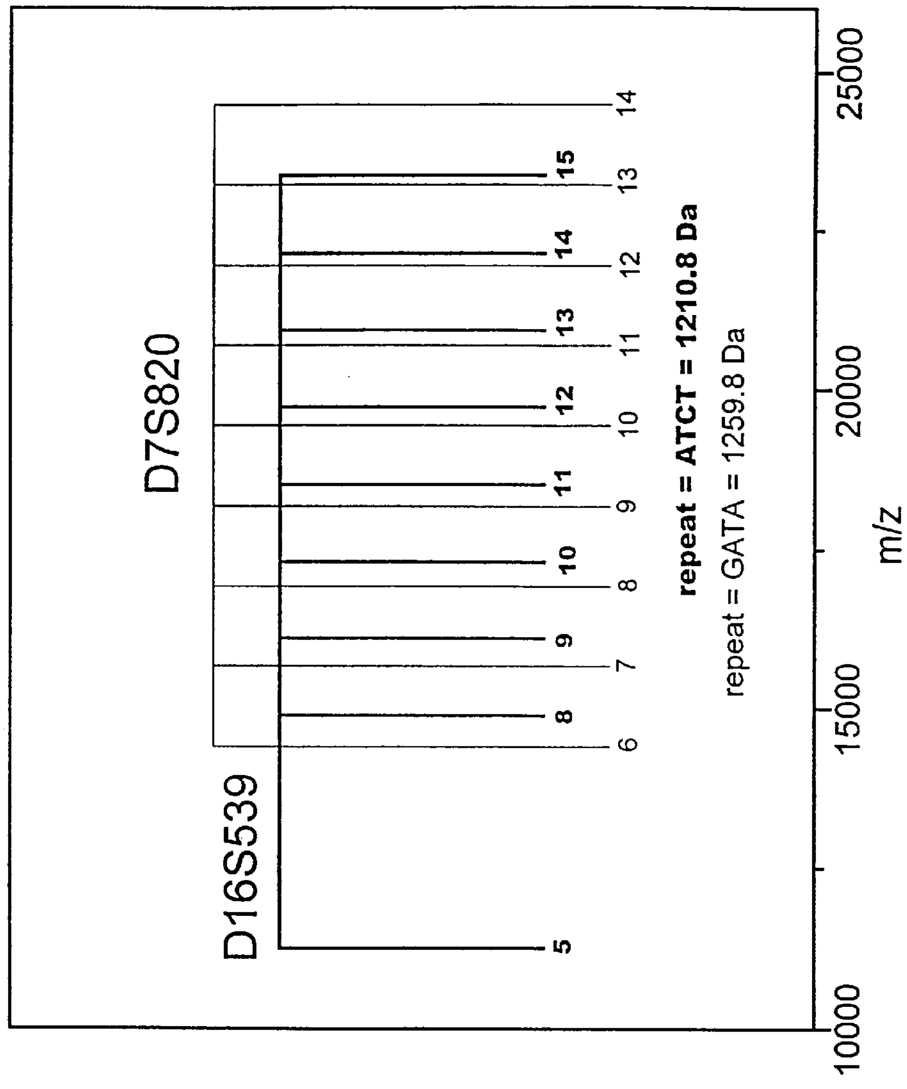
FIG. 6 is a simulated multiplex STR analysis depicting the expected masses for D16S539 and D7S820 known alleles. Even with different repeat sequences, all known alleles may be resolved by mass spectroscopy.
Figure 7A:
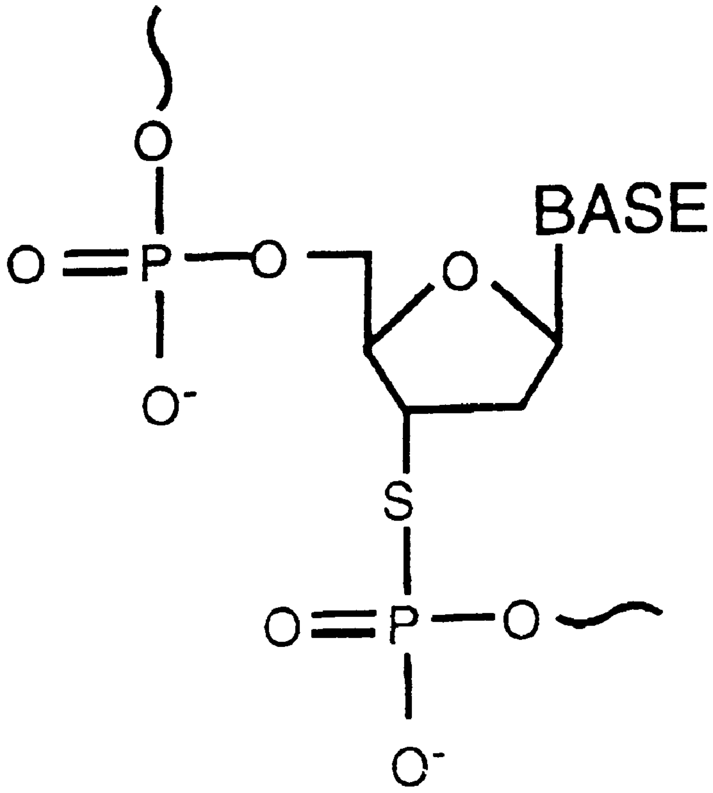
FIG. 7A shows the chemical formula for 2'-deoxythymidine-3'-(S)-phosphorothioate.
Figure 7B:
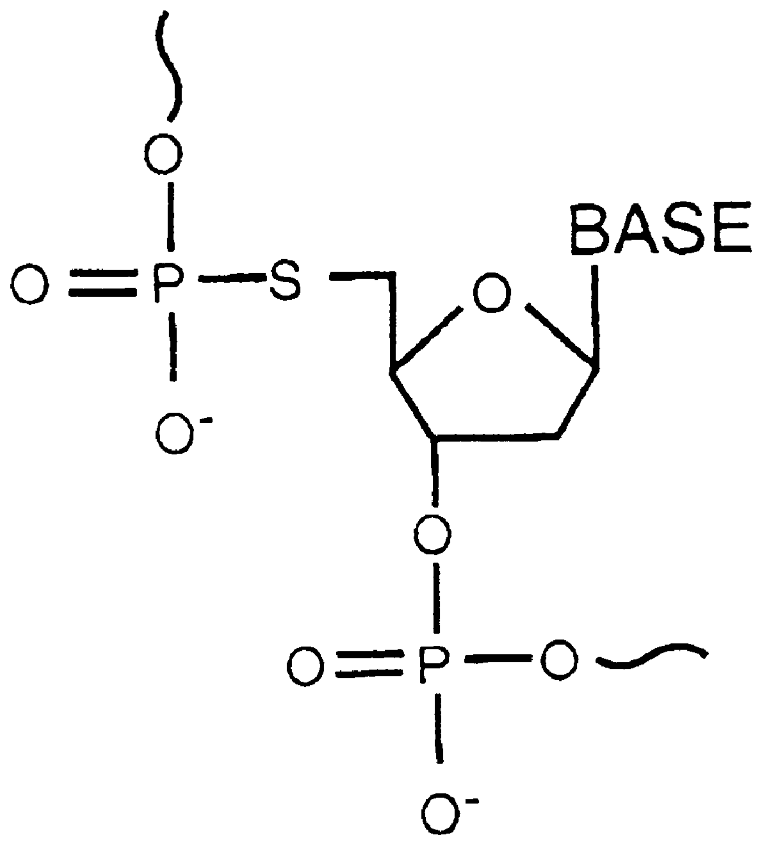
FIG. 7B shows the chemical formula for 2'-deoxythymidine-5'-(S)-phosphorothioate.

These new oligonucleotide primers are designed to match a portion of the flanking regions for DTNR loci consisting of: CSF1PO, D3S1358, D5S818, D7S820, D8S1179, D13S317, D16S539, D18S51, D21S11, DYS19, F13A1, FES/FPS, FGA, HPRTB, TH01, TPOX, DYS388, DYS391, DYS392, DYS393, D2S1391, D18S535, D2S1338, D19S433, D6S477, D1S518, D14S306, D22S684, F13B, CD4, D12S391, D10S220 a With the exception of D3S1358, sequences for the STR loci of this invention are accessible to the general public through GenBank using the accession numbers listed in Table 1. The sequence ID Numbers given in Table 1 correspond to the DNA sequence of the DNA tandem repeat regions of each locus and its flanking regions. Flanking sequences further from the DTNR region could easily be obtained by one of skill in the art by accessing the GenBank listings. FIGS. 3A–3P display mass spectra for each of the STR loci listed in TABLE 1. It will be apparent to one skilled in the art that small variation of these primers will also serve effectively, for example, adding or deleting one or a few bases from the primer and/or shifting the position relative to the template sequence by one or a few bases.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the primer sequences set forth in Table1 or to any continuous portion of the sequence as in the DTNR loci, whose locus sequence ID numbers are listed in Table 1 or any other DTNR locus, from about 14–25 nucleotides in length up to and including the full length sequence, that one wishes to utilize as a probe or primer. The choice of probe and primer sequences may be governed by various factors known to those of skill in the art.

The process of selecting and preparing a nucleic acid segment that includes a contiguous sequence from within the DTNR loci, whose locus sequence ID numbers are listed in Table 1 or any other DTNR locus, may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be chosen for their ability to selectively form duplex molecules with complementary stretches of the flanking regions of DNA nucleotide repeat regions. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand.

Of course, for some applications, less stringent (reduced stringency) hybridization conditions will be tolerated by the primer extension system in order to allow sufficiently specific formation of the heteroduplex of primer and target DNA. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated to ensure that a primer sequence will yield extension product mainly from the desired target DTNR locus.

TABLE 1

| Primer SEQ ID No.[1] | Primer Sequence (5'–3') | STR Locus[2] | Locus SEQ ID No.[3] (GenBank Accession) | PCR ™ Size[4] | Repeat[5] |
|---|---|---|---|---|---|
| 1, 100 | ACAGTAACTGCCTTCATAGATAG | CSF1PO-F | 104 | 12 = 113 bp | AGAT |
| 2, 33 | GTGTCAGACCCTGTTCTAAGTA | CSF1PO-R | (X14720) | | |

TABLE 1-continued

| Primer SEQ ID No.[1] | Primer Sequence (5'–3') | STR Locus[2] | Locus SEQ ID No.[3] (GenBank Accession) | PCR ™ Size[4] | Repeat[5] |
|---|---|---|---|---|---|
| 3 | ACTGCAGTCCAATCTGGGT | D3S1358-F | — | 16 = 109 bp | GAYA |
| 4, 34 | ATGAAATCAACAGAGGCTTG | D3S1358-R | — | | |
| 5, 35 | CTCTTGGTATCCTTATGTAATATT | D5S818-F | 105 | 11 = 105 bp | AGAT |
| 6 | ATCTGTATCCTTATTTATACCTCTATCTA | D5S818-R | (G08446) | | |
| 7, 36 | TGTCATAGTTTAGAACGAACTAAC | D7S820-F | 106 | 12 = 90 bp | GATA |
| 8 | GAAAAACTATCAATCTGTCTATCTAT | D7S820-R | (G08616) | | |
| 9, 37 | TTTGTATTTCATGTGTACATTCGTATC | D8S1179-F | 107 | 12 = 106 bp | TATC |
| 10 | ACCTATCCTGTAGATTATTTTCACTGTG | D8S1179-R | (G8710) | | |
| 11, 38 | CCCATCTAACGCCTATCTGTATT | D13S317-F | 108 | 13 = 122 bp | TATC |
| 12 | GCCCAAAAAGACAGACAGAAAG | D13S317-R | (G09017) | | |
| 13 | AGACAGACAGACAGGTGGATAGA | D16S539-F | 109 | 11 = 83 bp | GATA |
| 14, 39 | TCTCTGTTTTGTCTTTCAATGATA | D15S539-R | (G07925) | | |
| 15 | TGAGTGACAAATTGAGACCTT | D18S51-F | 110 | 13 = 114 bp | AGAA |
| 16, 40 | GTCTTACAATAACAGTTGCTACTATT | D18S51-R | (L18333) | | |
| 17, 41 | CCCAAGTGAATTGCCTTCTA | D21S11-F | 111 | 26 = 150 bp | TCTR |
| 18 | GTAGATAGACTGGATAGATAGACGATA G | D21S11-R | (M84567) | | |
| 19, 42 | GTGTTTTAGATAGATAGATAGGTA | DYS19-F | 112 | 10 = 84 bp | TAGA |
| 20 | GGTTAAGGAGAGTGTCACTA | DYS19-R | (X77751) | | |
| 21, 43 | CAGAGCAAGACTTCATCTG | F13A1-F | 113 | 7 = 128 bp | AAAG |
| 22 | TCATTTTAGTGCATGTTC | F13A1-R | (M21986) | | |
| 23, 44 | TTAGGAGACAAGGATAGCAGTTC | FES/FPS-F | 114 | 11 = 91 bp | ATTT |
| 24 | GCGAAAGAATGAGACTACTATCT | FES/FPS-R | (X06292) | | |
| 25, 45 | AAAATTAGGCATATTTACAAGCTAGTT | FGA-F | 115 | 21 = 142 bp | CTTT |
| 26 | TCTGTAATTGCCAGCAAAAAAGAAA | FGA-R | (M64982) | | |
| 27, 46 | GTCTCCATCTTTGTCTCTATCTCTATCTG | HPRTB-F | 116 | 13 = 108 bp | TCTA |
| 28 | GAGAAGGGCATGAATTTGCTTT | HPRTB-R | (M26434) | | |
| 29 | CCTGTTCCTCCCTTATTCCC | TH01-F | 117 | 9 = 79 bp | TCAT |
| 30, 47 | GGGAACACAGACTCCATGGT | TH01-R | (D00269) | | |
| 31, 48 | CTTAGGGAACCCTCACTGAATG | TPOX-F | 118 | 11 = 89 bp | AATG |
| 32 | GTCCTTGTCAGCGTTTATTTGC | TPOX-R | (M68651) | | |
| 49 | GTGAGTTAGCCGTTAGCGAT | DYS388-F | 119 | 17 = 108 bp | ATT |
| 50, 83 | GAGCGAGAGTCCGTCTCA | DYS388-R | (G09695) | | |
| 51, 84 | TTCAATCATACACCCATATCTGTC | DYS391-F | 120 | 9 = 99 bp | TCTR |
| 52 | ATAGAGGGATAGGTAGGCAGGC | DYS391-R | G09613 | | |
| 53, 85 | TTTTTCTTGTATCACCATT | DYS392-F | 121 | 16 = 98 bp | TAT |
| 54 | AAACCTACCAATCCCATTCCTT | DYS392-R | G09867 | | |
| 55, 85 | TGGTCTTCTACTTGTGTCAATAC | DYS393-F | 122 | 15 = 106 bp | AGAT |
| 56 | TGTCTCATAGAAAAGACATACAT | DYS393-R | G09601 | | |
| 57, 87 | CTGGATTTCTTGGTTATAGTAAA | D2S1391-F | 123 | 12 = 100 bp | TCTA |
| 58 | AAGCTGGTAGAGAGATACACAGA | D2S1391-R | G08168 | | |
| 59 | AGCCACACCCATAACTTT | D18S535-F | 124 | 14 = 120 bp | GATA |
| 60, 88 | GAATGCAGAGAAAGAGAATCTA | D18S535-R | G07985 | | |
| 61, 89 | AGAAATGGCTTGGCCTTA | D2S1388-F | 125 | 11 = 100 bp | CCTT |
| 62 | TAAAGGATTGCAGGAGGG | D2S1388-R | G08202 | | |
| 63 | GAATAAGATTCTGTTGAAGGAAA | D19S433-F | 126 | 11 = 100 bp | AAGG |
| 64, 90 | AATCTTCTCTCTTTCTACCTCTCT | D19S433-R | G08036 | | |
| 65, 91 | AGGGCTGATGAGGTGAAATA | D6S477-F | 127 | 16 = 120 bp | ATCT |
| 66 | TCAACAACAACACATATAAGATGA | D6S477-R | G08543 | | |
| 67 | CATATATTTGTAGATGGATAGAAGA | D1S518--F | 128 | 14 = 105 bp | GATA |
| 68, 92 | GAGTTCTCCAGAGAAACAGAATC | D1S518-F | G07854 | | |
| 69, 93 | CAGACTAGATAGATAGATACGTACATA CA | D14S306-F | 129 | 14 = 139 bp | AGAT |
| 70 | TCAAAGAGTGACAAAGAAACTAAA | D14S306-R | G09055 | | |
| 71, 94 | CCATCCATCTATCATCTATTTATT | D22S684-F | 130 | 11 = 100 bp | TATC |
| 72 | ACCTACATTAGTCTGTGTTCTCT | D22S684-R | G08089 | | |
| 73, 95 | AAGAAAGAATGACCCTTGGAATTT | F13B-F | 131 | 10 = 97 bp | TTTA |
| 74 | GGGCGACAGAGCAAGACTC | F13B-R | M64554 | | |
| 75, 96 | TGGAGTCGCAAGCTGAACTA | CD4-F | 132 | 9 = 108 bp | TTTTC |
| 76 | CTGAGTGACAGAGTGAGAACCTG | CD4-R | M86525 | | |
| 77, 97 | ATCAATGGATGCATAGGTA | D12S391-F | 133 | 20 = 142 bp | YAGA |
| 78 | GCCTCCATATCACTTGAGCTAAT | D13S391-R | G08921 | | |
| 79, 98 | GCCTTACTGACTTACTACATAACGA | D10S220-F | 134 | 23 = 100 bp | CA |
| 80 | GAGCAAGACTGCATCTCAAAA | D10S220-R | Z17087 | | |
| 81, 99 | TGGAAAAATATTCTGGGAAGATA | D7S523-F | 135 | 17 = 100 bp | CA |
| 66 | CCTGTTGACATTTTTAAAACCA | D7S523-R | Z17102 | | |
| 101 | GCCTGTTCCTCCCTTATTTCCC | TH01-F | 117 | 9 = bo | TCAT |
| 102, 103 | AGGTCACAGGGAACACAGACTCC | TH01-R | D00269 | | |

[1]Bold sequence numbers correspond to primer sequences containing sequence modifications including biotinylation and the presence of a cleavable phosphorothiate linkage.
[2]F and R indicate forward and reverse primers for each locus.

TABLE 1-continued

| Primer SEQ ID No.[1] | Primer Sequence (5'–3') | STR Locus[2] | Locus SEQ ID No.[3] (GenBank Accession) | PCR ™ Size[4] | Repeat[5] |
|---|---|---|---|---|---|

[3]The sequence listings contain the Genbank sequence for each of the tandem repeat loci including the DNA tandem repeat region and flanking regions for each locus. The sequence listings correspond to only a portion of the full Genbank sequence listing.
[4]The first number in the PCR product size is the number of repeats found in the Genbank sequence listing for each locus and the second is the predicted size of PCR product from the Genbank sequence when using the listed primers to amplify the tandem repeat locus. Of course, the number of tandem repeats within a population of individuals will vary and therefore so will the PCR product size when individual samples are analyzed.
[5]Repeats sequence nomenclature used here is according to the latest recommendations of the DNA Commission of the International Society for Forensic Haemogenetics, and described in Int. J. Legal Med. 110:175–176 (1997).

At least one of the primers in each locus-specific pair contains a biotin moiety at the 5'-end and a phosphorothioate linkage attached to a T near the 3'-end for a capture and release assay using streptavidin-coated magnetic beads (PCT Patent Application No. WO 96/37630). Although many of the specific primers of the present invention are designed for use in such a capture and release assay, such primers need not contain either solid-binding or cleavable sites, or may contain any combination of them.

The purpose of such an assay is to increase mass resolution by (1) allowing for higher purities of the nucleic acid extension product and (2) decreasing the size of the nucleic acid extension product. Binding to a solid support fulfills the first goal by allowing for stringent washes and removing the complementary strand of the DNA which provides cumulative information and complicates the mass spectra decreasing the resolution.

This assay may be used to isolate single-stranded or double-stranded amplified target nucleic acids. Typically, at least one strand of an amplified target nucleic acid is bound to a solid support to permit rigorous washing and concomitant removal of salt adducts, unwanted oligonucleotides and enzymes. Either a double-stranded amplified target nucleic acid or a single-stranded amplified target nucleic acid may be isolated for mass spectrometric analysis depending upon the stringency of the wash. The single-stranded amplified target nucleic acid analyzed may be either the strand bound or not bound to the solid support. If the unbound strand is used for MS analysis, it is purified by first washing the bound strand and its attached complement under conditions not sufficiently rigorous to disrupt the strand. After unwanted biomolecules and salts are removed, the complement can then be released under more rigorous conditions. Cleavable linkers or cleavable primers may then be used to release the bound strands from the solid support prior to MS analysis.

The second goal is met by having cleavable sites in the primer. Such cleavable sites also eliminate unnecessary sequences and allow for the use of a capture and release assay and for primer modification for the interleaving multiplexing method, described herein. For example, moving the cleavable site along the primer backbone directly modifies the mass of the PCR™ product. The cleavable site is typically introduced via a cleavable primer and the cleavable site is located outside of the region of interest. Cleavable primers may include those comprising an exonuclease blocking moiety, a Type IIS restriction endonuclease recognition site, and a Type II restriction endonuclease recognition site.

The target nucleic acids may, thus, be reduced in length by any of the methods known that will cleave within one or more flanking regions preferably without cleaving within the region of interest. Exemplary methods of reducing length include: cleaving at endogenous restriction endonuclease cleavable sites present in one or more flanking regions but absent in the region of interest; cleaving at restriction endonuclease cleavable sites at or adjacent to restriction endonuclease recognition sites incorporated into one or more flanking regions by use of one or more cleavable primers comprising said restriction endonuclease recognition sites; cleaving at a combination of restriction endonuclease cleavable sites wherein the sites are endogenous and/or introduced using mismatch or overhanging primers; and selective digestion of one or more flanking regions using exonuclease and an exonuclease blocking moiety to protect the regions of interest from digestion.

The restriction endonucleases employed with the present invention include type II and type IIS restriction endonucleases. The restriction endonuclease recognition sites may be either within a primer region, or outside the primer region, so long as the restriction endonuclease cleavable sites are within one or more flanking regions and preferably not within a region of interest. For type II restriction endonucleases, the restriction endonuclease recognition site is the same as the restriction endonuclease cleavable site. For Type IIS restriction endonucleases, the cleavable site is at a defined distance away from one side of the recognition site.

Another embodiment of the invention involves using a cleavable primer having an exonuclease blocking moiety. After amplification of the target nucleic acid, the amplified target nucleic acid will include an exonuclease blocking moiety. The amplified target nucleic acid is then treated with a 5' to 3' exonuclease, which degrades the strand containing the exonuclease blocking moiety in a 5' to 3' direction only up to the blocking moiety. The 5' to 3' exonuclease may optionally degrade the other complementary strand of the amplified target nucleic acid, in cases where the other strand does not have an exonuclease blocking moiety. The treatment with the 5' to 3' exonuclease leaves a reduced-length, single-stranded amplified target nucleic acid for mass spectrometric analysis.

Cleavable sites may also include chemically cleavable groups incorporated within the phosphate backbone linkage (e.g replacement of phosphate with a phosphoramidate) or as a substituent on or replacement of one of the bases or sugars of the oligonucleotide primer (e.g. a modified base or sugar, for example, a more labile glycosidic linkage). Such chemically cleavable groups would be apparent to one of skill in the art in light of the present disclosure and include, for example, dialkoxysilane, 3'-(S)-phosphorothioate, 5'-(S)-phosphorothioate, 3'-(N)-phosphoroamidate, 5'-(N)- phosphoroamidate, and ribose. FIGS. 16A and 16B depict a 3'-(S)-phosphorothioate and 5'-(S)-phosphorothioate, respectively as defined in this invention. Note that these linkages are often referred to as thiophosphates as well. A similar nomenclature is employed for 3'-(N)-phosphoroamidate, 5'-(N)-phosphoroamidate. The chemically cleavable site should generally be stable under the amplification, hybridization and washing conditions to be employed and is preferably within one or more of the flanking regions.

In a preferred embodiment, the cleavable site is located near the 3' end of the primer used to bind the amplified target nucleic acid to the solid support. By locating the cleavable site near the 3' end, it is possible to further reduce the length of the amplified target nucleic acid, eliminating a flanking region from the polynucleotide region of interest. Cleavable primers are described in PCT/US96/06116, filed Apr. 26, 1996 (incorporated herein by reference).

The primer pairs described in this invention may be combined to generate overlapping PCR™ product sizes which are all distinguishable by mass.

EXAMPLE 1

PCR CONDITIONS FOR MULTIPLEXING DTNR RESULTS

Template: 5 uL 1:1000 dilution of AmpFISTR Green I Allelic Ladders (PE Applied Biosystems; contains common alleles from the STR loci CSF1PO, TPOX, and TH01 and the sex-typing marker amelogenin); for regular samples, 2–5 uL of 1–10 ng of human genomic DNA was added to the PCR reaction.

Reaction Mix: 20 uL reaction with 1× STR buffer (Promega; contains 1.5 mM $MgCl_2$, 200 uM dNTPs, etc.), 1 U Taq polymerase (Promega), 20 pmol forward and reverse primers with one of them being a primer containing a biotin moiety on the 5'-end and a thiothymine residue near the 3'-end of the oligonucleotide.

Thermal Cycling: In 0.2 mL tubes in an MJ Research DNA Engine (block temperature) 94° C. for 2 min; 35 cycles: 94° C. for 30 sec, 60° C. for 30 sec, 72° C. for 30 sec; 72° C. for 5 min.

EXAMPLE 2

SAMPLE PURIFICATION FOR MULTIPLEXING DTNR RESULTS

A typical binding/washing protocol for purifying samples for DTNR multiplexing includes the following steps:

a) Wash 10 uL streptavidin-coated magnetic beads with 2× binding/wash buffer b) Repeat a second time c) Add 5 uL 5× binding/wash buffer then add ~19 uL of PCR sample to the beads (1 uL was removed for an agarose gel check) and vortex sample tube for 15 min at slow speed d) Wash beads with 30 uL of 2× binding/wash buffer e) Wash beads with 30 uL of 0.1 N NaOH f) Add 30 uL of 0.1 N NaOH and vortex for 10 min at slow speed g) Wash beads with 30 uL of 0.1 N NaOH h) Wash beads with 30 uL of 20 mM ammonium acetate i) Repeat step (h) five times j) Wash beads with deionized water k) Repeat step (j) twice Note after each step, the supernatant is removed while the beads are magnetically held in the bottom of the tube.

After purification the solid bound strands were released by cleaving at the chemically cleavable thiophosphate site by the following procedure: 7 uL of 0.1 mM silver nitrate was added and the samples were incubated at 48° C. for 15 min.; the supernatant was then transferred to a clean tube and 2 uL of 70 mM DTT was added; and finally the sample was dried in a speed vacuum. For mixed samples the preceding protocol was modified in that aliquots of the samples (e.g., 3 uL TH01 ladder+3 uL TPOX ladder) were mixed before the drying step.

EXAMPLE 3

MS ANALYSIS FOR MULTIPLEXING DTNR RESULTS

The matrix consisted of a 5:1 molar ratio of 3-hydroxypicolinic acid (3-HPA; Lancaster Synthesis) to picolinic acid (PA; Aldrich) and was prepared by mixing 18 uL of a freshly prepared saturated 3-HPA solution (~0.5 M) with 2 uL of 1 M PA The sample to be analyzed was reconstituted in 0.5 uL of the matrix and manually spotted on the sample plate.

The instrument conditions employed with a linear time-of-flight mass spectrometer consisted of the following: acceleration voltage of +20 kV; delay of +3.6 kV at 1.12 usec; laser setting of 179 on the polarizer; mass gate of 5.84 usec; and 400 shots. A 2-point mass calibration with a 15-mer (4507.0 Da) and a 36-mer (10998.2 Da) was employed.

EXAMPLE 4

Oligonucleotide primers are typically prepared by the phosphoramidite approach. In this automated, solid-phase procedure, each nucleotide is individually added to the 5'-end of the growing oligonucleotide chain, which is in turn attached at the 3'-end to a solid support. The added nucleotides are in the form of trivalent 3'-phosphoramidites that are protected from polymerization by a dimethoxytrityl ("DMT") group at the 5'-position. After base induced phosphoramidite coupling, mild oxidation to give a pentavalent phosphotriester intermediate and DMT removal provides a new site for oligonucleotide elongation. These syntheses may be performed on a Perkin Elmer/Applied Biosystems Division DNA synthesizer. The oligonucleotide primers are then cleaved off the solid support, and the phosphodiester and exocyclic amino groups are deprotected with ammonium hydroxide.

The biotin, and 3'- and 5'-(S) phosphorothioate linkages are also prepared in an automated fashion from phosphoramidite intermediates using similar procedures and either modified bases or activated and protected linker molecules.

EXAMPLE 5

TWO STAGE MULTIPLEXING REACTION OUTSIDE PRIMERS FOR HIGHER LEVEL MULTIPLEX FOLLOWED BY SINGLE DDN TERMINATION

A triplex PCR reaction was run with 10-ng human genomic DNA template in a 20-uL PCR reaction. Primers specific for the three STR loci CSF1PO, TPOX, and TH01 were used as described by Huang et al. These primers produce larger sized PCR products than the primers listed in this patent and the primer sequences from Table 1 for these three STR loci are within the product region.

Multiplex PCR components: 20 μL reaction containing 1.5× Taq buffer II (PE Applied Biosystems), 200 μM dNTPs, 1.5 mM $MgCl_2$, 1 U AmpliTaq Gold (PE Applied Biosystems), 0.5 μM each primer.

Thermal cycling was performed in 0.2 mL tubes using an MJ Research DNA Engine (calculated temperature) with the following cycling parameters: 95° C. for 11 min; 40 cycles: 94° C. for 30 sec, 64° C. for 30 sec, 68° C. for 45 sec; 70° C. for 10 min.

Following PCR, the sample was treated with shrimp-alkaline phosphatase (SAP) to hydrolyze the unincorporated dNTPs. Typically, 1 U SAP was added to each 20 μL PCR sample. The sample was then incubated at 37° C. for 60 minutes followed by heating at 75° C. for 15 minutes.

A multiplexed primer extension assay was then performed using cleavable primers for the three STR loci. The reaction included three regular deoxynucleotide triphosphates (dNTP) to allow incorporation through the STR repeat region and a single dideoxynucleotide triphosphate (ddNTP) to halt extension (see Braun, et al.). The termination by the ddNTP shortened the measured STR allele.

Multiplexed primer extension reaction components: 20 μL reaction containing 1× TaqFS buffer (PE Applied Biosystems), 2.4 U TaqFS, 200 μM dGTP, 200 μM dATP, 200 μM dTTP, 400 μM ddCTP, 40 pmol CSF1PO primer (SEQ ID NO:100), 20 pmol TPOX (SEQ ID NO:31), 20 pmol TH01 (SEQ ID NO:103), and 2 μL SAP-treated PCR product (as described above).

Thermal cycling for extension reaction was performed in 0.2 mL tubes using an MJ Research DNA Engine (calculated temperature) with the following cycling parameters: 95° C. for 2 min; 30 cycles: 94° C. for 30 sec, 55° C. for 30 sec, 72° C. for 45 sec; 60° C. for 5 min. The resultant product was purified and analyzed as detailed in the examples above.

Figure 8A:
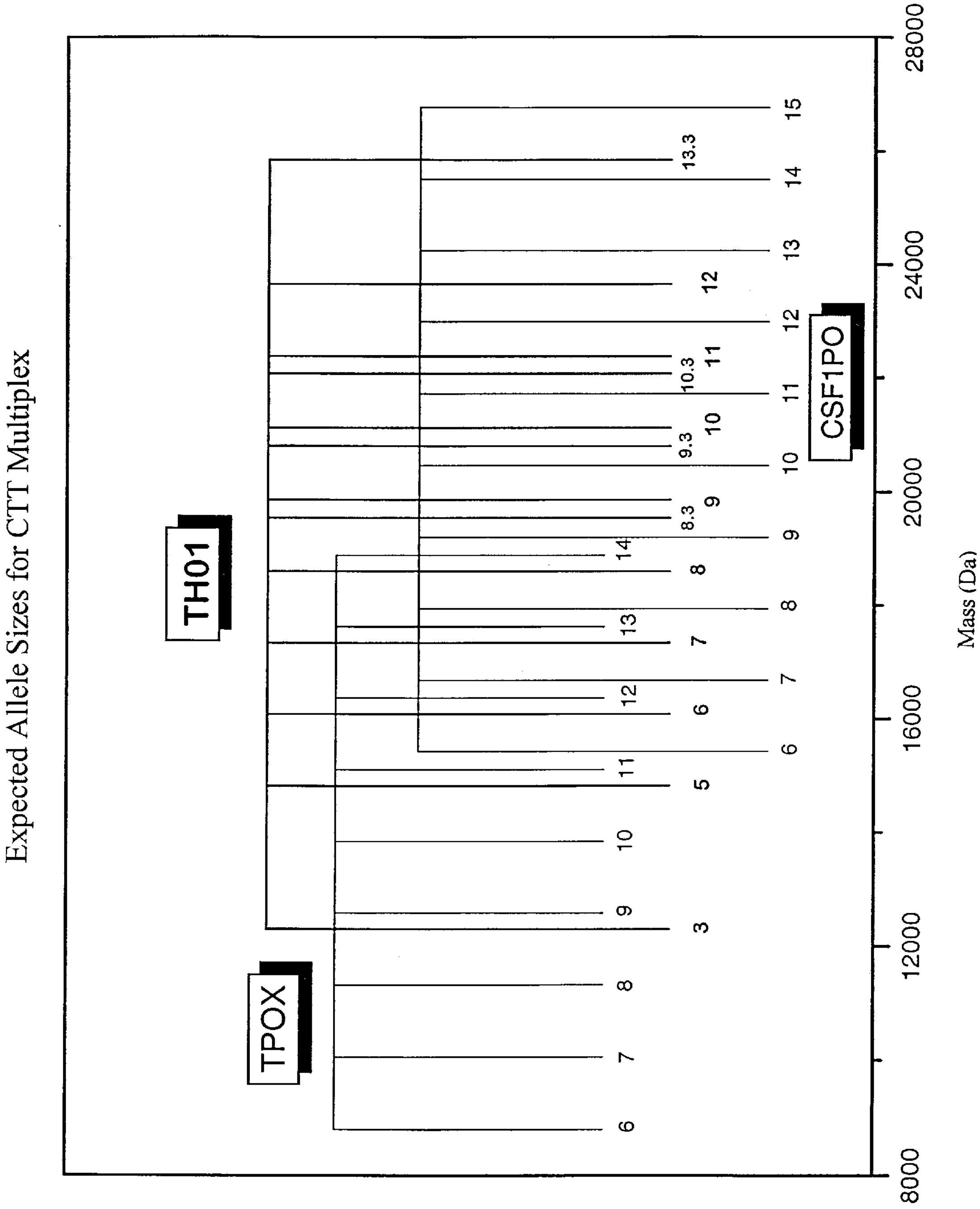
FIG. 8A shows the expected allele sizes for CTT multiplex analyses. The CTT multiplex is directed to the three STR loci CSF1PO, TPOX, and TH01.
Figure 8B:
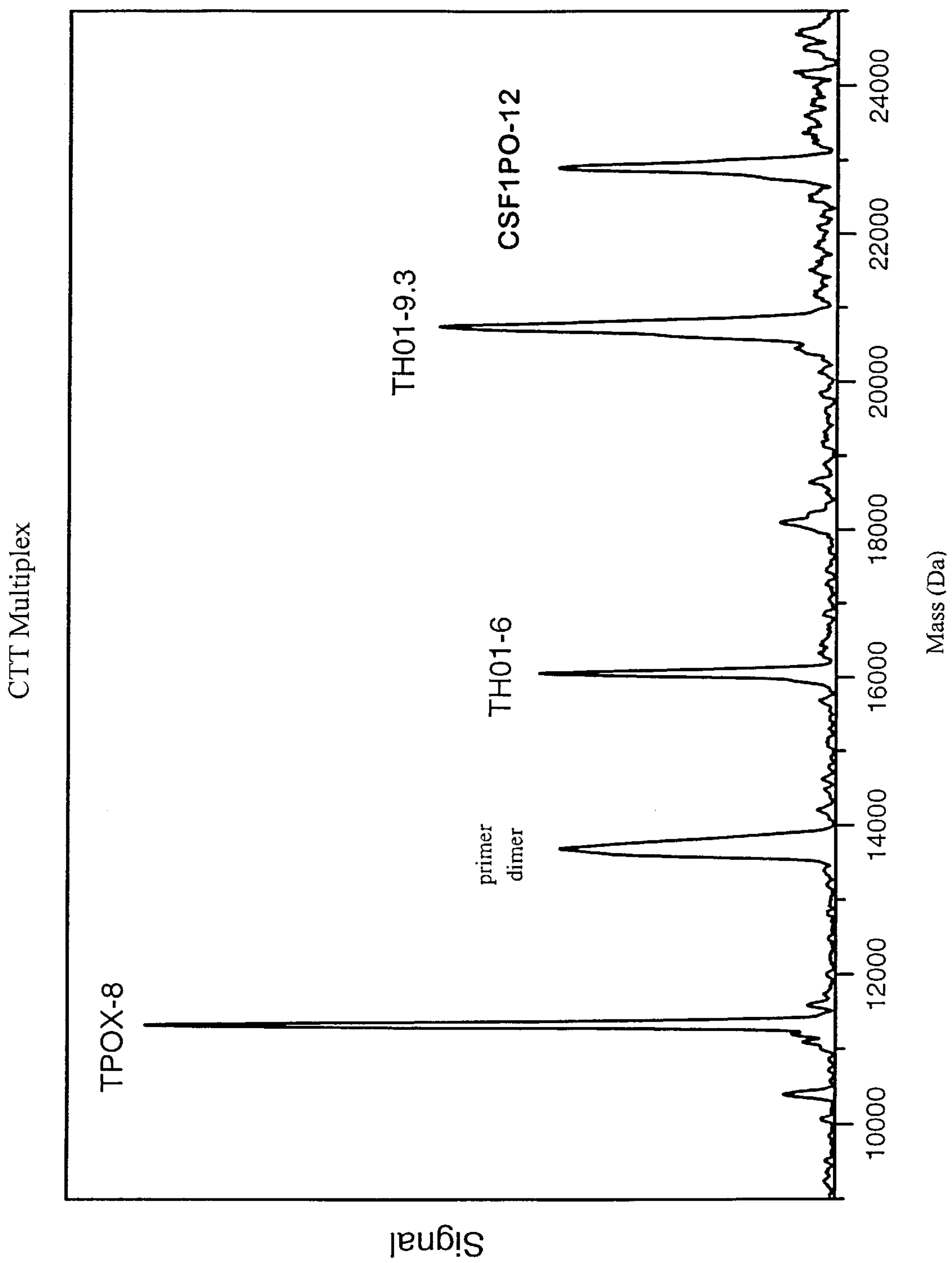
FIG. 8B illustrates the results of the analysis of a sample using the CTT multiplex. The sample is shown to contain a homozygous TPOX allele 8, heterozygous TH01 alleles 6 and 9.3, and a homozygous CSF1PO allele 12.

As seen in FIG. 8A, the possible alleles including microvariants, such as TH01 9.3, are resolvable from one another in all three STR systems even though they overlap in the mass range. FIG. 8B illustrates a result with this particular STR multiplex. The sample contains a homozygous TPOX allele 8, heterozygous TH01 alleles 6 and 9.3, and a homozygous CSF1PO allele 12. In this particular case, the strand containing an AATG or ATAG repeat was used in all three STR loci so that the same dideoxynucleotide triphoshate (ddC) could be used to terminate the strand on the opposite side of the repeat from the cleavable primer. After the extension reaction with the ddNTP and the cleavage reaction, the repeat region and only a flanking few bases on either side of the repeat are present for the three STR loci. Mass accuracy as well as resolution and sensitivity are improved in the mass spectrometer by going to smaller sizes for the STR alleles using this approach.

EXAMPLE 6

TWO STAGE MULTIPLEXING REACTION OUTSIDE PRIMERS FOR HIGHER LEVEL MULTIPLEX FOLLOWED BY GTS PRIMERS IN LOWER LEVEL MULTIPLEX THAT PRODUCE SMALLER PCR PRODUCTS

In a situation where there is a small or limited amount of DNA template available, a highly multiplexed PCR reaction may be performed initially followed by a second stage PCR with primers that are interior (i.e., closer to the repeat region) than those contained in the first multiplex ("nested PCR"). The first multiplex could include, for example, 8–14 STR loci that are PCR-amplified simultaneously. Aliquots of these amplicons could then be divided and reamplified in a second PCR reaction with primers for a subset of the STR loci already amplified. For example, six duplex reactions or four triplexes with mass spectroscopy primers could be performed to measure all of the STR loci in an initial 12-plex reaction. Primers used in these duplexes could be from those listed in Table 1. Provided that the primers for the first stage multiplex are outside (or at least identical to) the second stage primer sets, this approach will work for any PCR-compatible primers.

The advantage of the nested PCR approach is that a SAP-treatment is not required (as in Example 5) before the second stage reaction as dNTPs are used. However, measured STR alleles will be longer and thus more challenging to analyze in the mass spectrometer than STR allele products created with the primer termination reaction (ddN) approach described above.

EXAMPLE 7

FTA PAPER USED IN PCR REACTIONS IN PLACE OF EXTRACTED DNA

Liquid blood was stained on an FTA™ Card (Life Technologies, Gaithersburg, Md.) and allowed to air-dry for 1 hour. A small portion of blood-stained paper was cut out of the center of the spot and placed in a 0.6 mL tube. An aliquot of 50 μL FTA™ Purification Reagent (Life Technologies) was added to the tube and vortexed for several seconds. The tube was allowed to sit for 5 minutes at room temperature. The tube was vortexed again and the liquid in the tube was removed. Another aliquot of 50 μL FTA™ Purification Reagent was added to the tube and the vortexing and waiting steps were repeated as described above. The FTA™ paper was then washed a third time with FTA™ Purification Reagent and then washed twice more with deionized water. After these washes, the liquid was removed with a pipet and the FTA™ paper punch was left in the tube to air-dry for 1 hour.

The dried punch was added directly to PCR amplification mix in place of extracted human genomic DNA. PCR was performed as described in the other examples with no changes to amplification conditions or reagents. No decrease in PCR efficiency was observed when the FTA™ paper was compared to standard K562 human genomic DNA templates. The use of FTA™ paper greatly facilitates the automation of DNA typing procedures as extensive DNA extraction is not needed from liquid blood samples.

REFERENCES

The following references, to the extent that they provide exemplary procedural or other details supplementary to those set forth herein, are specifically incorporated herein by reference.

U.S. Pat. No. 4,683,202 Mullis
U.S. Pat. No. 5,364,759 Caskey et al.
U.S. Pat. No. 5,378,602 Polymeropoulos et al.
U.S. Pat. No. 5,599,666 Schumm et al.
U.S. Pat. No. 5,605,798 Köster
U.S. Pat. No. 5,700,642 Monforte et al.
U.S. Pat. No. 5,674,686 Schumm and Puers
U.S. Pat. No. 5,766,847 Jackie and Tautz
U.S. Pat. No. 5,496,562 Burgoyne Alford, Hammond, Coto, Caskey, "Rapid and efficient resolution of parentage by amplification of short tandem repeats," *Am. J. Hum. Genet.*, 55: 190–195, 1994.

Anker, Steinbrneck, Donis-Keller, "Tetranucleotide repeat polymorphism at the human thyroid peroxidase (hTPO) locus," *Hum. Mol. Genet.*, 1:137, 1992.

Becker, Li, Shaler, Hunter, Lin, Monforte, "Genetic analysis of short tandem repeat loci by time of flight mass spectrometry," Seventh International Symposium on Human Identification (1996), pp. 158–162, 1997.

Dubovsky, Sheffield, Duyk, Weber, "Sets of short tandem repeat polymorphisms for efficient linkage screening of the human genome," *Hum. Mol. Genet.*, 4: 449–452, 1995.

Edwards, Civitello, Hammond, Caskey, "DNA typing and genetic mapping with trimeric and tetrameric tandem repeats," *Am. J. Hum. Genet.*, 49:746–756, 1991.

Fregeau and Fourney, "DNA typing with fluorescently tagged short tandem repeats: a sensitive and accurate approach to human identification," *BioTechniques*, 15:100–119, 1993.

Hammond, Jin, Zhong, Caskey, Chakraborty, "Evaluation of 13 short tandem repeat loci for use in personal identification applications," *Am. J. Hum. Genet.*, 55:175–189, 1994.

Hauge and Litt, "A study of the origin of 'shadow bands' seen when typing dinucleotide repeat polymorphisms by the PCR™," *Hum. Mol. Genet.*, 2:411–415, 1993.

Hearne and Todd, "Tetranucleotide repeat polymorphism at the HPRT locus," *Nucleic Acids Res.*, 19:5450, 1991.

Kimpton, Walton, Gill, "A further tetranucleotide repeat polymorphism in the vWF gene," *Hum. Mol. Genet.*, 1:287, 1992.

Kimpton, Gill, Walton, Urquhart, Millican, Adams, "Automated DNA profiling employing multiplex amplification of short tandem repeat loci," *PCR™ Meth. Appl.*, 3:13–22, 1993.

Kimpton, Oldroyd, Watson, Frazier, Johnson, Millican, Urquhart, Sparkes, Gill, "Validation of highly discriminating multiplex short tandem repeat amplification systems for individual identification," *Electrophoresis*, 17:1283–1293, 1996.

Lareu, Pestoni, Schurenkamp, Rand, Brinkmann, Carracedo, "A highly variable STR at the D12S391 locus," *Int. J. Leg. Med.*, 109:134–138, 1996.

Lygo, Johnson, Holdaway, Woodroffe, Whitaker, Clayton, Kimpton, Gill, "The validation of short tandem repeat (STR) loci for use in forensic casework," *Int. J. Leg. Med.*, 107:77–89, 1994.

Polymeropoulos, Rath, Xiao, Merril, "Tetranucleotide repeat polymorphism at the human c-fes/fps proto-oncogene (FES)," *Nucleic Acids Res.*, 19:4018, 1991.

Polymeropoulos, Rath, Xiao, Merril, "Tetranucleotide repeat polymorphism at the human coagulation factor XIII A subunit gene (F13A1)," *Nucleic Acids Res.*, 19:4306, 1991.

Polymeropoulos, Xiao, Rath, Merril, "Tetranucleotide repeat polymorphism at the human tyrosine hydroxylase gene (TH)," *Nucleic Acids Res.*, 19:3753, 1991.

Puers, Hammond, Caskey, Lins, Sprecher, Brinkmann, Schumm, "Allele ladder characterization of the short tandem repeat polymorphism located in the 5' flanking region to the human coagulation factor XIII A subunit gene," *Genomics*, 23:260–264, 1994.

Puers, Hammond, Jin, Caskey, Schumm, "Identification of repeat sequence heterogeneity at the polymorphic short tandem repeat locus HUMTH01[AATG]n and reassignment of alleles in population analysis by using a locus-specific allele ladder," *Am. J. Hum. Genet.*, 53:953–958, 1993.

Roewer, Arnemann, Spurr, Grzeschik, Epplen, "Simple repeat sequences on the human Y chromosome are equally polymorphic as their autosomal counterparts," *Hum. Genet.*, 89:389–394, 1992.

The Utah Marker Development Group "A collection of ordered tetranucleotide-repeat markers from the human genome," *Am. J. Hum. Genet.*, 57:619–628, 1995.

Weber and May, "Abundant class of human DNA polymorphisms which can be typed using the polymerase chain reaction," *Am. J. Hum. Genet.*, 44:388–396, 1989.

Ziegle, Su, Corcoran, Nie, Mayrand, Hoff, McBride, Kronick, Diehl, "Application of automated DNA sizing technology for genotyping microsatellite loci," *Genomics*, 14:1026–1031,1992.

Braun, A., et al., "Detecting CFTR gene mutations by using primer oligo base extension and mass spectrometry," *Clin. Chem.* 43:1151–1158 (1997).

Braun, A., et al., "Improved Analysis of Microsatellites Using Mass Spectrometry," *Genomics* 46:18–23 (1997).

Butler, J. M., et al., "Reliable Genotyping of Short Tandem Repeat Loci without an Allelic Ladder Using Time-of-Flight Mass Spectrometry," *Int. J. Legal Med.*, in press (1998).

Butler, J. M., et al., "Rapid and Automated Analysis of Short Tandem Repeat Loci Using Time-of-Flight Mass Spectrometry," *Proceedings of the Eighth International Symposium on Human Identification* 1997, Promega Corporation, pp. 94–101 (1998).

Butler, J. M., et al., "High-throughput STR Analysis by Time-of-Flight Mass Spectrometry," *Proceedings of the Second European Symposium on Human Identification* 1998, Promega Corporation, in press (1998).

Huang, N. E., et al., "Chinese population data on three tetrameric short tandem repeat loci-HUMTH01, TPOX, and CSF1PO-derived using multiplex PCR and manual typing," *Forensic Sci. Int.* 71:131–136 (1995).

Kayser, M., et al., "Evaluation of Y-chromosomal STRs: a multicenter study," *Int. J. Legal Med.* 110:125–133 (1997).

Little, D. P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," *Anal. Chem.* 69:4540–4546 (1997).

Little, D. P., et al., "Mass Spectrometry from Miniaturized Arrays for Full Comparative DNA Analysis," *Nature Med.* 3:1413–1416 (1997).

Ross, P. L., and Belgrader, P., "Analysis of Short Tandem Repeat Polymorphisms in Human DNA by Matrix-Assisted Laser Desorption/Ionization Mass Spectrometry," *Anal. Chem.* 69:3966–3972 (1997).

Ross, P. L., et al., "Analysis of DNA Fragments from Conventional and Microfabricated PCR Devices Using Delayed Extraction MALDI-TOF Mass Spectrometry," *Anal. Chem.* 70:2067–2073 (1998).

Taranenko, N. I., et al., "Matrix-assisted Laser Desorption/Ionization for Short Tandem Repeat Loci," *Rapid Commun. Mass Spectrom.* 12:413–418 (1998).

Wenz, H.-M., et al., "High-Precision Genotyping by Denaturing Capillary Electrophoresis," *Genome Res.* 8:69–80 (1998).

What is claimed is:

1. A method for multiplexing the identification of more than one DNA tandem nucleotide repeat region from more than one DNA tandem nucleotide repeat loci, comprising:

obtaining more than one nucleic acid extension product by extending one or more primers complementary to sequences flanking the DNA tandem nucleotide repeat region, and;

determining the masses of more than one nucleic acid extension product simultaneously by mass spectrometry, wherein the nucleic acid extension products have overlapping allelic mass ranges.

2. The method of claim 1, wherein a 3' end of one or more primers immediately flanks a DNA tandem nucleotide repeat region.

3. The method of claim 1, wherein one or more primers comprise a sequence complementary to up to one tandem repeat of the DNA tandem nucleotide repeat locus.

4. The method of claim 3, wherein one or more primers comprise a sequence complementary to up to two tandem repeats of the DNA tandem nucleotide repeat locus.

5. The method of claim 4, wherein one or more primers comprise a sequence complementary to up to three tandem repeats of the DNA tandem nucleotide repeat locus.

6. The method of claim 1, wherein the extension of at least one primer is terminated using a chain termination reagent.

7. The method of claim 6, wherein the chain termination reagent is a dideoxynucleotide triphospate.

8. The method of claim 6, wherein at least one target nucleic acid extension product contains a mass modifying group.

9. The method of claim 8, wherein the mass modifying group comprises a mass modified nucleotide.

10. The method of claim 8, wherein the mass modifying group comprises a nonstandard deoxyribonucleotide.

11. The method of claim 1, wherein at least one primer comprises a cleavable site and wherein the cleavable site comprises a recognition site for a restriction endonuclease, an exonuclease blocking site, or a chemically cleavable site.

12. The method of claim 11, wherein the cleavable site comprises a recognition site for a restriction endonuclease.

13. The method of claim 11, wherein the cleavable site comprises an exonuclease blocking site.

14. The method of claim 11, wherein the cleavable site comprises a chemically cleavable site.

15. The method of claim 8, wherein the mass modifying group is incorporated during extension of the nucleic acid extension product.

16. The method of claim 8, wherein the mass modifying group is incorporated after extension of the nucleic acid extension product.

17. A method for multiplexing the identification of more than one DNA tandem nucleotide repeat region from more than one DNA tandem nucleotide repeat loci, comprising:

obtaining more than one nucleic acid amplification product by amplifying two or more primers complementary to sequences flanking the DNA tandem nucleotide repeat region; and determining the masses of more than one nucleic acid amplification product simultaneously by mass spectrometry, wherein the nucleic acid extension products have overlapping allelic mass ranges.

18. The method of claim 17, wherein a 3' end of one or more primers immediately flanks a DNA tandem nucleotide repeat region.

19. The method of claim 17, wherein one or more primers comprise a sequence complementary to up to one tandem repeat of the DNA tandem nucleotide repeat locus.

20. The method of claim 19, wherein one or more primers comprise a sequence complementary to up to two tandem repeats of the DNA tandem nucleotide repeat locus.

21. The method of claim 20, wherein one or more primers comprise a sequence complementary to up to three tandem repeats of the DNA tandem nucleotide repeat locus.

22. The method of claim 17, wherein at least one target nucleic acid amplification product contains a mass modifying group.

23. The method of claim 22, wherein the mass modifying group comprises a mass modified nucleotide.

24. The method of claim 22, wherein the mass modifying group comprises a nonstandard deoxyribonucleotide.

25. The method of claim 17, wherein at least one primer comprises a cleavable site and wherein the cleavable site comprises a recognition site for a restriction endonuclease, an exonuclease blocking site, or a chemically cleavable site.

26. The method of claim 25, wherein the cleavable site comprises a recognition site for a restriction endonuclease.

27. The method of claim 25, wherein the cleavable site comprises an exonuclease blocking site.

28. The method of claim 25, wherein the cleavable site comprises a chemically cleavable site.

29. The method of claim 22, wherein the mass modifying group is incorporated during amplification.

30. The method of claim 22, wherein the mass modifying group is incorporated after amplification.

* * * * *